(12) United States Patent
Callas et al.

(10) Patent No.: US 9,795,481 B2
(45) Date of Patent: Oct. 24, 2017

(54) EPICARDIAL CLIP

(75) Inventors: Peter Tachi Callas, Castro Valley, CA (US); Pierluca Lombardi, San Jose, CA (US); Michael C. Stewart, Milpitas, CA (US); Liming Lau, Mountain View, CA (US); Mark S. Juravic, San Francisco, CA (US); Evan Anderson, San Francisco, CA (US); Joe Lamberti, Castro Valley, CA (US); Albert K. Chin, Palo Alto, CA (US); Tammy Wang, Chula Vista, CA (US)

(73) Assignee: Maquet Cardiovascular LLC, Wayne, NJ (US)

( * ) Notice: Subject to any disclaimer, the term of this patent is extended or adjusted under 35 U.S.C. 154(b) by 843 days.

(21) Appl. No.: 13/597,735

(22) Filed: Aug. 29, 2012

(65) Prior Publication Data

US 2012/0323314 A1 Dec. 20, 2012

Related U.S. Application Data

(62) Division of application No. 12/166,247, filed on Jul. 1, 2008, now Pat. No. 8,647,254.

(51) Int. Cl.
*A61F 2/24* (2006.01)

(52) U.S. Cl.
CPC .......... *A61F 2/2451* (2013.01); *A61F 2/2478* (2013.01); *A61F 2/2481* (2013.01); *A61F 2/2442* (2013.01); *A61F 2/2496* (2013.01)

(58) Field of Classification Search
CPC ........................................................ A61F 2/24
USPC ........................................................ 623/2.36
See application file for complete search history.

(56) References Cited

U.S. PATENT DOCUMENTS

| | | | |
|---|---|---|---|
| 4,042,979 | A | 8/1977 | Angell |
| 5,104,407 | A | 4/1992 | Lam et al. |
| 6,050,936 | A | 4/2000 | Schweich et al. |
| 6,402,781 | B1 | 6/2002 | Langberg et al. |
| 6,701,929 | B2 | 3/2004 | Hussein |
| 6,764,510 | B2 | 7/2004 | Vidlund et al. |
| 6,808,488 | B2 | 10/2004 | Mortier et al. |
| 7,166,127 | B2 | 1/2007 | Spence et al. |
| 2001/0014811 | A1 | 8/2001 | Hussein |
| 2002/0111533 | A1 | 8/2002 | Melvin |
| 2004/0064014 | A1 | 4/2004 | Melvin et al. |
| 2004/0133063 | A1 | 7/2004 | McCarthy et al. |
| 2004/0133069 | A1 | 7/2004 | Shapland et al. |
| 2004/0210240 | A1 | 10/2004 | Saint |
| 2005/0119734 | A1 | 6/2005 | Spence et al. |

(Continued)

OTHER PUBLICATIONS

Office Action for U.S. Appl. No. 12/166,247 mailed Oct. 16, 2012.

*Primary Examiner* — Matthew Schall
(74) *Attorney, Agent, or Firm* — Law Office of Alan W. Cannon

(57) ABSTRACT

An epicardial clip for reshaping the annulus of the mitral valve of a heart includes a curved member having an anterior segment configured to be positioned in the transverse sinus of the heart, a posterior segment configured to be positioned on the posterior side of the heart, such as on or inferior to the atrioventricular groove, and a lateral segment extending between the anterior segment and the posterior segment. The lateral segment includes a curve such that the first end of the member is positioned at or above the plane of the mitral valve and the second end of the member is positioned at or below the plane of the mitral valve.

7 Claims, 57 Drawing Sheets

(56) References Cited

U.S. PATENT DOCUMENTS

| | | |
|---|---|---|
| 2006/0025858 A1 | 2/2006 | Alameddine |
| 2006/0036317 A1 | 2/2006 | Vidlund et al. |
| 2006/0100699 A1 | 5/2006 | Vidlund et al. |
| 2006/0129051 A1 | 6/2006 | Rowe et al. |
| 2006/0241746 A1 | 10/2006 | Shaoulian et al. |
| 2006/0241748 A1 | 10/2006 | Lee et al. |
| 2006/0253129 A1 | 11/2006 | Liddicoat et al. |

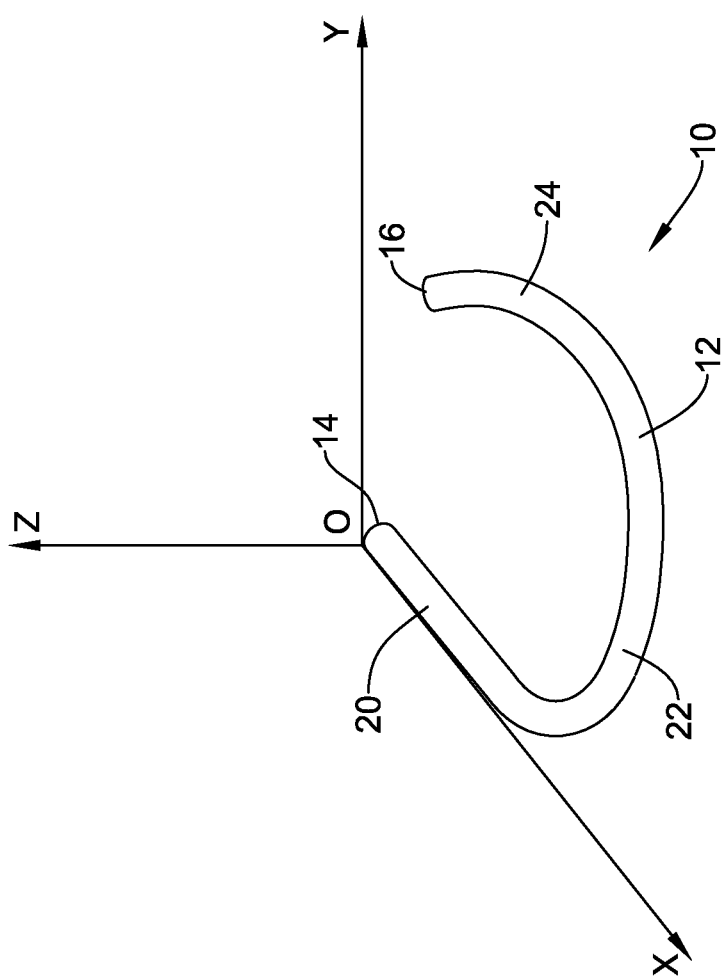

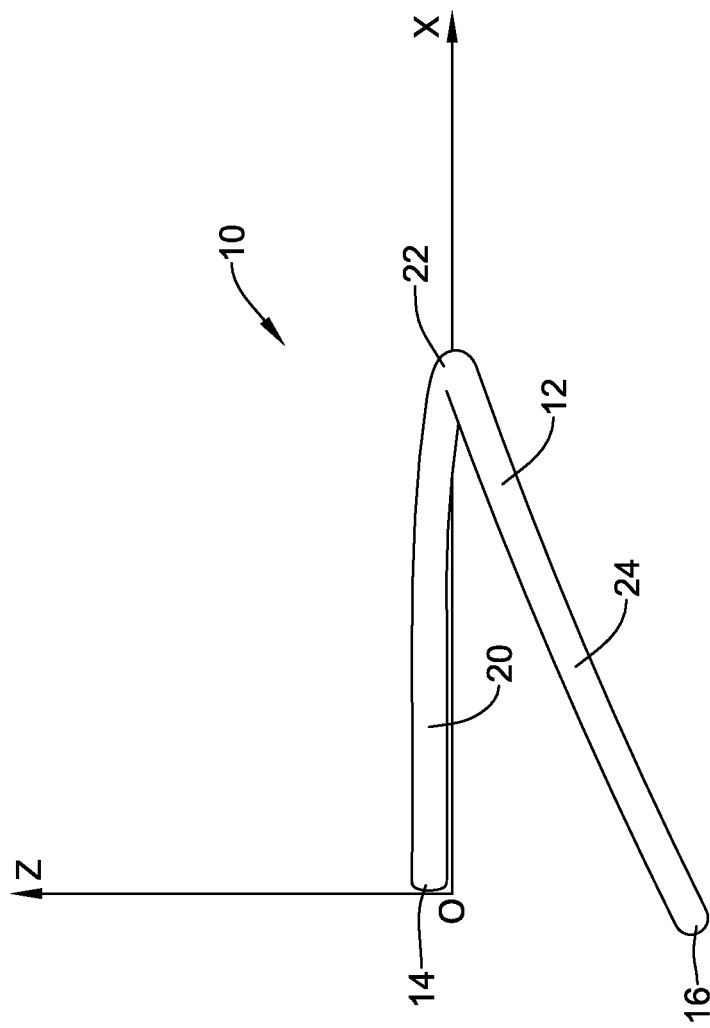

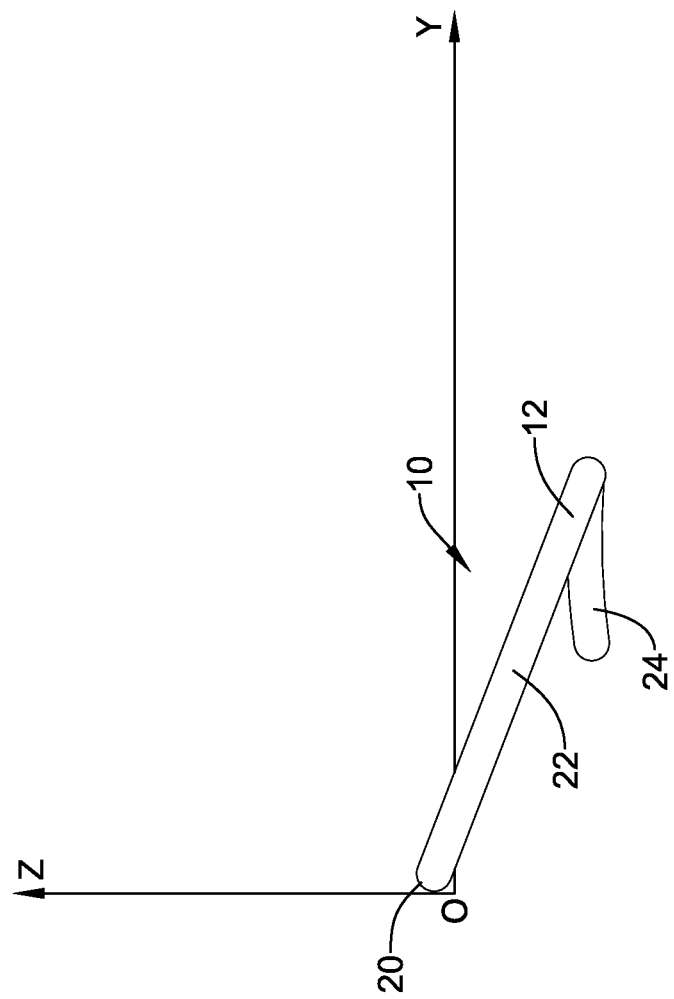

EPICARDIAL CLIP

CROSS REFERENCE TO RELATED APPLICATION

This application is a divisional of U.S. patent application Ser. No. 12/166,247 now U.S. Pat. No. 8,647,254, filed Jul. 1, 2008, which is hereby incorporated by reference.

TECHNICAL FIELD

The disclosure is directed to medical devices for reshaping the annulus of a heart valve. More particularly, the disclosure is directed to an epicardial clip which may be positioned exterior of the epicardium of a heart to reshape the annulus of the mitral valve to improve coaptation of the leaflets of the mitral valve.

BACKGROUND

The mitral valve is located between the left atrium and the left ventricle of the heart. During normal operation, the mitral valve opens during diastole, allowing blood to flow from the left atrium into the left ventricle. During systole, the mitral valve closes, causing high pressure blood to exit the left ventricle through the aorta. Mitral valve regurgitation is a cardiac condition in which the posterior leaflet of the mitral valve does not fully contact the anterior leaflet of the valve during systole, thus a gap remains between the leaflets of the mitral valve during systole. The gap remaining between the leaflets allows retrograde blood flow to pass from the left ventricle into the left atrium through the mitral valve. Thus, mitral regurgitation reduces the volume of blood pumped out of the heart to the aorta during each cardiac cycle, thus reducing the efficiency of the heart. Mitral regurgitation may exist for any of several reasons, including congenital malformations of the valve, ischemic disease, or effects of cardiomyopathy, such as dilated (congestive) cardiomyopathy (i.e., enlarging of the heart).

Conventional techniques for treating dysfunctions of the mitral valve typically include highly invasive, open heart surgical procedures in order to replace or repair the dysfunctioning mitral valve. Some surgical procedures include the implantation of a replacement valve (e.g., animal valve or artificial mechanical valve). Other techniques include the use of annuloplasty rings which are surgically placed around the annulus of the mitral valve within the chamber of the heart and sutured into place. The presence of the annuloplasty ring alters the geometry of the annulus of the mitral valve in order to improve coaptation of the leaflets of the valve. Another surgical technique which requires accessing one or more chambers of the heart is leaflet coaptation. Leaflet coaptation (e.g., Alfieri edge-to-edge repair) is a surgical procedure in which the valve leaflets are sutured together (e.g., bow-tie suture) to improve coaptation of the leaflets. A further surgical technique includes extending a tensioning cord across a chamber of the heart to alter the geometry of the heart chamber. The tensioning cord, which extends through a chamber of the heart, and thus is in contact with blood in the heart chamber, pulls opposing walls of the heart toward one another to reduce heart wall tension and/or reposition the papillary muscles within the chamber. These techniques typically require opening the heart and/or entering one or more of the chambers of the heart to gain direct access to the mitral valve.

Therefore, it is desirable to devise a less invasive technique for treating mitral valve regurgitation. Namely, it is desirable to devise a passive device which may be positioned exterior of the heart to alter the geometry of the annulus of the mitral valve without the need to gain access to the interior of the heart. Thus, the device may be placed in contact with the epicardial surface of the heart without being in contact with blood within the heart.

SUMMARY

The disclosure is directed to several alternative designs, materials and methods of manufacturing medical device structures and assemblies.

Accordingly, one illustrative embodiment is an epicardial clip for reshaping the annulus of the mitral valve of a heart, the mitral valve lying in a plane between the left atrium and the left ventricle of the heart. The epicardial clip includes a curved member having a first end and a second end. The member forms an anterior segment configured to be positioned in the transverse sinus of the heart, a posterior segment configured to be positioned on the posterior side of the heart, such as on or inferior to the atrioventricular groove or in the oblique sinus of the heart, and a lateral segment extending between the anterior segment and the posterior segment. The lateral segment includes a curve, e.g., helical, such that the first end of the member is positioned above the plane of the mitral valve and the second end of the member is positioned below the plane of the mitral valve. The transverse sinus is a pericardial cavity of the heart located posterior to the aorta and pulmonary trunk and anterior to the left atrium, the atrioventricular groove is the natural junction between the left atrium and the left ventricle on the posterior of the heart, and the oblique sinus is a blind pericardial cavity posterior of the heart.

Another illustrative embodiment is an epicardial clip for reshaping the annulus of the mitral valve of a heart, the mitral valve lying in a plane between the left atrium and the left ventricle of the heart. The clip includes a curved member having a first end and a second end. The member includes an anterior segment positioned superior to the plane of the mitral valve, a posterior segment positioned inferior to the plane of the mitral valve, and a lateral segment extending between the anterior segment and the posterior segment. The lateral segment includes a curve, e.g., helical, extending around a lateral portion of the heart.

Yet another illustrative embodiment is an epicardial clip for reshaping the annulus of the mitral valve of a heart. The clip may have a complex geometry which may be defined in an imaginary coordinate system. The coordinate system has an origin, an x-axis extending from the origin, a y-axis extending from the origin and perpendicular to the x-axis, and a z-axis extending from the origin and perpendicular to both the x-axis and the y-axis. The clip includes a curved member having a first end and a second end. The curved member forms an anterior segment, a posterior segment and a lateral segment extending between the anterior segment and the posterior segment. As a point of reference, the first end of the member is positioned at the origin of the imaginary coordinate system. The anterior segment begins at the origin and extends in the positive x-direction along the x-axis. The lateral segment, which extends from the anterior segment, includes a straight portion extending in the positive y-direction and a curve portion extending to the posterior segment. The posterior segment extends from the lateral segment in the negative x-direction. The posterior segment may generate a coordinate change in the x-direction, a coordinate change in the y-direction, and a coordinate change in the z-direction. Furthermore, the lateral segment may generate a coordinate change in the z-direction between the anterior segment and the posterior segment.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which:

FIG. 3A shows the epicardial clip of FIG. 1 in an imaginary three-dimensional x-y-z coordinate system;

FIG. 3C is a two-dimensional view of the epicardial clip toward the x-z plane of the three-dimensional coordinate system of FIG. 3A;

FIG. 3D is a two-dimensional view of the epicardial clip toward the y-z plane of the three-dimensional coordinate system of FIG. 3A;

FIG. 24 is a superior view of a heart in which the epicardial clip of FIGS. 19 and 20 has been positioned on;

Figure 1:
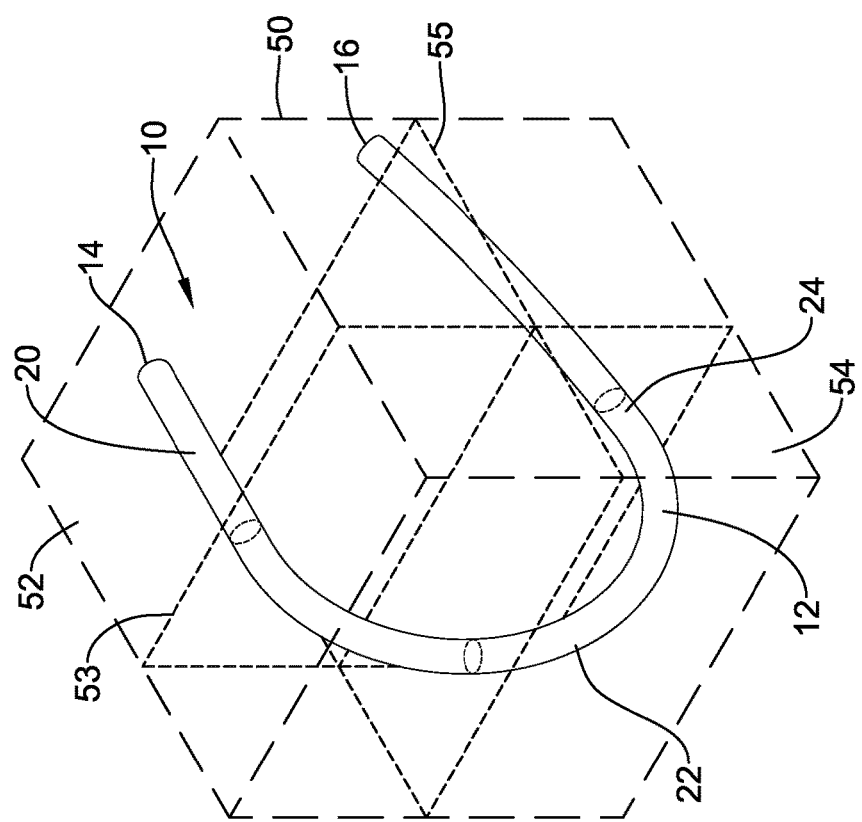
FIG. 1 is a perspective view of an exemplary epicardial clip positioned in an imaginary box.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

As used in the specification and the appended claims, the term "anterior" is used in its anatomical sense to mean "toward the front, in front of, or the front surface of."

As used in the specification and the appended claims, the term "posterior" is used in its anatomical sense to mean "toward the back, in back of, or the back surface of."

As used in the specification and the appended claims, the term "superior" is used in its anatomical sense to mean "above, over top of, directed upward or toward the head."

As used in the specification and the appended claims, the term "inferior" is used in its anatomical sense to mean "below, underneath, directed downward or toward the feet."

As use in the specification and the appended claims, the term "lateral" is used in its anatomical sense to mean "a position or direction farther from the sagittal or median plane or midline of the body, to the side of, or the side surface of."

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Now turning to the figures, an epicardial clip 10 is shown in FIG. 1. The epicardial clip 10 is depicted in an imaginary box 50 in order to further describe the three-dimensional geometry of the epicardial clip 10. Additionally, two imaginary planes 53, 55 are shown in the imaginary box 50 in order to further illustrate the geometry of the epicardial clip 10. The epicardial clip 10 may include a curved member 12 having a first end 14 and a second end 16. In some embodiments the curved member 12 may be a wire, bar, rod, strap, or the like. In some embodiments, the epicardial clip 10 may be formed of a single continuous wire, or the epicardial clip 10 may include a plurality of wires interconnected. The curved member 12 includes an anterior segment 20 proximate the first end 14, a posterior segment 24 proximate the second end 16, and a lateral segment 22 intermediate the anterior segment 20 and the posterior segment 24. In other words, the lateral segment 22 is located between the anterior segment 20 and the posterior segment 24 of the member 12. As shown in FIG. 1, in some embodiments the anterior segment 20 may include a straight portion, the posterior segment 24 may include a curved or arced portion, and/or the lateral segment 22 may include a curved portion, e.g., a helical portion, connecting the anterior segment 20 and the posterior segment 24. In some embodiments, the anterior segment 20 may include a curved portion and/or the posterior segment 24 may include a straight segment. The shape (e.g., curvature) of the segments of the member 12 may be chosen such that the curvature of the member 12 contours the approximate shape of the heart. In some embodiments, the member 12 may be formed of a flexible material, such that the curvature of the member 12 may be altered as needed during a medical procedure to correspond to the anatomical shape of a patient's heart and/or allowing deformation around an anatomical region of the heart. In other embodiments, the member 12 may be formed of a non-flexible or rigid material, having a permanent curvature which may not be readily bent to an ad hoc curvature.

The member 12 may be formed of any suitable material. For example, the member 12 may be made from a metal, metal alloy, polymer, a metal-polymer composite, combinations thereof, and the like, or any other suitable material. Some examples of suitable metals and metal alloys include stainless steel, such as 304V, 304L, and 316L stainless steel; mild steel; titanium alloys including titanium alpha-beta alloys, such as 6AL-4V (e.g., UNS: R56400); nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium alloys; combinations thereof; and the like; or any other suitable material.

Some examples of suitable polymers may include fluorinated ethylene propylene (FEP), polyoxymethylene (POM, for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, polyester, polybutylene terephthalate (PBT), polyethylene terephthalate (PET), polyetheretherketone (PEEK), polyimide (PI), biocompatible polymers, other suitable materials, or mixtures, combinations, copolymers thereof, polymer/metal composites, and the like.

Figure 2A:
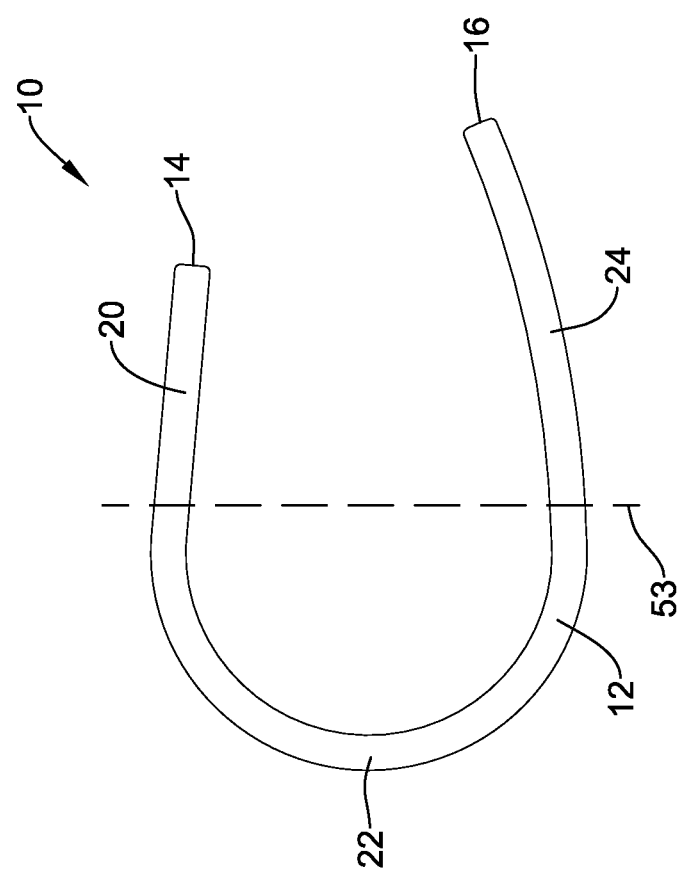
FIG. 2A is a top view of the epicardial clip of FIG. 1.

FIG. 2A is a top view of the clip 10 taken with respect to the orientation of the clip 10 shown in FIG. 1. The view shown in FIG. 2A is taken looking directly down toward the top 52 of the imaginary box 50 shown in FIG. 1 and showing the imaginary plane 53. As shown in FIG. 2A, the clip 10 may have a generally U-shape or C-shape when viewed with this orientation. The clip 10 may be shaped such that the distance across the clip 10 between the anterior segment 20 and the posterior segment 24 is closest between the first end 14 of the member 12 and the second end 16 of the member 12. As discussed later herein, the distance between the first end 14 and the second end 16 may determine the final anterior-posterior diameter of the mitral valve. The anterior segment 20 may be substantially straight, and thus capable of residing in the transverse sinus of the heart. The posterior segment 24 may be arcuate, corresponding to the semi-circular curvature of the posterior ventricular wall of the heart. The lateral segment 22 may have a helical curvature routing around the left lateral side of the heart, placing the anterior segment 20 in the transverse sinus and the posterior segment 24 on the posterior of the heart, such as on or inferior to the atrioventricular groove or in the oblique sinus of the heart. In some embodiments, the radius of curvature of the lateral segment 22 may be in the range of about 5 to about 70 millimeters, or in the range of about 30 to about 46 millimeters, for example, about 10 millimeters, about 20 millimeters, about 30 millimeters, about 40 millimeters, about 50 millimeters, about 60 millimeters, about 70 millimeters, or other desired radius of curvature such that the lateral segment 22 may be properly positioned around a lateral side of a heart. In some embodiments the lateral segment 22 may be routed around, over and/or under the left atrial appendage of the heart. In other embodiments, the lateral segment 22 may be routed over the left atrium of the heart.

Figure 2B:
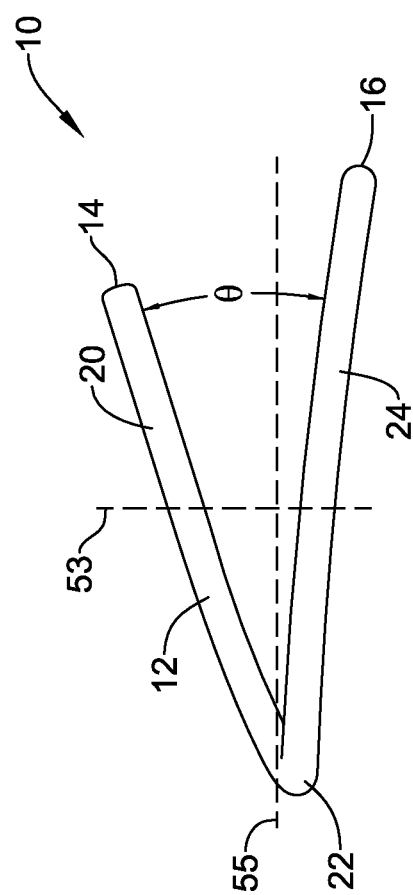
FIG. 2B is a side view of the epicardial clip of FIG. 1.

FIG. 2B is a side view of the clip 10 taken with respect to the orientation of the clip 10 shown in FIG. 1. The view shown in FIG. 2B is taken looking directly toward the front side 54 of the imaginary box 50 shown in FIG. 1 and showing the imaginary planes 53 and 55. As shown in FIG. 2B, the anterior segment 20 may lie in an imaginary plane and the posterior segment 24 may lie in an imaginary plane. The imaginary plane of the posterior segment 24 may be located at an acute angle to the imaginary plane of the anterior segment 20. In some embodiments, the curvature of the lateral segment 22, such as helical geometry of the lateral segment, may control the angle θ between the anterior segment 20 and the posterior segment 24. For example, in some embodiments the angle θ may be in the range of about 5 to about 20 degrees, for example, about 5 degrees, about 10 degrees, about 15 degrees, about 20 degrees, or any other suitable angle. Thus, the three-dimensional configuration of the clip 10 means that the clip 10 does not necessarily lie in a single imaginary plane.

Figure 3B:
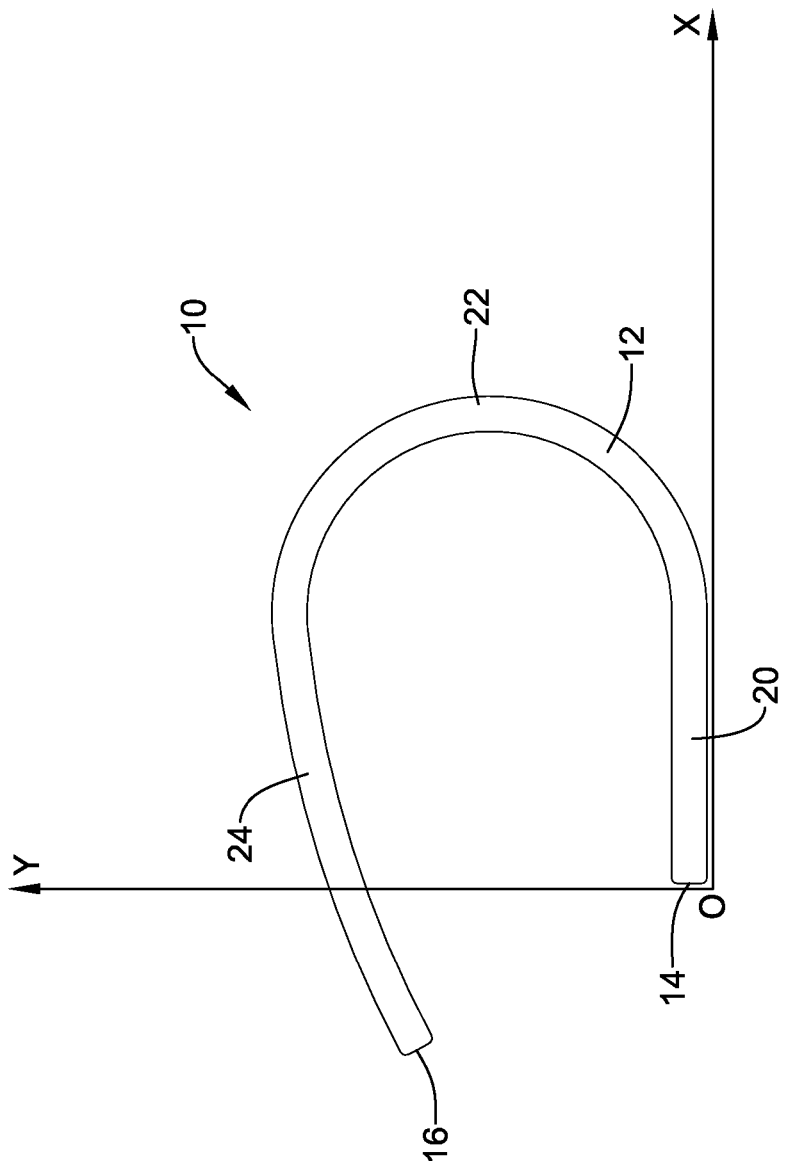
FIG. 3B is a two-dimensional view of the epicardial clip toward the x-y plane of the three-dimensional coordinate system of FIG. 3A.

FIGS. 3A-3D show the clip 10 placed in a coordinate system having an origin O, an x-axis extending from the origin O, a y-axis extending from the origin O and perpendicular to the x-axis, and a z-axis extending from the origin O and perpendicular to both the x-axis and the y-axis. FIG. 3A shows the clip 10 in the three-dimensional x-y-z coordinate system. FIGS. 3B-3D show two-dimensional views of the clip 10 in each of an x-y coordinate system, an x-z coordinate system, and a y-z coordinate system. FIG. 3B is a view looking directly at the x-y plane (i.e., a plane passing through both the x-axis and the y-axis). FIG. 3C is a view looking directly at the x-z plane (i.e., a plane passing through both the x-axis and the z-axis). FIG. 3D is a view looking directly at the y-z plane (i.e., a plane passing through both the y-axis and the z-axis).

As shown in relation with the coordinate system with the first end 14 of the member 12 positioned at the origin O, the anterior segment 20 extends in the x-direction (e.g., positive x-direction) along the x-axis. The anterior segment 20 may lie in the x-y plane of the coordinate system. The lateral segment 22, which may include a curve, such as a helical curve, extends from the anterior segment 20, and may generate a coordinate change in the z-direction (e.g., negative z-direction) between the anterior segment 20 and the posterior segment 24. The posterior segment 24 extends from the lateral segment 22 and generates a coordinate change in the x-direction (e.g., negative x-direction), a coordinate change in the y-direction (e.g., negative y-direction), and a coordinate change in the z-direction (e.g., negative z-direction). Thus, the posterior segment 24 does not lie in the x-y plane, the x-z plane, or the y-z plane of the coordinate system. Thus, the member 12 may include components which extend in each of the x-direction, the y-direction, and the z-direction, and does not lie in a single plane. In some embodiments, the lateral segment 22, extending from the anterior segment 20, may include a straight portion extending in the y-direction (e.g., positive y-direction) and a curve portion extending to the posterior segment.

Figure 4A:
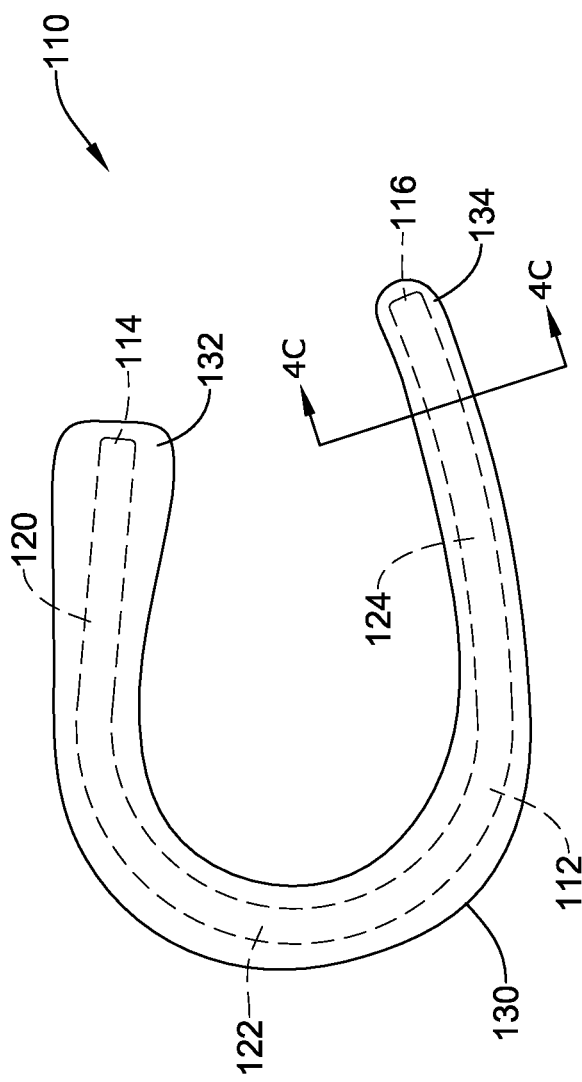
FIG. 4A is a top view of another exemplary epicardial clip.
Figure 4B:
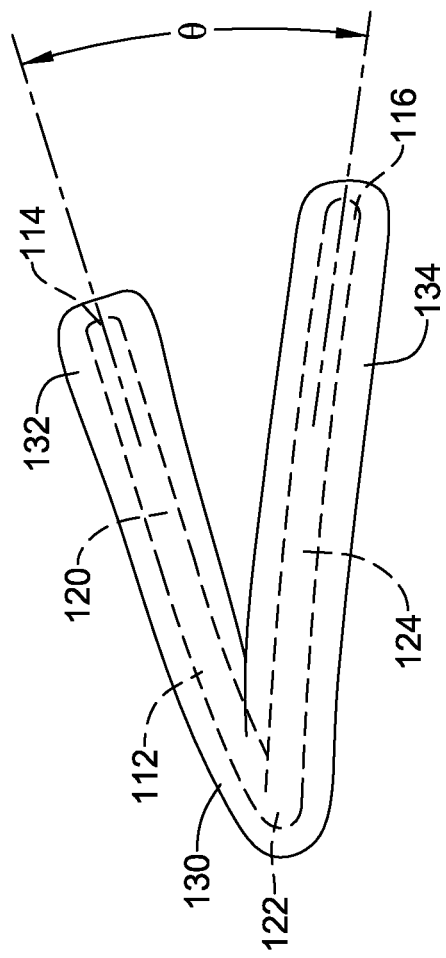
FIG. 4B is a side view the epicardial clip of FIG. 4A.

FIGS. 4A and 4B show another embodiment of an epicardial clip 110. The epicardial clip 110 may include a curved member 112 (see also FIG. 4C), such as a wire or strap, similar to the curved member 12 of FIG. 1. The curved member 112 may have substantially the same shape and curvature as the member 12 of FIG. 1, thus, additional discussion of the curvature of the member 112 is not necessary.

Figure 4C:
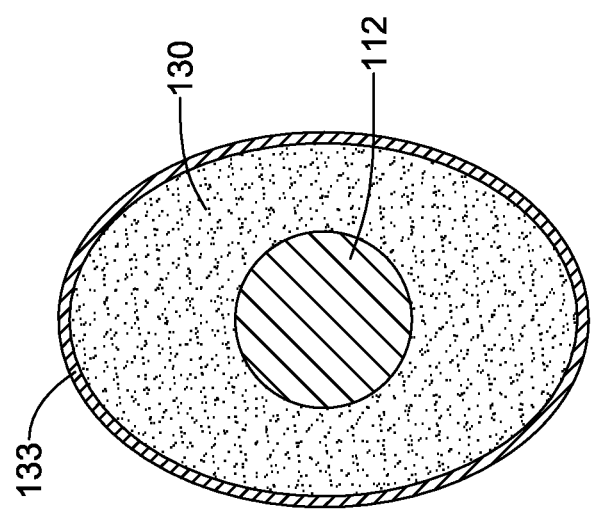
FIG. 4C is a cross-sectional view of the epicardial clip of FIG. 4A taken along line 4C-4C.

As shown in FIG. 4C, which is a cross-section of the clip 110 through line 4C-4C of FIG. 4A, the clip 110 includes a curved member 112 surrounded by or encased within an outer covering 130. In some embodiments, the outer covering 130 may cover one or more of the anterior segment 20, the posterior segment 24 and/or the lateral segment 22. For example, the outer covering 130 may cover the posterior segment 24 and the lateral segment 22, while the anterior segment 20 is not encased with the outer covering 130. In some embodiments the outer covering 130 may be an atraumatic, bioabsorbable and/or biocompatible covering. For example, in some embodiments the outer covering 130 may be a compliant material, for example a polymeric over-mold, such as a silicone over-mold. The outer covering 130, which may be at least partially formed of a compliant material, may more evenly distribute stresses from the member 112 to the surface of the heart, prevent lateral motion of the clip 110 positioned on the heart, and/or provide an area for securing the clip 110 to the heart. For instance, in some embodiments the outer covering 130 may distribute clamping forces to avoid occluding arteries and/or veins on the myocardium and/or epicardium. In some embodiments the outer covering 130 may provide sufficient torsional flexibility, allowing the clip 110 to conform to the contours of the heart.

The outer covering 130 may include a rounded or bulbous section 132 on the anterior segment 120, and a flat section 134 on the posterior segment 124. The bulbous section 132 may prevent lateral motion of the clip 110 when positioned on the heart and may distribute stresses more uniformly in the transverse sinus, as discussed later herein. In some embodiments the anterior segment 120, including the bulbous section 132, may be shaped to preserve the hemodynamics of the great vessels (e.g., aorta, pulmonary trunk, superior vena cava) and aid in retention of the anterior segment 120 in the transverse sinus. The flat section 134 may form to the contours of the heart and/or may more uniformly distribute forces exerted by the clip 110 on the posterior of the heart. For example, the flat section 134 may conform around vessels on the epicardial surface of the heart to avoid occluding the vessels.

Also shown in FIG. 4C, in some embodiments the outer covering 130 may include and/or be wrapped in a fabric sheath 133. For example, in some embodiments the fabric sheath 133 may be an ePTFE material, a polyester knitted fabric, a polyester velour, a polypropylene felt, a woven or braided fabric, a non-woven fabric, porous material, or other textile material, as desired. The fabric sheath 133 may promote tissue in-growth on the epicardial surface of the heart, may provide tissue in-growth into interstices of the fabric sheath 133, and/or provide adequate frictional forces (traction) to hold the clip 110 in contact with the heart and prevent migration of the device once positioned on the heart. Tissue in-growth therein and/or thereon may provide long-term retention of the clip 110 in a desired position on the heart and prevent erosion.

In some embodiments, the clip 110 may include a drug eluting coating in addition to or as an alternative to the outer covering 130. The drug eluting coating may a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, anti-proliferative agents such as steroids, vitamins and restenosis inhibiting drugs, such as Taxol®, paclitaxel (i.e., paclitaxel, paclitaxel analogues, or paclitaxel derivatives, and mixtures thereof).

FIGS. 4A and 4B are a top view and a side view, respectively, of the clip 110 in the same orientation as that of the clip 10 shown in FIGS. 2A and 2B. Thus, as can be seen in FIG. 4A, the clip 110 may have a substantially U-shape or C-shape. In some embodiments, the distance across the clip 10 between the anterior segment 120 and the posterior segment 124 is closest between the first end 114 of the member 112 and the second end 116 of the member 112. The distance between the first end 114 and the second end 116 may determine the final anterior-posterior diameter of the mitral valve.

As shown in FIG. 4B, the anterior segment 120 may lie in an imaginary plane and the posterior segment 124 may lie in an imaginary plane. The imaginary plane of the posterior segment 124 may be located at an acute angle θ to the imaginary plane of the anterior segment 120. The geometry, such as helical geometry, of the lateral segment 122 may control the angle θ between the anterior segment 120 and the posterior segment 124. Thus, the curvature, such as a helical curvature, of the lateral segment 122 may ensure that the anterior segment 120 is properly positioned in the transverse sinus while the posterior segment 124 is properly positioned on the posterior of the heart, such as on or inferior to the atrioventricular groove or in the oblique sinus of the heart.

Figure 5:
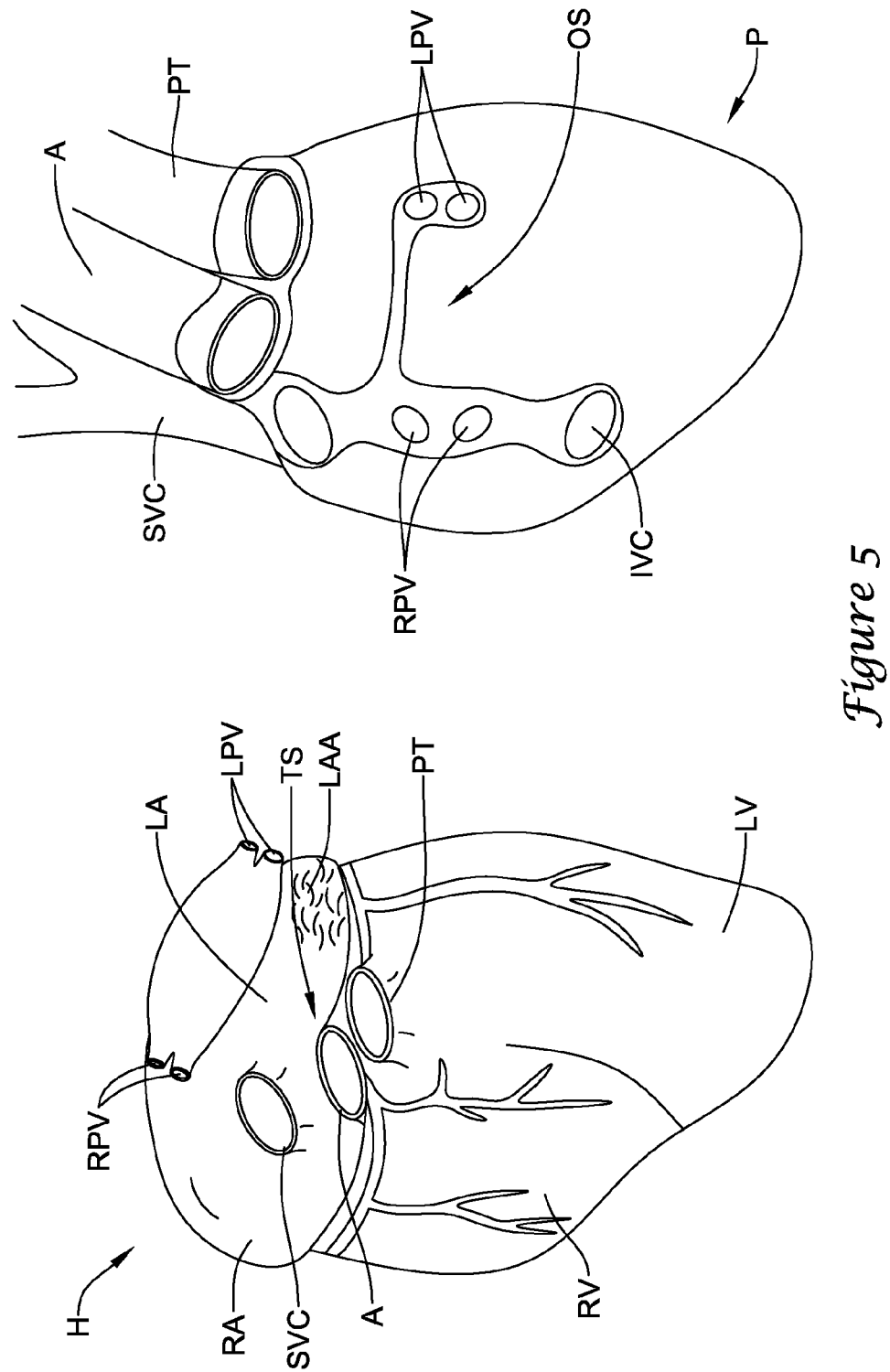
FIG. 5 is an illustration of select anatomical features of a heart.

A heart H, illustrated as a human heart, is shown in FIG. 5. The heart H is viewed from the anterior side at a slightly superior position. The chambers of the heart H include the left ventricle LV, the left atrium LA, the right ventricle RV, and the right atrium RA. Also shown are the pulmonary trunk PT, the aorta A, the superior vena cava SVC, the right pulmonary veins RPV, the left pulmonary veins LPV, and the left atrial appendage LAA. The transverse sinus TS is also referenced in FIG. 5. The transverse sinus TS is a pericardial cavity between the pericardium P and the epicardial surface of the heart H located posterior to the aorta A and the pulmonary trunk PT and anterior to the left atrium and the superior vena cava SVC.

The pericardial sac or pericardium P, which is a tissue membrane covering the epicardial surface of the heart H, is also shown removed from the heart H in FIG. 5 to further illustrate noteworthy anatomy of the heart H. The oblique sinus OS is a blind (e.g., cul-de-sac) recess on the posterior of the heart H formed between the pericardium P and the epicardial surface of the heart H. The oblique sinus OS lies generally between the right pulmonary veins and RPV and the left pulmonary veins LPV, with the thoracic part of the inferior vena cava IVC located to the right of the oblique sinus OS. Only two layers of serous pericardium separate the transverse sinus TS and the oblique sinus OS.

The clip 10 may be positioned on the epicardial surface of the heart H during a medical procedure. For example, in some embodiments the clip 10 may be installed on the heart H during a beating heart surgery, without the need of a heart/lung bypass machine. For instance, the clip 10 may be implanted on the heart H through an open chest procedure (sternotomy) or a lateral thorocotomy. In some embodiments, the clip 10 may be positioned on the heart H through a less-invasive endoscopic approach.

For instance, during a sternotomy, the thoracic cavity may be accessed for direct visual placement of the clip 10 on the beating heart H. The pericardium P may be incised to access the pericardial cavity between the pericardium P and the epicardial surface of the heart H. Upon accessing the pericardial cavity, the clip 10 may be properly positioned on the epicardial surface of the heart H. The anterior segment 20 may be positioned in the transverse sinus TS posterior to the aorta A and the pulmonary trunk PT and anterior to the left atrium and the superior vena cava SVC. Thus, the first end 14 of the member 12 may be located in the transverse sinus TS. The posterior segment 24 may be positioned on the posterior side of the heart H, such as on or inferior to the atrioventricular groove AVG (shown in FIG. 6B) or in the oblique sinus OS. Thus, the second end 16 of the member 12 may be located on or inferior to the atrioventricular groove AVG or in the oblique sinus OS. In some embodiments, the posterior segment 24 may be positioned inferior to the atrioventricular groove on the posterior side of the heart H. The lateral segment 22 may extend around the left lateral side of the heart H such that the anterior segment 20 is properly positioned in the transverse sinus TS while the posterior segment 24 is properly positioned on the posterior side of the heart H, such as on or inferior to the atrioventricular groove AVG or in the oblique sinus OS. In some embodiments, the lateral segment 22 may extend around the heart H at a location inferior to the left atrial appendage LAA. However, in other embodiments the lateral segment 22 may extend around the heart H at a location superior to the left atrial appendage LAA or over the left atrium LA to join the anterior segment 20 and the posterior segment 24.

The clip 10, when properly positioned, may reside on the epicardial surface of the heart H, interior of the pericardium P. Thus, positioning of the clip 10 may not require penetration of the heart into one or more of the chambers of the heart and/or may not require the clip 10 to come into contact with blood being located inside the chambers of the heart. By placing the clip 10 on the epicardial surface, exterior of the interior of the heart H, complications associated with surgical procedures in which access is required to one or more of the chambers of the heart H are avoided. Furthermore, the time required to complete the surgical procedure may be greatly reduced from the time required for an open heart surgery or a surgical procedure requiring accessing the heart through the vasculature.

In some embodiments, the distance between the first end 14 and the second end 16 of the member 12 may be altered during the medical procedure in order to adjust the coaptation of the leaflets of the mitral valve MV. By adjusting the distance between the first end 14 and the second end 16 of the member 12, or otherwise adjusting the curvature of the member 12, the amount of force applied to the walls of the heart H may be varied to attain the response on the mitral valve MV desired. In some embodiments, a sizing device may initially be used to determine the desired curvature of the clip 10, and then a clip 10 of the proper curvature may be chosen, or the clip 10 may be formed to the proper curvature to attain the desired results to the mitral valve MV. Echocardiographic images may be taken to determine the optimal or desired position and/or curvature of the clip 10.

Figure 6A:
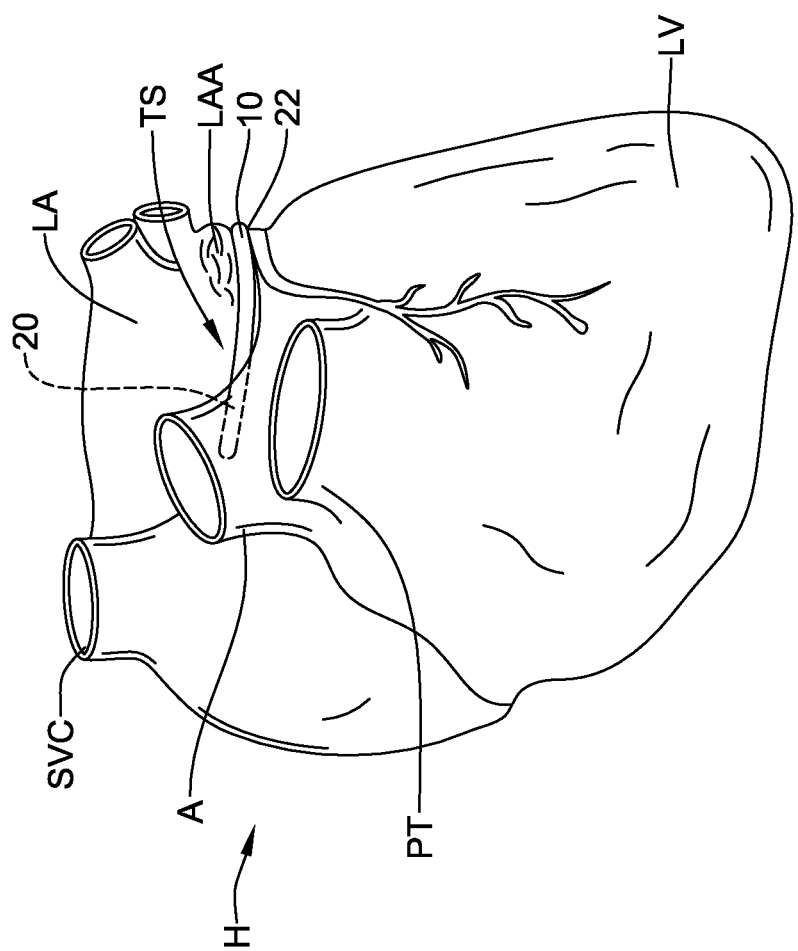
FIG. 6A is an anterior view of a heart showing an exemplary position of an epicardial clip.

FIG. 6A is an anterior view of the heart H, with the clip 10 placed on the epicardial surface of the heart H. As shown in FIG. 6A, the anterior segment 20 of the clip 10 is positioned in the transverse sinus TS posterior to the aorta A and the pulmonary trunk PT and anterior to the left atrium and the superior vena cava SVC. The lateral segment 22 may extend around the left lateral side of the heart H at a location inferior to the left atrial appendage LAA. In other embodiments, the lateral segment 22 may extend around the left lateral side of the heart H at a location superior to the left atrial appendage LAA or over the left atrium LA.

Figure 6B:
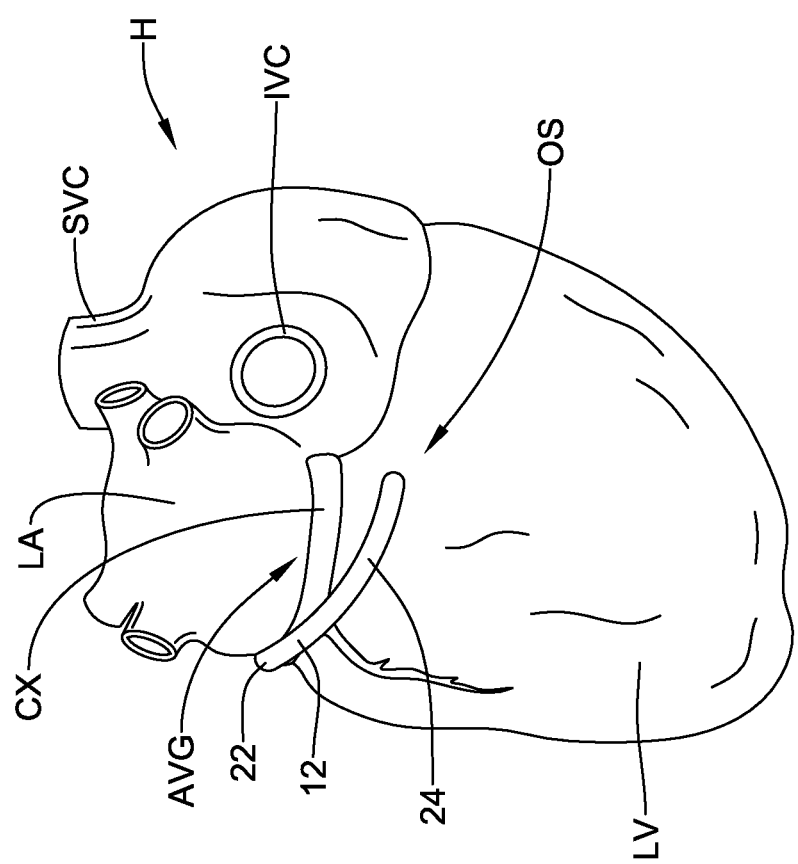
FIG. 6B is a posterior view of a heart showing an exemplary position of an epicardial clip.

FIG. 6B is a posterior view of the heart H with the clip 10 placed on the epicardial surface of the heart H. As shown in FIG. 6B, the posterior segment 24 of the clip 10 is positioned on the posterior of the heart H inferior of the atrioventricular groove AVG. The posterior segment 24 may be positioned such that it is just below the circumflex artery CX. In other embodiments, the posterior segment 24 may be positioned such that it is just above the circumflex artery CX.

When the clip 10 is properly positioned with the anterior segment 20 located in the transverse sinus TS and the posterior segment 24 located in the oblique sinus OS, the clip 10 may apply an inward pressure on the walls of the heart H. The inward pressure exerted by the clip 10 may alter the geometry of the annulus of the mitral valve located between the left atrium LA and the left ventricle LV, thus reducing the anterior-posterior distance across the mitral valve MV and/or the septal-lateral distance across the mitral valve MV. The proper inward pressure may be determined, for example with echocardiographic images, to optimize the functionality of the mitral valve MV to reduce or eliminate mitral regurgitation.

Figure 7:
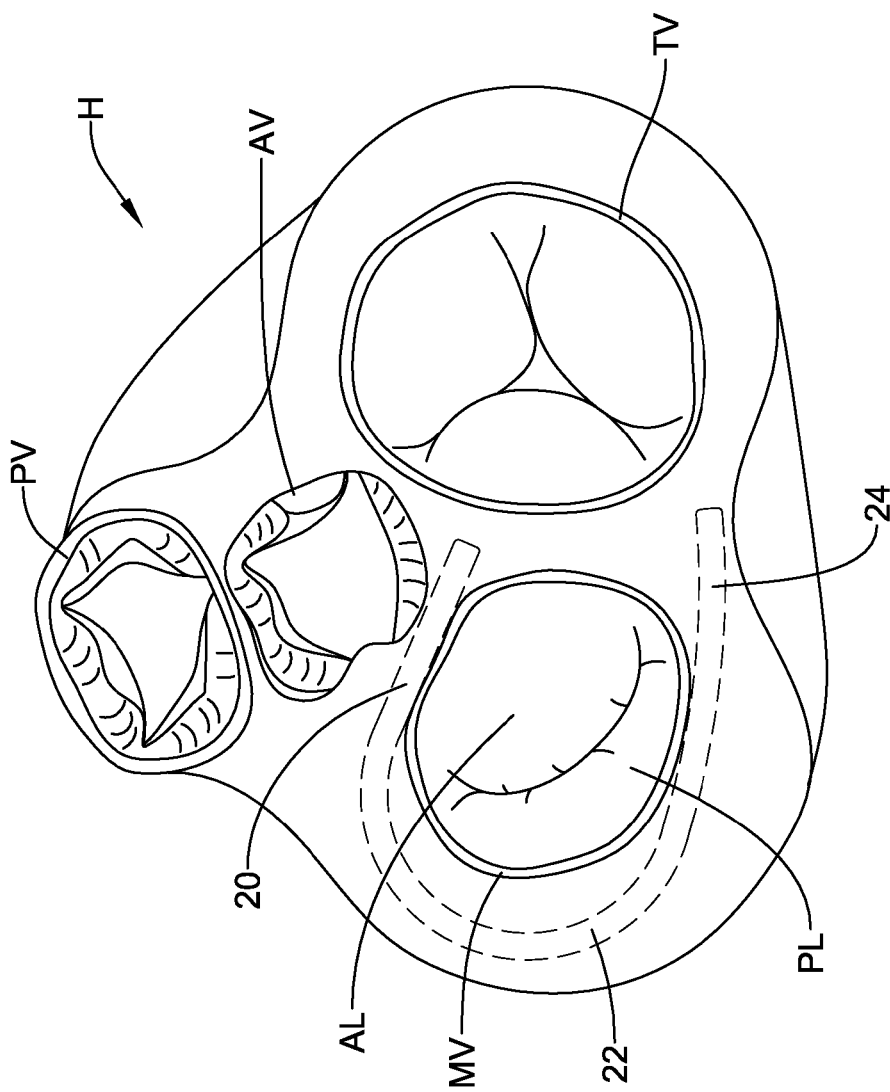
FIG. 7 is a top view of the ventricular portion of a heart with the atria removed illustrating an exemplary position of an epicardial clip.

FIG. 7 is a top view of the ventricular portion of the heart H with the atria removed. With the atria removed, the mitral valve MV between the left atrium LA and the left ventricle LV may be clearly viewed. FIG. 7 also shows the tricuspid valve TV between the right atrium RA and the right ventricle RV, as well as the aortic valve AV leading to the aorta A and the pulmonary valve PV leading to the pulmonary trunk PT. As shown in FIG. 7, the mitral valve MV includes two leaflets, an anterior leaflet AL and a posterior leaflet PL. The mitral valve MV is shown closed as it would be during systole. The clip 10 is shown in dashed lines in FIG. 8 as the clip 10 may not lie in the plane of the mitral valve MV.

As shown in FIG. 7, when the clip 10 is properly placed around the heart, the shape of the clip 10 may reduce the anterior-posterior measurement of the mitral valve MV. In other words, the clip 10 may urge the posterior leaflet PL of the mitral valve MV toward the anterior leaflet AL, providing better contact (coaptation) of the anterior and posterior valve leaflets of the mitral valve MV, which may reduce or eliminate mitral regurgitation. For instance, the posterior segment 24 of the clip 10 may push on the ventricular wall of the left ventricle LV to alter the diameter of the annulus of the mitral valve MV. Thus, as shown in FIG. 7, the inclusion of the clip 10 may allow the posterior leaflet PL to more fully contact the anterior leaflet AL during systole to reduce or prevent retrograde blood flow through the mitral valve MV, thereby increasing the efficiency of the heart. During a medical procedure, echocardiographic images may be taken to determine the optimal or desired position and/or curvature of the clip 10 to attain the proper anterior-posterior measurement (distance) and/or septal-lateral measurement (distance) of the annulus of the mitral valve MV to minimize and/or eliminate mitral regurgitation.

Figure 8A:
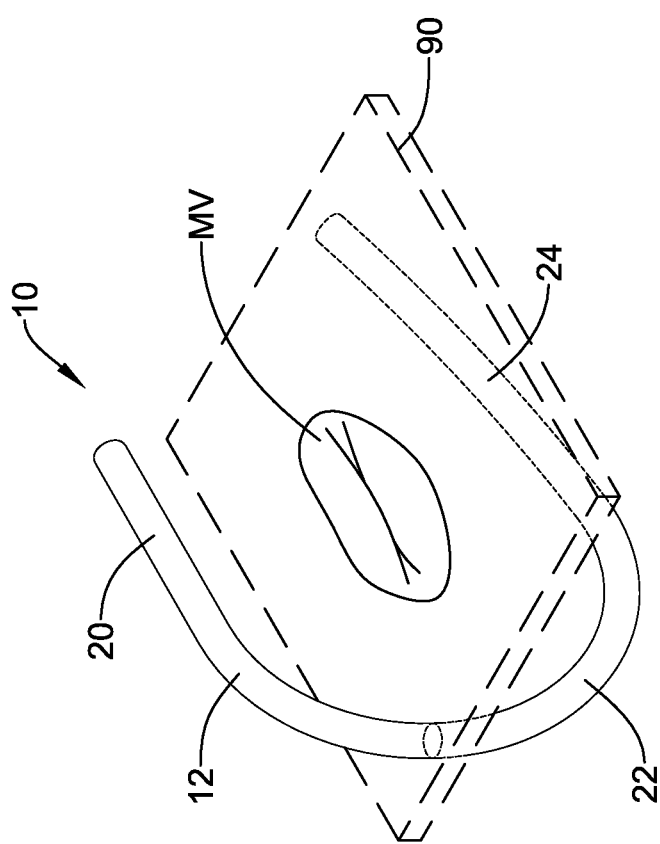
FIGS. 8A-8C are illustrative views showing the orientation of the plane of the mitral valve relative to the position of the epicardial clip on a heart.
Figure 8B:
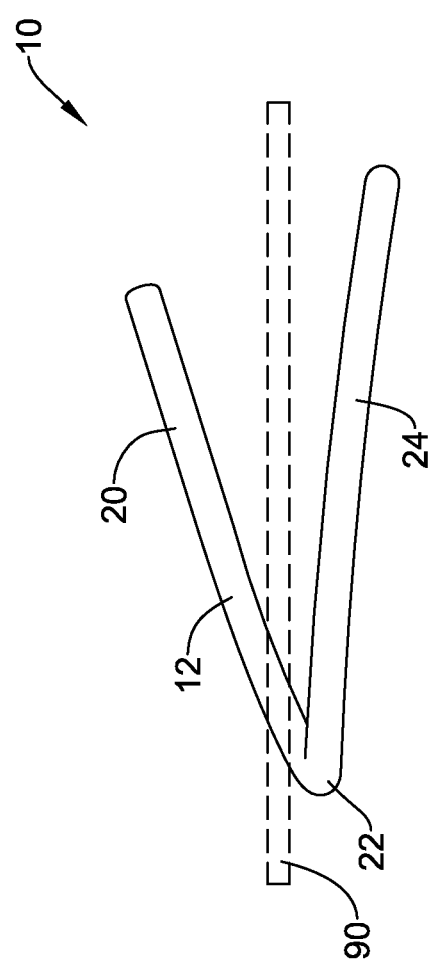
Figure 8C:
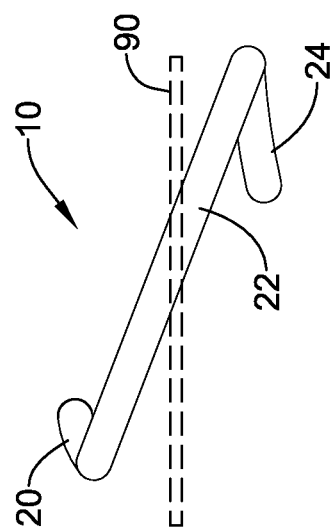
Figure 9:
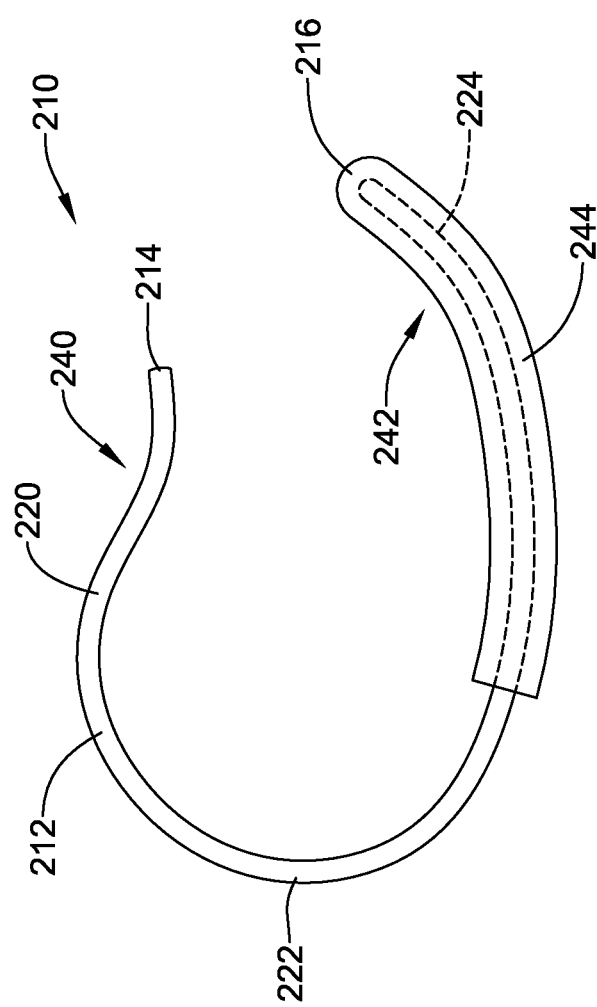
FIGS. 9-15 show further embodiments and alternative configurations of exemplary epicardial clips.

FIGS. 8A-8C show the clip 10 as oriented with the plane of the mitral valve MV when the anterior segment 20 of the clip 10 is positioned in the transverse sinus TS and the posterior segment 24 of the clip 10 is positioned on the posterior side of the heart, such as on or inferior to the atrioventricular groove. As mentioned previously, the mitral valve MV lies in an imaginary plane which is shown in FIGS. 8A-8C as plane 90. When positioned on the epicardial surface of the heart H, the anterior segment 20 extends above the plane of the mitral valve MV and the posterior segment 24 extends below the plane of the mitral valve MV. Thus, neither the anterior segment 20 nor the posterior segment 24 lies in the same plane as the mitral valve MV. Furthermore the imaginary line between the first end 14 of the clip 10 and the second end 16 of the clip 10 does not lie in the plane of the mitral valve MV. As shown in FIGS. 8A-8C, the plane of the mitral valve MV intersects the lateral segment 22 of the clip 10.

Further embodiments of alternative configurations of epicardial clips with various modifications and additional features are shown in FIGS. 9-15. The epicardial clip 210 shown in FIG. 9 includes an additional or secondary curve 240 in the anterior segment 220 of the curved member 212. The secondary curve 240 may curve anteriorly in order to extend out around the aorta A when the anterior segment 220 is positioned in the transverse sinus TS posterior to the aorta A. Thus, the secondary curve 240 may aid in greater device stability and/or retention in the transverse sinus TS, preventing migration of the clip 210 during the use of the clip 210 on the heart H.

The epicardial clip 210 also includes a tighter curve 242 (e.g. a radius of curvature less than the radius of curvature of the remainder of the posterior segment 224) in the posterior segment 224 of the member 212. The curve 242 is located at the second end 216 of the member 212. The curve 242 increases the inward force on the ventricular wall in this region to provide an extra push in the A3-P3 region of the mitral valve MV.

The epicardial clip 210 is shown with a pad 244 disposed over at least a portion of the posterior segment 224. The pad 244 may help distribute forces from the epicardial clip 210 over a larger portion of the ventricular wall of a heart. For example, the pad 244 of the epicardial clip 210 may prevent or reduce contact forces being applied to a vessel located on the epicardial surface of the heart.

Figure 10:
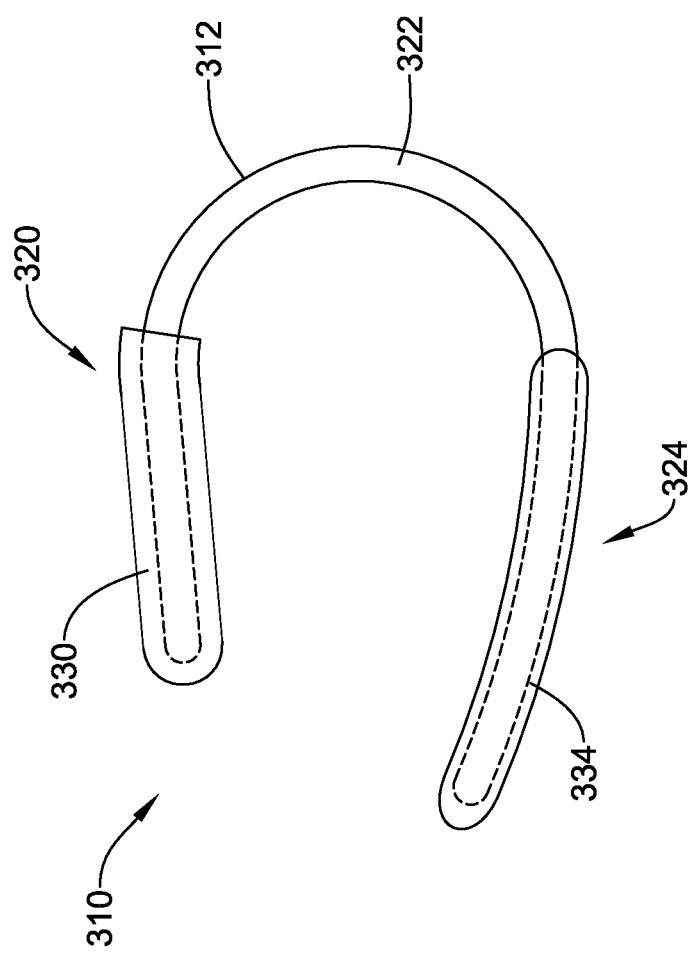

The epicardial clip 310 shown in FIG. 10 includes an anterior segment 320, a posterior segment 324 and a lateral segment 322 between the anterior segment 320 and the posterior segment 324. The epicardial clip 310 also includes an anterior pad 330 positioned over the anterior segment 320 of the member 312, and a posterior pad 334 positioned over the posterior segment 324 of the member 312. The anterior pad 330 may help retain the anterior segment 320 in the transverse sinus and prevent migration of the clip 310. The posterior pad 324, which may be a flat pad in some embodiments, may distribute forces over a greater area of the ventricular wall without occluding vessels in the myocardium.

Figure 11:
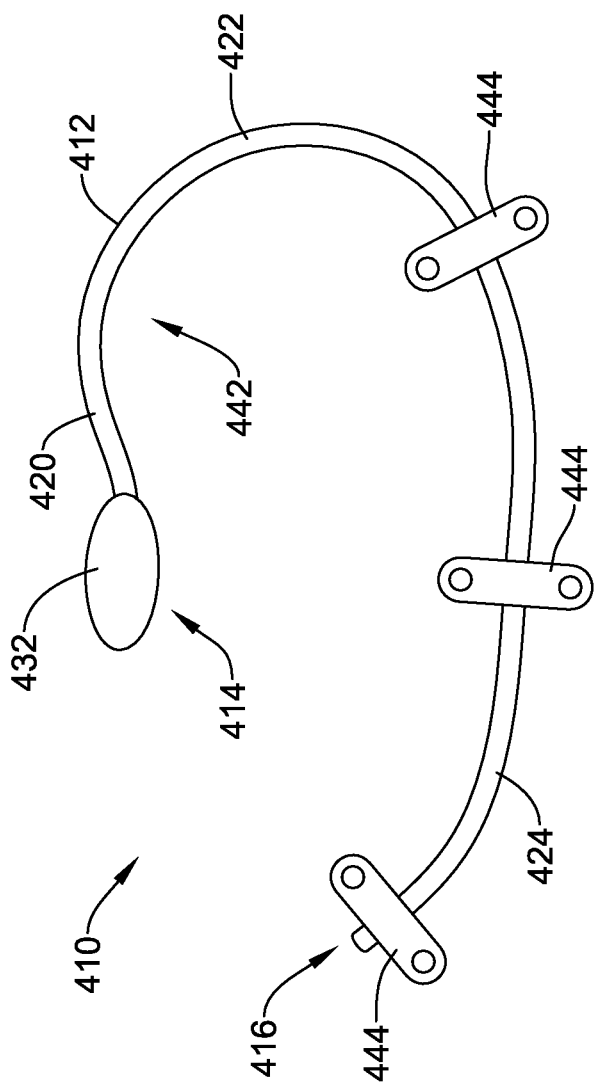

The epicardial clip 410 shown in FIG. 11 includes an anterior segment 420 proximate a first end 414 of the member 412, a posterior segment 424 proximate a second end 416 of the member 412, and a lateral segment 422 between the anterior segment 420 and the posterior segment 424. The epicardial clip 410 also includes three posterior pads 444 located at spaced intervals along the posterior segment 424 of the member 412. The posterior pads 444 may include apertures for receiving sutures, fasteners or tissue anchors, such that the posterior pads 444 may be sutured or anchored to the ventricular wall of the heart.

The epicardial clip 410 also includes a bulbous tip 432 on the anterior segment 420 at the first end 414 of the member 412. The bulbous tip 432 may be shaped to preserve the hemodynamics of the great vessels (e.g., aorta, pulmonary trunk, superior vena cava) and aid in retention of the anterior segment 420 in the transverse sinus.

Furthermore, the epicardial clip 410 includes a tighter curve 442 located between the anterior segment 420 and the lateral segment 422. The curve 442 may have a radius of curvature less than the radius of curvature of the lateral segment 422. The curve 442 increases the inward force on the atrial wall in this region to provide an extra push in the A1-P1 region of the mitral valve.

Figure 12:
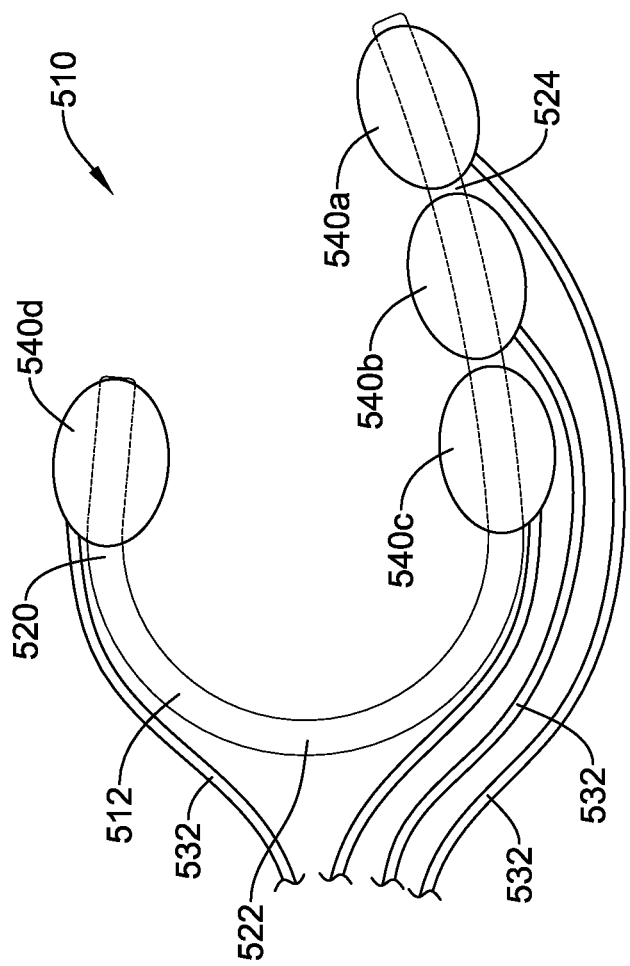

The epicardial clip 510 shown in FIG. 12 includes an anterior segment 520, a posterior segment 524, and a lateral segment 522 between the anterior segment 520 and the posterior segment 524. The epicardial clip 510 also includes a plurality of balloons 540 positioned on the member 512. The balloons 540 may be selectively inflated to provide a desired amount of force at desired locations of the epicardial surface of the heart. In some embodiments, the balloons 540 may each be individually or collectively inflated to a desired size. In some embodiments, the balloons 540 may be independently, simultaneously, and/or successively inflated. The balloons 540 may be inflated by one or more conduits 532 which may be permanently attached to the balloons 540, or the one or more conduits 532 may be detachable from the balloons 540 upon proper inflation of the balloons 540.

The balloons 540 may provide an inward force at a desired location to provide better coaptation of the valve leaflets. For instance, the posterior segment 524 may include three balloons 540. The balloon 540a may provide a desired inward push in the A3-P3 region of the mitral valve, the balloon 540b may provide a desired inward push in the A2-P2 region of the mitral valve, and the balloon 540c may provide a desired inward push in the A1-P1 region of the mitral valve. The balloon 540d on the anterior segment 520 may also provide a desired push in the A1-P1 region and/or the balloon 540d may aid in retaining the anterior segment 520 in the transverse sinus.

Figure 13:
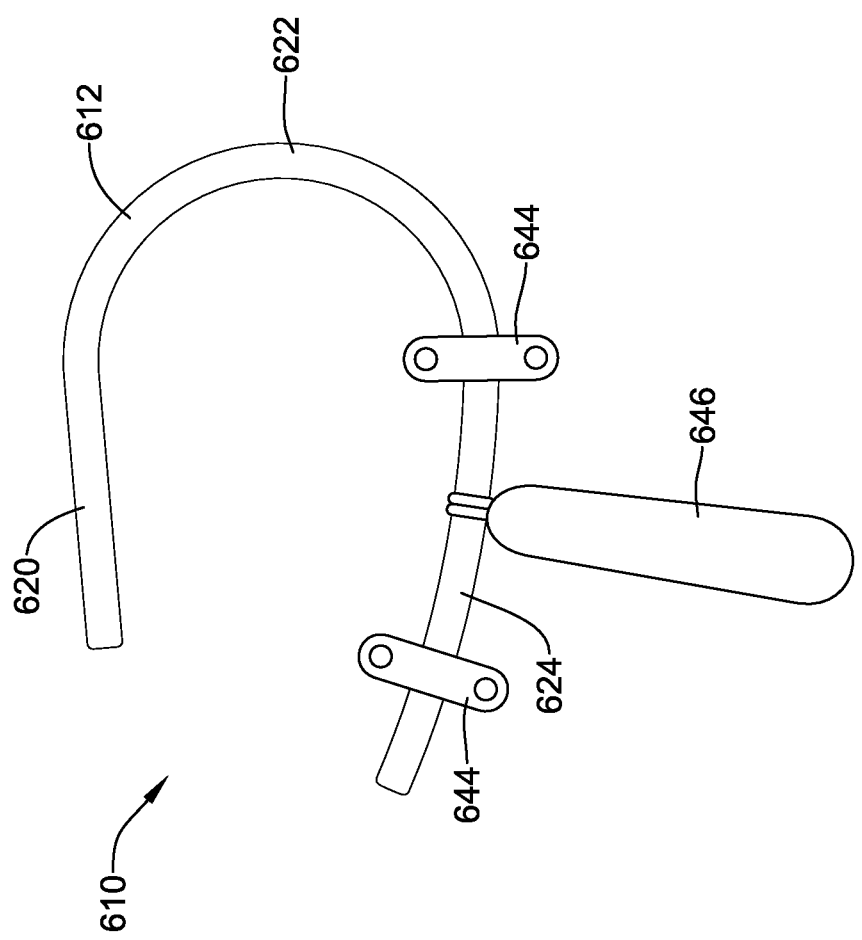

The epicardial clip 610 shown in FIG. 13 includes an anterior segment 620, a posterior segment 624, and a lateral segment 622 between the anterior segment 620 and the posterior segment 624. The epicardial clip 610 also includes an arm 646 extending from the member 612. When the epicardial clip 610 is properly positioned around the heart, the arm 646 may push inward on the ventricular wall, exterior of the papillary muscles of the left ventricle, to reduce the distance between the papillary muscles in order to improve coaptation of the leaflets of the mitral valve. In other embodiments, the epicardial clip 610 may include one or more additional arms for pushing inward on the papillary muscles. For example an embodiment having two arms 646 may be used to squeeze or push the papillary muscles in the left ventricle toward each other.

The pads 644 connected to the member 612 may also be used to anchor or secure the clip 610 to the epicardial surface of the heart. For instance, the clip 610 may be sutured or anchored with tacking screws, or the like, to the myocardium to retain the clip 610 in a proper orientation around the heart.

Figure 14:
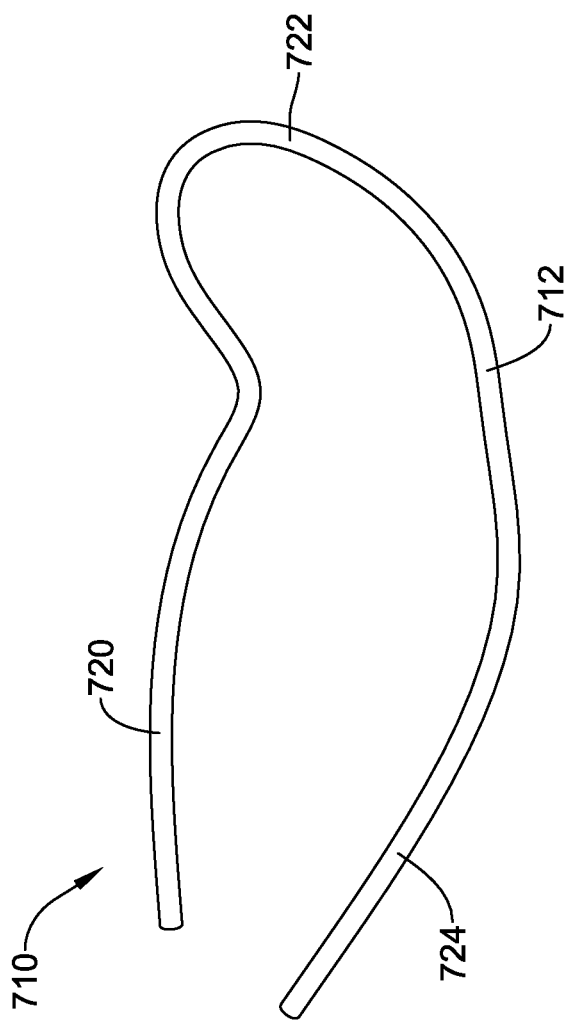

Another embodiment of an epicardial clip 710 is shown in FIG. 14. The epicardial clip 710 is formed of a member 712 having an anterior segment 720, a posterior segment 724, and a lateral segment 722 intermediate the anterior segment 720 and the posterior segment 724. The lateral segment 722 is bent relative to both the anterior segment 720 and the posterior segment 724. Thus, the lateral segment 722 may lie in a plane dissimilar to the plane of the anterior segment 720 and the plane of the posterior segment 724. The shape of the lateral segment 722 may allow the lateral segment 722 to be stabilized on a lateral portion of the ventricular wall of a heart.

Figure 15:
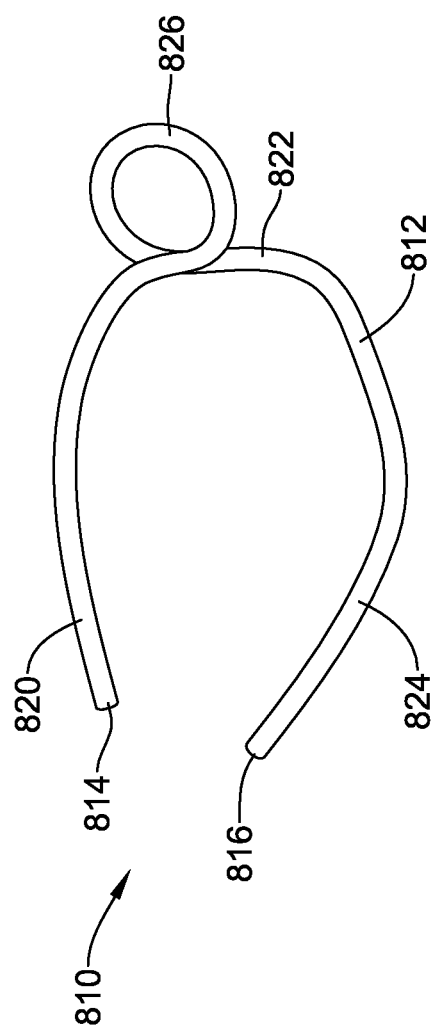

Another epicardial clip 810 is shown in FIG. 15. The epicardial clip 810 is formed of a member 812 having an anterior segment 820, a posterior segment 824, and a lateral segment 822 intermediate the anterior segment 820 and the posterior segment 824. As shown in FIG. 15, the lateral segment 822 includes a spring-like helical loop 826 providing the clip 810 with a springy quality which allows the member 812 to recover its original shape when released after being distorted by an applied force. Thus, the ends 814 and 816 of the member 812 may be forced away from each other during insertion of the clip 810 on the heart, but the spring nature of the helical loop 826 tends to draw the ends 814 and 816 back toward each other when the applied force is removed from the member 812.

Figure 16:
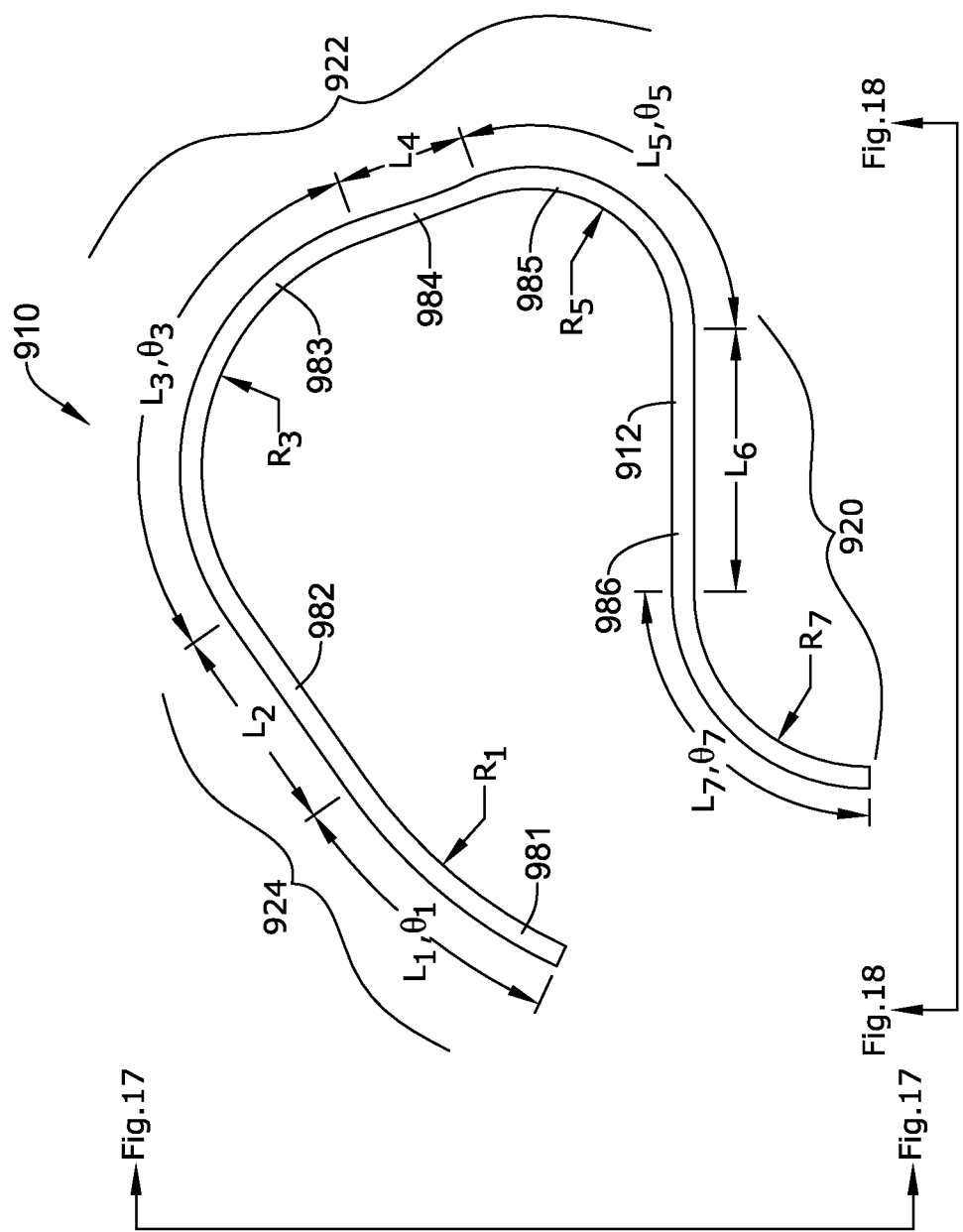
FIG. 16 is a top view of another exemplary epicardial clip.

FIG. 16 is a top view of another configuration of an epicardial clip 910. The epicardial clip 910, as shown in FIG. 16 is positioned as it would appear to an observer looking down on a heart on which the epicardial clip 910 is placed, from a superior position. The epicardial clip 910 is formed of a member 912 having an anterior segment 920, a posterior segment 924, and a lateral segment 922 intermediate the anterior segment 920 and the posterior segment 924. The anterior segment 920 is configured to be positioned on an anterior portion of the heart, the posterior segment 924 is configured to be positioned on a posterior portion of the heart, and the lateral segment 922 is configured to be positioned on a lateral portion of the heart. For example, when properly positioned on the epicardial surface of a heart, the anterior segment 920 may be positioned in the transverse sinus, the posterior segment 924 may be positioned on the posterior side of the heart, such as on or inferior to the atrioventricular groove or in the oblique sinus, and the lateral segment 922 may extend around the lateral side of the heart in order to allow proper placement of the anterior segment 920 and the posterior segment 924.

The epicardial clip 910 may include a plurality of sections. As shown in FIG. 16, the epicardial clip 910 includes seven sections, however, other numbers and/or configurations of sections are contemplated. In some embodiments, the sections of the epicardial clip 910 may be alternating sections of curved portions and straight portions of the epicardial clip 910. The epicardial clip 910, as shown in FIG. 16, includes a first section 981 and a second section 982, which may span the posterior segment 924 of the epicardial clip 910. The first section 981 may be a curved section having a radius of curvature $R_1$ and a length $L_1$ which goes through an angle $\theta_1$. In some embodiments, the radius of curvature $R_1$ of the first section 981 may be in the range of about 1 inch to about 2 inches, about 1.25 inches to about 1.75 inches, or about 1.5 inches, depending on the specific anatomical shape of the heart. The first section 981 may extend through an angle $\theta_1$. In some embodiments, the angle $\theta_1$ may be in the range of about 20° to about 40°, or about 30°. In some embodiments, the length $L_1$ of the first section 981 may be in the range of about 0.5 inches to about 1.5 inches, about 0.75 inches to about 1.0 inches, or about 0.785 inches. The curved nature of the first section 981 may allow it to conform to the curvature of the posterior side of the heart.

The second section 982 may be a straight or substantially straight section having a length $L_2$ in the range of about 0.4 to about 0.8 inches, about 0.5 inches to about 0.7 inches, or about 0.5 inches.

The epicardial clip 910 may also include a third section 983, a fourth section 984 and a fifth section 985, which may span the lateral segment 922 of the epicardial clip 910. The third section 983 may be a curved section having a radius of curvature $R_3$ and a length $L_3$ which goes through an angle $\theta_3$. In some embodiments, the radius of curvature $R_3$ of the third section 983 may be in the range of about 0.25 inch to about 1.5 inches, about 0.5 inches to about 1.0 inches, or about 0.75 inches, depending on the specific anatomical shape of the heart. The third section 983 may extend through an angle $\theta_3$. In some embodiments, the angle $\theta_3$ may be in the range of about 75° to about 130°, about 90° to about 115°, or about 105°. In some embodiments, the length $L_3$ of the third section 983 may be in the range of about 0.5 inches to about 2.0 inches, about 1.0 inches to about 1.5 inches, or about 1.375 inches. The curved nature of the third section 983 may allow it to conform to the curvature of the anterior side of the heart.

The fourth section 984 may be a straight or substantially straight section having a length $L_4$ in the range of about 0.2 to about 0.5 inches, about 0.3 inches to about 0.4 inches, or about 0.375 inches.

The fifth section 985 may be a curved section having a radius of curvature $R_5$ and a length $L_5$ which goes through an angle $\theta_5$. In some embodiments, the radius of curvature $R_5$ of the fifth section 985 may be in the range of about 0.25 inches to about 0.75 inches, about 0.4 inches to about 0.5 inches, or about 0.4625 inches, depending on the specific anatomical shape of the heart. The fifth section 985 may extend through an angle $\theta_5$. In some embodiments, the angle $\theta_5$ may be in the range of about 75° to about 130°, about 90° to about 115°, or about 110°. In some embodiments, the length $L_5$ of the fifth section 985 may be in the range of about 0.5 inches to about 2.0 inches, about 0.75 inches to about 1.0 inches, or about 0.888 inches. The curved nature of the fifth section 985 may allow it to conform to the curvature of the anterior side of the heart.

Additionally, the epicardial clip 910 may include a sixth section 986 and a seventh section 987, which may span the anterior segment 920 of the epicardial clip 910. The sixth section 986 may be a straight or substantially straight section having a length $L_6$ in the range of about 0.5 inches to about 1.0 inches, about 0.6 inches to about 0.8 inches, or about 0.75 inches.

The seventh section 987 may be a curved section having a radius of curvature $R_7$ and a length $L_7$ which goes through an angle $\theta_7$. In some embodiments, the radius of curvature $R_7$ of the seventh section 987 may be in the range of about 0.25 inches to about 0.75 inches, about 0.3 inches to about 0.6 inches, or about 0.5 inches, depending on the specific anatomical shape of the heart. The seventh section 987 may extend through an angle $\theta_7$. In some embodiments, the angle $\theta_7$ may be in the range of about 75° to about 120°, about 80° to about 100°, or about 90°. In some embodiments, the length $L_7$ of the seventh section 987 may be in the range of about 0.5 inches to about 1.25 inches, about 0.6 inches to about 0.8 inches, or about 0.785 inches. The curved nature of the seventh section 983 may allow it to be positioned around a portion of the root of the aorta when the anterior segment 920 is positioned in the transverse sinus of a heart in order to further anchor the epicardial clip 910 in the transverse sinus.

Figure 17:
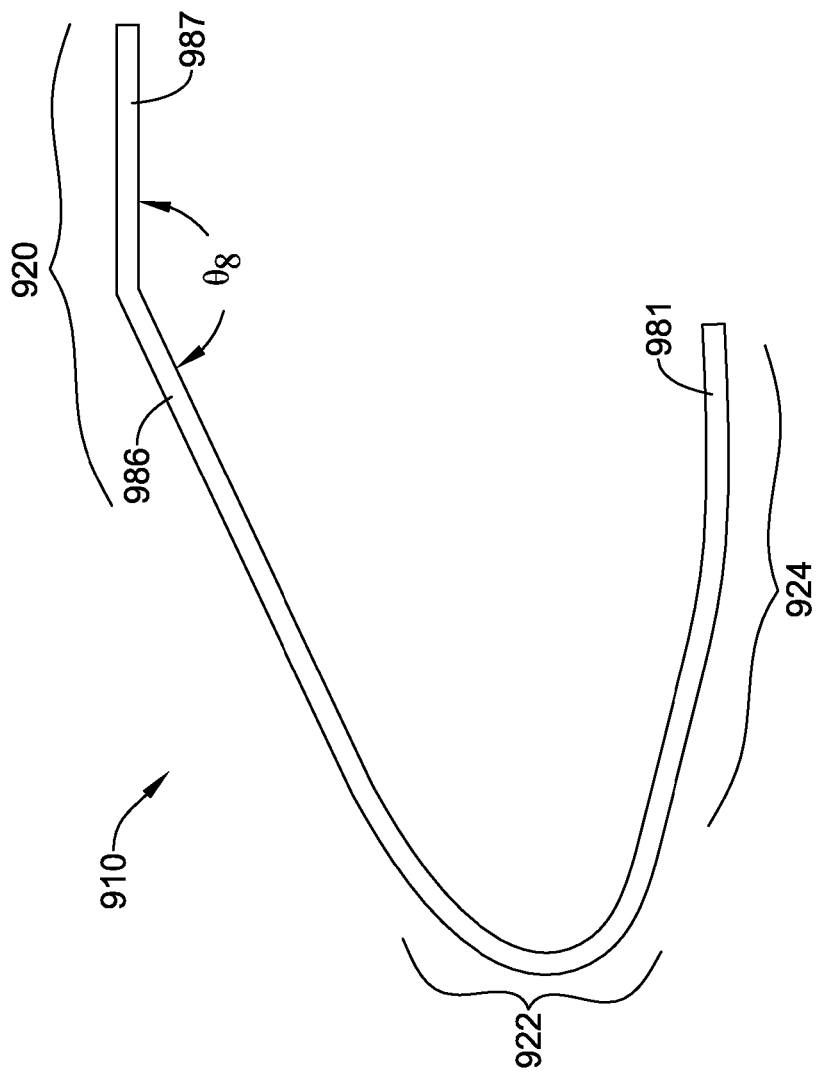
FIG. 17 is a side view of the epicardial clip of FIG. 16 taken along line 17-17.

FIG. 17 is a side view of the epicardial clip 910 taken along the line 17-17 of FIG. 16. As shown in FIG. 17, the epicardial clip 910 may have a helical nature. For instance, the lateral segment 922 may include one or more helical curves such that the anterior segment 920 does not lie in the same plane as the posterior segment 924. For example, the third section 983 and/or the fifth section 985 of the epicardial clip 910 may include a helical curve.

Additionally, as shown in FIG. 17, the seventh section 987 may be at an oblique angle $\theta_8$ to the adjacent sixth section 986. For example, the seventh section 987 may be at an angle $\theta_8$ of about 120° to about 170°, about 130° to about 160°, or about 155° to the sixth section 986. The angle $\theta_8$ may allow the seventh section 987 to reside within the transverse sinus of a heart.

Figure 18:
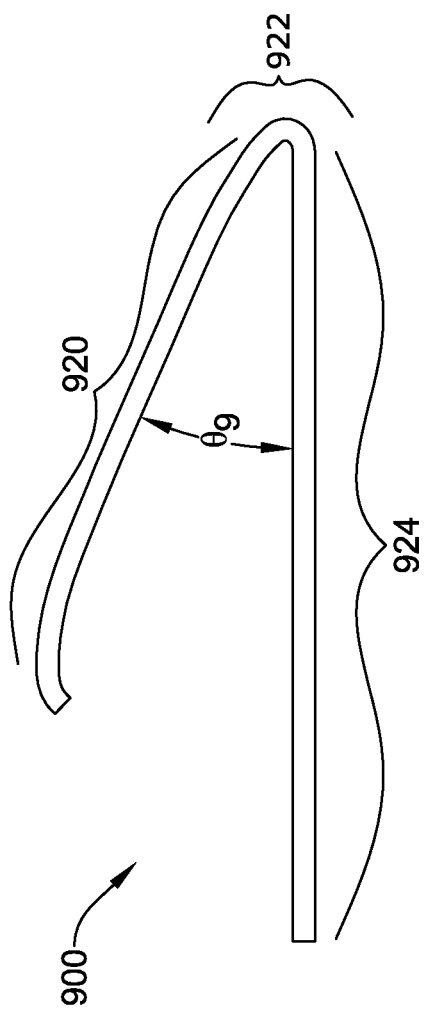
FIG. 18 is a side view of the epicardial clip of FIG. 16 taken along line 18-18.

FIG. 18 is a side view of the epicardial clip 910 taken along the line 18-18 of FIG. 16. As shown in FIG. 18, the anterior segment 920 does not lie in the same plane as the posterior segment 924. For example, the anterior segment 920 may lie in an imaginary plane which is at an angle $\theta_9$ to an imaginary plane in which the posterior segment 924 may lie. For example, the anterior segment 920 may be at an angle $\theta_9$ of about 10° to about 30°, about 20° to about 25°, or about 23.5° to the posterior segment 924. The angle $\theta_9$ may allow the anterior segment 920 to be positioned within the transverse sinus of a heart while allowing the posterior segment 924 to be positioned on the posterior side of the heart, such as on or inferior to the atrioventricular groove or within the oblique sinus of the heart, with the lateral segment 922 extending around a lateral portion of the heart.

Figure 19:
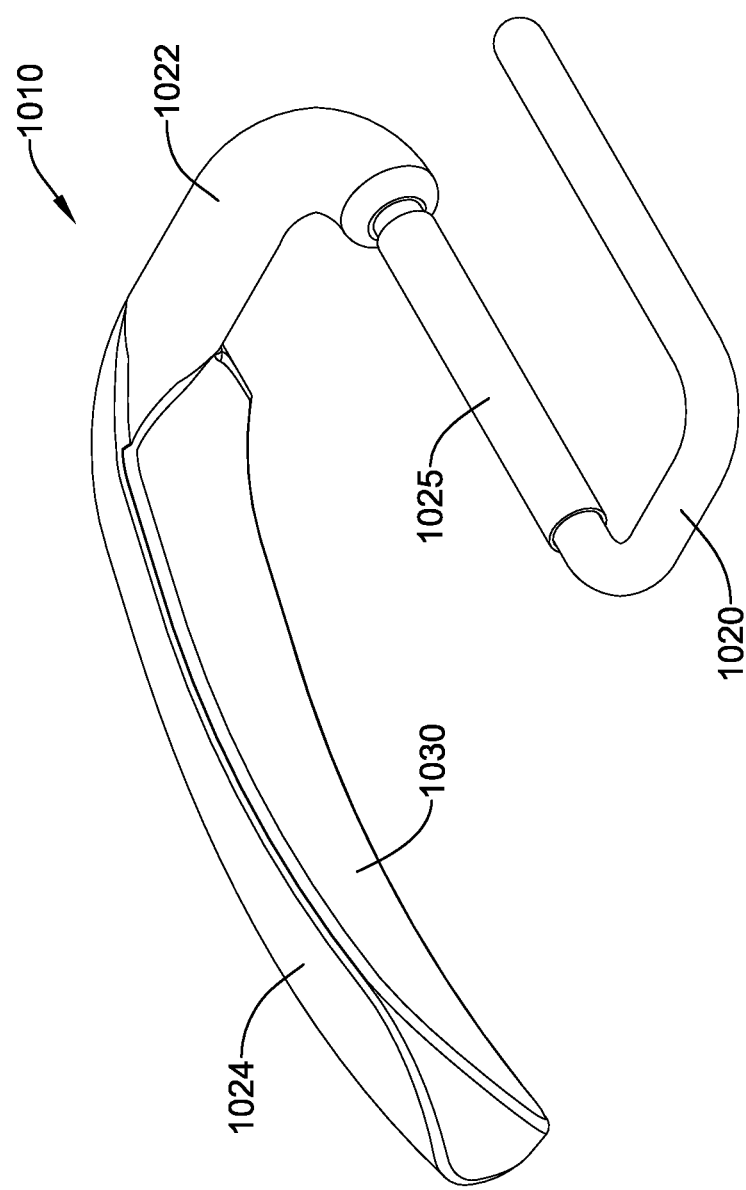
FIGS. 19 and 20 are perspective views of yet another illustrative epicardial clip.
Figure 20:
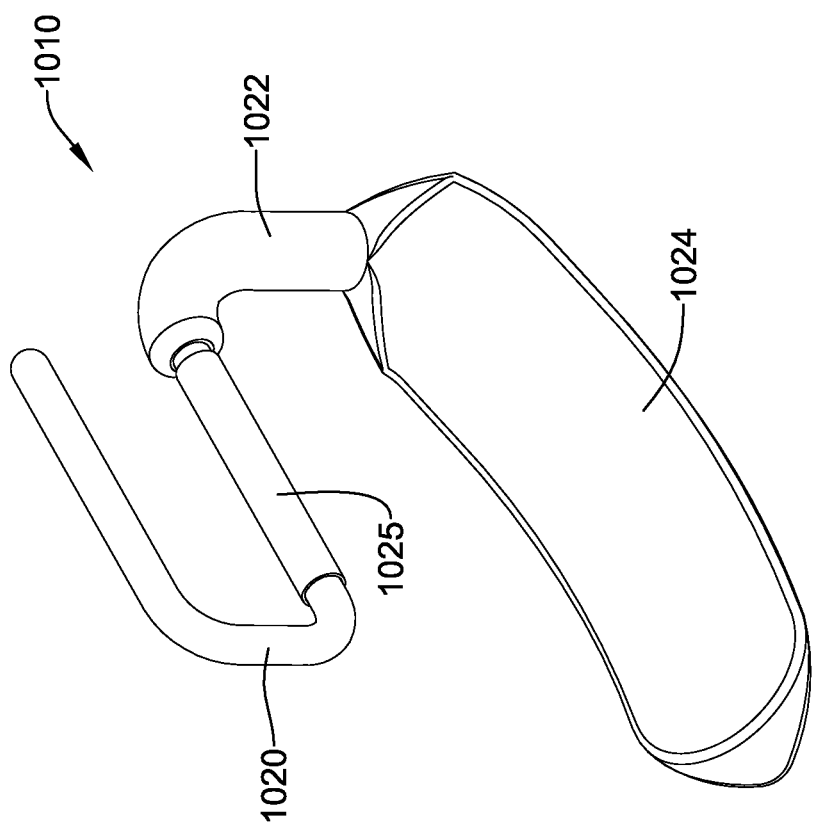

FIGS. 19 and 20 are perspective views of yet another epicardial clip 1010. The epicardial clip 1010 may include an anterior segment 1020, a posterior segment 1024, and a lateral segment 1022 intermediate the anterior segment 1020 and the posterior segment 1024. The anterior segment 1020 is configured to be positioned on an anterior portion of the heart, the posterior segment 1024 is configured to be positioned on a posterior portion of the heart, and the lateral segment 1022 is configured to be positioned on a lateral portion of the heart. For example, when properly positioned on the epicardial surface of a heart, the anterior segment 1020 may be positioned in the transverse sinus, the posterior segment 1024 may be positioned on the posterior side of the heart, such as on or inferior to the atrioventricular groove or in the oblique sinus, and the lateral segment 1022 may extend around the lateral side of the heart in order to allow proper placement of the anterior segment 1020 and the posterior segment 1024.

In some embodiments, the epicardial clip 1010 may include a core member (not shown), such as a wire or rod with an appropriate curvature surrounded by or encased within an outer member 1030. In some embodiments the outer member 1030 may be an atraumatic, bioabsorbable and/or biocompatible covering. For example, in some embodiments the outer member 1030 may be a compliant material, for example a polymeric over-mold, such as a silicone over-mold molded, formed or otherwise placed around an inner core member. In some embodiments, the outer member 1030 may be an irregular shaped member complementary with the contours of a heart. The outer member 1030 may more evenly distribute stresses from the epicardial clip 1010 to the surface of the heart, prevent lateral motion of the clip 1010 positioned on the heart, and/or provide an area for securing the clip 1010 to the heart. For instance, in some embodiments the outer member 1030, such as a silicone over-mold, may distribute clamping forces to avoid occluding arteries and/or veins on the myocardium. In some embodiments the outer member 1030 may provide sufficient torsional flexibility, allowing the clip 1010 to conform to the contours of the heart.

Additionally, although not shown, in some embodiments the outer member 1030 may be wrapped in a fabric covering or sheath. In some embodiments, the fabric covering may be stitched, adhered, clipped or otherwise secured to itself and/or the outer member 1030 to hold the fabric covering in place. For example, in some embodiments the fabric covering may be an ePTFE material, a polyester knitted fabric, a polyester velour, a polypropylene felt, a woven or braided fabric, a non-woven fabric, porous material, or other textile material, as desired. In some embodiments, the fabric covering may promote tissue in-growth on the epicardial surface of the heart, may provide tissue in-growth into interstices of the fabric sheath and/or provide adequate frictional forces (traction) to hold the epicardial clip 1010 in contact with the heart and prevent migration of the device once positioned on the heart. Tissue in-growth therein and/or thereon may provide long-term retention of the epicardial clip 1010 in a desired position on the heart and prevent erosion.

In some embodiments, the epicardial clip 1010 may include a drug eluting coating in addition to or as an alternative to an outer member and/or fabric covering. The drug eluting coating may a controlled release of a therapeutic agent over a specified period of time. The therapeutic agent may be any medicinal agent which may provide a desired effect. Suitable therapeutic agents include drugs, genetic materials, and biological materials. Some suitable therapeutic agents which may be loaded in the drug eluting coating include, but are not necessarily limited to, antibiotics, antimicrobials, antioxidants, anti-arhythmics, cell growth factors, immunosuppressants such as tacrolimus, everolimus, and rapamycin (sirolimus), therapeutic antibodies, wound healing agents, therapeutic gene transfer constructs, peptides, proteins, extracellular matrix components, steroidal and non-steroidal anti-inflammatory agents, anti-proliferative agents such as steroids, vitamins and restenosis inhibiting drugs, such as Taxol®, paclitaxel (i.e., paclitaxel, paclitaxel analogues, or paclitaxel derivatives, and mixtures thereof).

Figure 21:
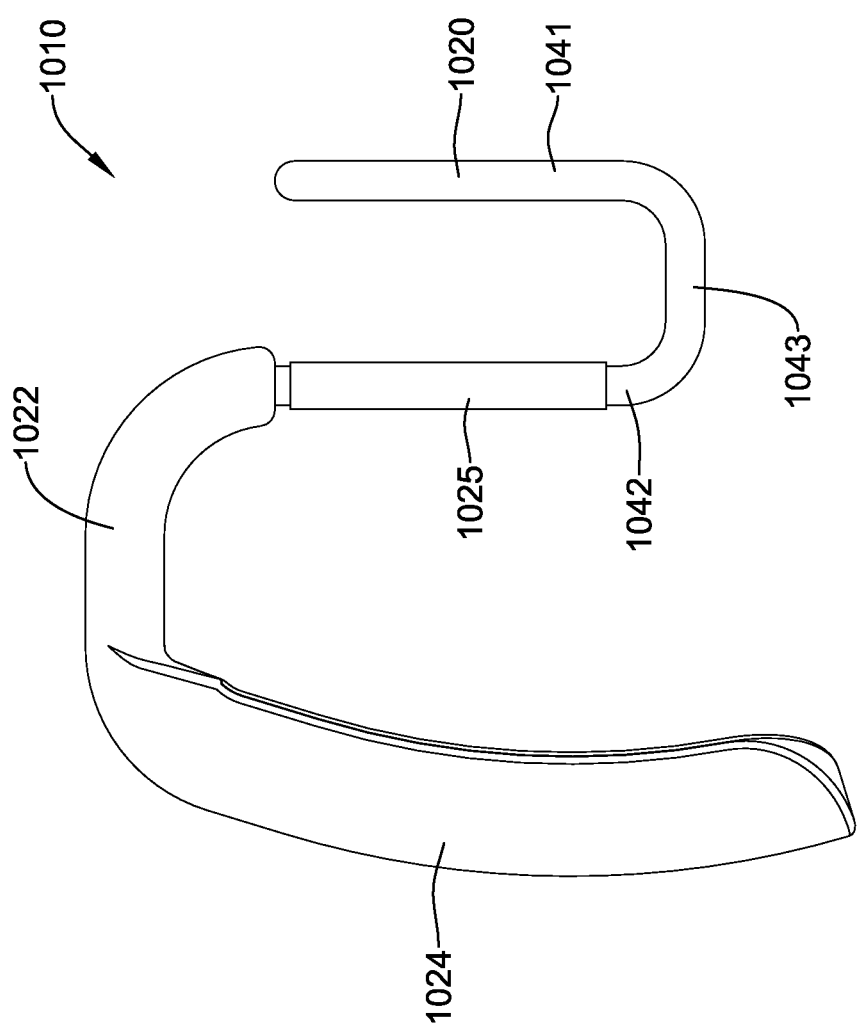
FIG. 21 is a top view of the epicardial clip shown in FIGS. 19 and 20.

As can be seen in FIG. 21, when viewed from above, the epicardial clip 1010 may have a generally U-shape or C-shape. The epicardial clip 1010 may be a one-piece, unitary member, or the epicardial clip 1010 may be formed of two or more discrete elements coupled together. For example, as shown in FIG. 21, the posterior segment 1024 and the lateral segment 1022 may be integrally formed, and the anterior segment 1020 may be coupled to the lateral segment 1022. For instance, the anterior segment 1020 may include a coupling portion or coupler 1025 for coupling the anterior segment 1020 to the lateral segment 1022. In some embodiments the coupling portion 1025 may be a tubular member extending over a portion of the anterior segment 1020 and extending over a portion of the lateral segment 1022.

As shown in FIG. 21, the anterior segment 1020 may include a double-member (e.g., a member that is bent back on itself, forming a U-shape). The double-member of the anterior segment 1020 may be found to provide enhanced retention and/or stability in the transverse sinus during use. The double-member of the anterior segment 1020 may include a first arm 1041 and a second arm 1042, connected by a connecting portion 1043, which may be a curved portion. In some embodiments the first arm 1041 may be parallel to the second arm 1042, and the connecting portion 1043 may be substantially perpendicular to each of the first arm 1041 and the second arm 1042. It is noted that in some embodiments a portion of the second arm 1042 may extend into the coupling portion 1025 or otherwise be connected to the lateral segment 1022. In some embodiments, the curved portion of the anterior segment 1020 may have a curvature normal to the curvature of the lateral segment 1022. In some embodiments, the curved portion of the anterior segment 1020 may have a curvature normal to the plane of the mitral valve. In some embodiments, the anterior segment 1020 may substantially occupy the transverse sinus from the inferior aspect of the transverse sinus to the superior aspect of the transverse sinus. In some embodiments, the second arm 1042 may be located on the floor of the transverse sinus, while the first arm 1041 may anchor itself against the reflection of the pericardium that separates the transverse and oblique sinuses at the top of the atrium.

Figure 21A:
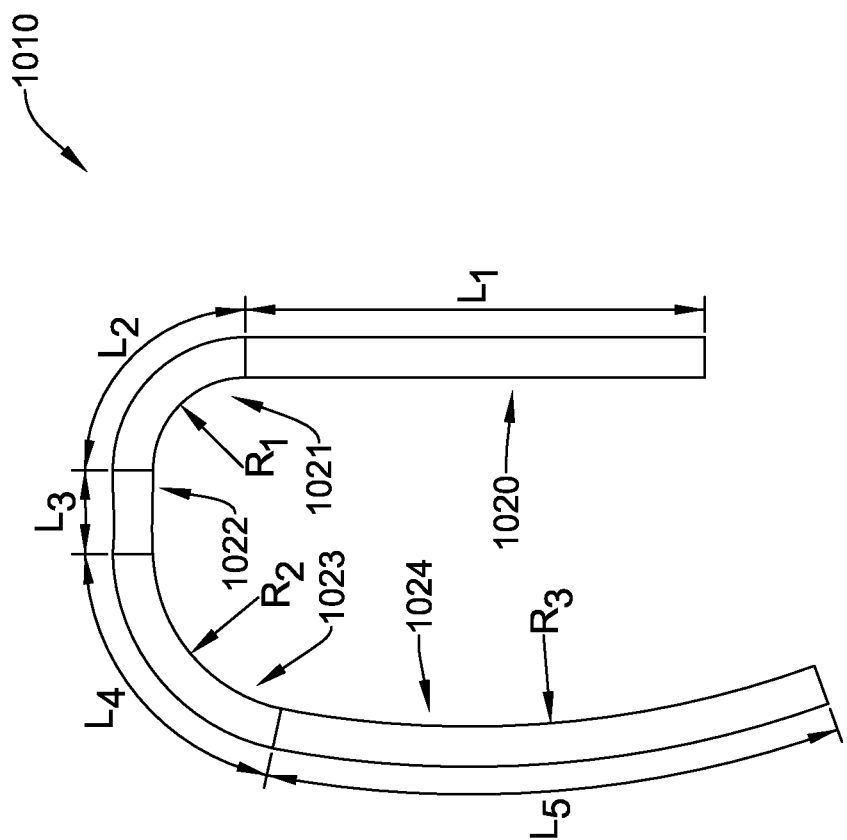
FIG. 21A is a top view illustrating exemplary curvatures and dimensions of an epicardial clip.

FIG. 21A illustrates some suitable dimensions of portions of the epicardial clip 1010. Although some suitable dimensions are indicated for the epicardial clip 1010, one of skill in the art, incited by the present disclosure, would understand that other embodiments disclosed herein, as well as additional conceivable embodiments, may include similar dimensions, if desired. For example, corresponding regions of the epicardial clip 10, 110, 210, 310, 410, 510, 610, 710, and 810 may be similarly dimensioned in some embodiments.

As shown in FIG. 21A, the anterior segment 1020, which may be a straight segment of the epicardial clip 1010, may have a length $L_1$ in the range of about 1 to about 3 inches, in the range of about 1 to about 2.5 inches, in the range of about 1.25 to about 2 inches, or in the range of about 1.28 to about 2.07 inches in some instances. In other embodiments, the anterior segment 1020 may be a curved segment having an arc length in the range of about 1 to about 3 inches, in the range of about 1 to about 2.5 inches, in the range of about 1.25 to about 2 inches, or in the range of about 1.28 to about 2.07 inches in some instances.

The epicardial clip 1010 may have an anterior/lateral curve segment 1021 defining a transition region between the anterior segment 1020 and the lateral segment 1022. In some embodiments, the anterior/lateral curve segment 1021 may be considered a portion of the anterior segment 1020, while in other embodiments the anterior/lateral curve segment 1021 may be considered a portion of the lateral segment 1022. In other embodiments, a first portion of the anterior/lateral curve segment 1021 may be associated with the anterior segment 1020, while a second portion of the anterior/lateral curve segment 1021 may be associated with the lateral segment 1022. The anterior/lateral curve segment 1021 may have an arc length $L_2$ in the range of about 0.25 to about 1.5 inches, in the range of about 0.5 to about 1 inches, in the range of about 0.4 to about 1.1 inches, or in the range of about 0.43 to about 1.09 inches in some instances. The anterior/lateral curve segment 1021 may have a radius of curvature $R_1$ of about 0.1 to about 1.25 inches, about 0.2 to about 1 inches, about 0.25 to about 0.75 inches, or about 0.24 to about 0.74 inches in some instances.

The lateral segment 1022 may include a straight portion located between the anterior/lateral curve segment 1021 and the posterior/lateral curve segment 1023. Thus, in some embodiments, the lateral segment 1022 may include a straight portion located between a first curved portion and a second curved portion of the lateral segment 1022. The straight portion of the lateral segment 1022 may have a length $L_3$ in the range of about 0.1 to about 0.5 inches, in the range of about 0.2 to about 0.4 inches, in the range of about 0.15 to about 0.35 inches, or in the range of about 0.15 to about 0.35 inches in some instances.

The epicardial clip 1010 may have a posterior/lateral curve segment 1023 defining a transition region between the lateral segment 1022 and the posterior segment 1024. In some embodiments, the posterior/lateral curve segment 1023 may be considered a portion of the lateral segment 1022, while in other embodiments the posterior/lateral curve segment 1023 may be considered a portion of the posterior segment 1024. In other embodiments, a first portion of the posterior/lateral curve segment 1023 may be associated with the lateral segment 1022, while a second portion of the posterior/lateral curve segment 1023 may be associated with the posterior segment 1024. The posterior/lateral curve segment 1023 may have an arc length $L_4$ in the range of about 0.25 to about 1.5 inches, in the range of about 0.5 to about 1.0 inches, in the range of about 0.65 to about 1.1 inches, or in the range of about 0.64 to about 1.1 inches in some instances. The posterior/lateral curve segment 1023 may have a radius of curvature $R_2$ of about 0.2 to about 1.25 inches, about 0.3 to about 1.0 inches, about 0.4 to about 0.85 inches, or about 0.44 to about 0.87 inches in some instances.

The posterior segment 1024, which may be a curved segment of the epicardial clip 1010, may have an arc length $L_5$ in the range of about 1 to about 3 inches, in the range of about 1.25 to about 2.75 inches, in the range of about 1.5 to about 2.5 inches, or in the range of about 1.55 to about 2.5 inches in some instances. The posterior segment 1024 may have a radius of curvature $R_3$ in the range of about 2 to about 5 inches, about 2.5 to about 4.5 inches, about 3 to about 4 inches, or about 2.9 to about 4.1 inches in some instances.

In some embodiments, the anterior segment 1020 may be able to be rotated relative to the posterior segment 1024 and/or lateral segment 1022. For example, the anterior segment 1020 may be able to be rotated around an axis running longitudinally through the coupling member 1025 of the anterior segment 1020. In other embodiments, the anterior segment 1020 may be oriented at a fixed angle relative to the posterior segment 1024 and/or lateral segment 1022.

Figure 22:
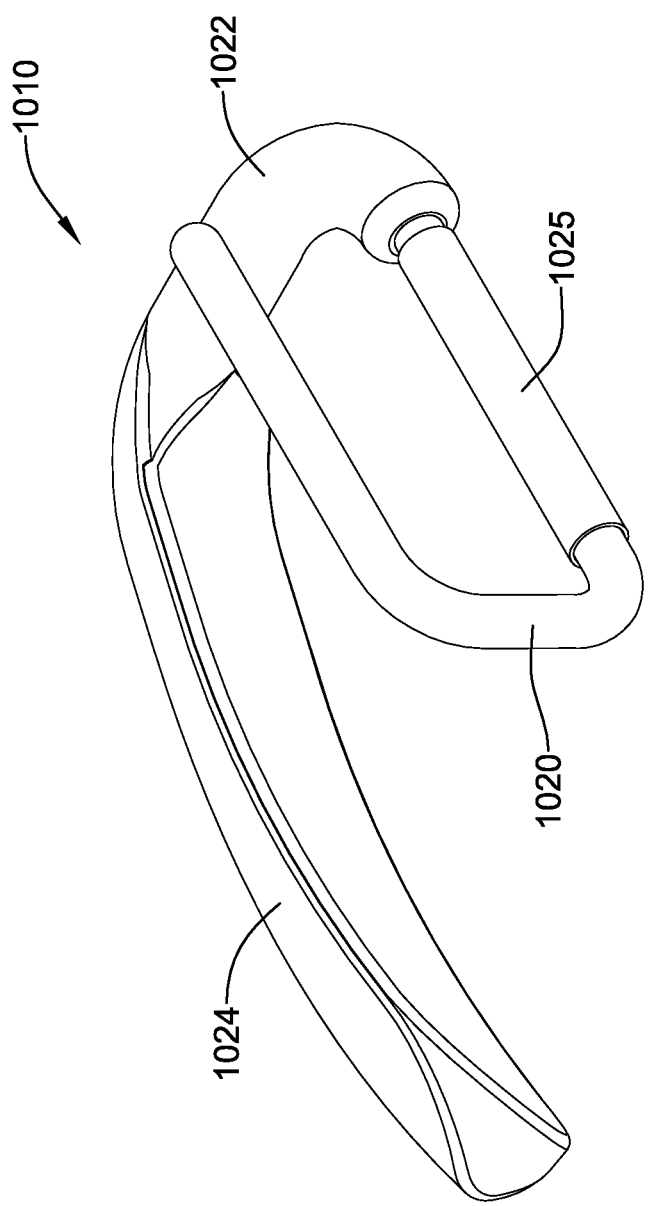
FIG. 22 is a perspective view of the epicardial clip shown in FIGS. 19 and 20 with the anterior segment rotated.

FIG. 22 is a perspective view of the epicardial clip 1010 with the anterior segment 1020 rotated to a position such that the imaginary plane in which the anterior segment 1020 lies in is substantially perpendicular with the imaginary plane in which the posterior segment 1024 and/or the lateral segment 1022 lies in.

Figure 23A:
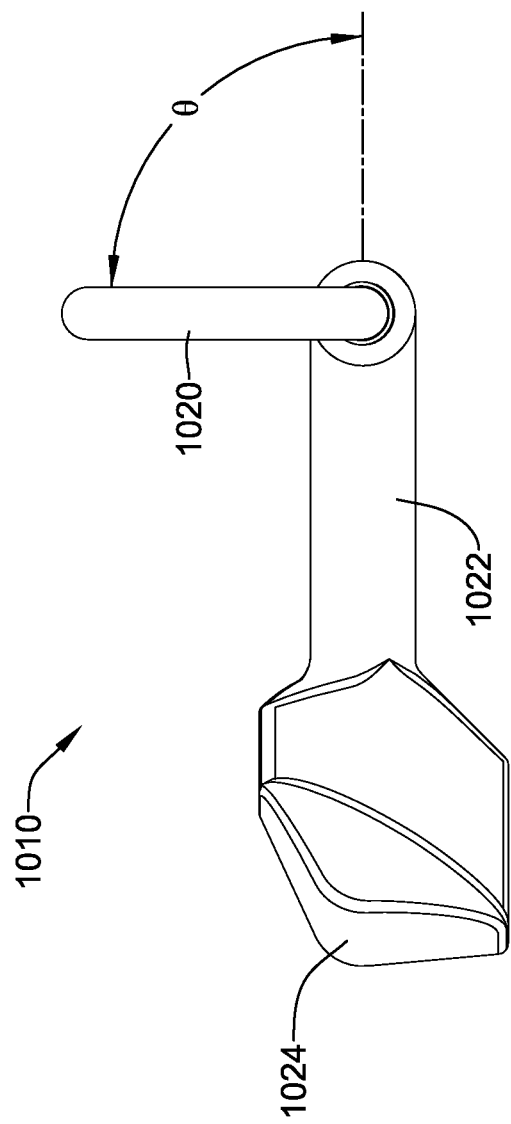
FIGS. 23A-23C are side views of the epicardial clip shown in FIGS. 19 and 20 showing various possible rotated positions of the anterior segment.
Figure 23B:
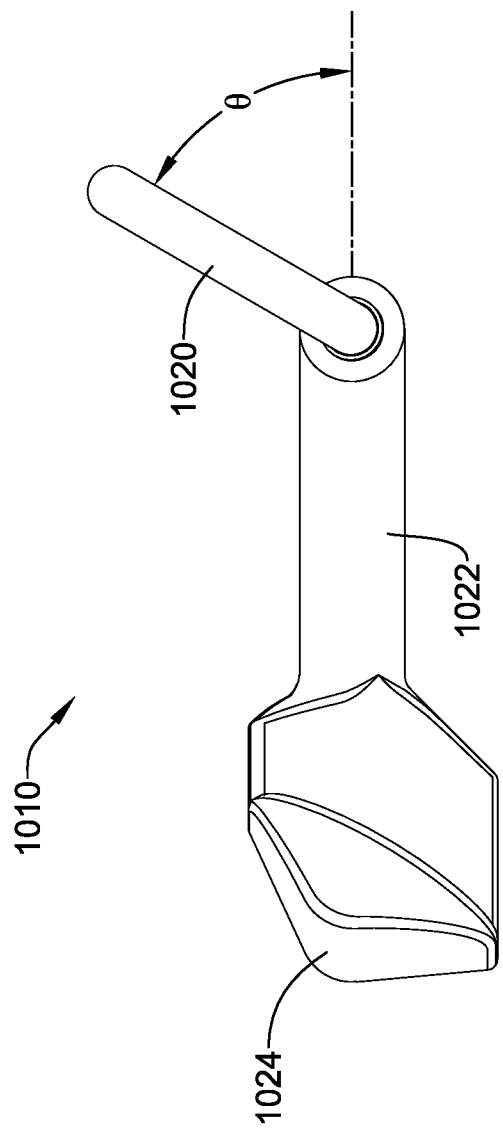
Figure 23C:
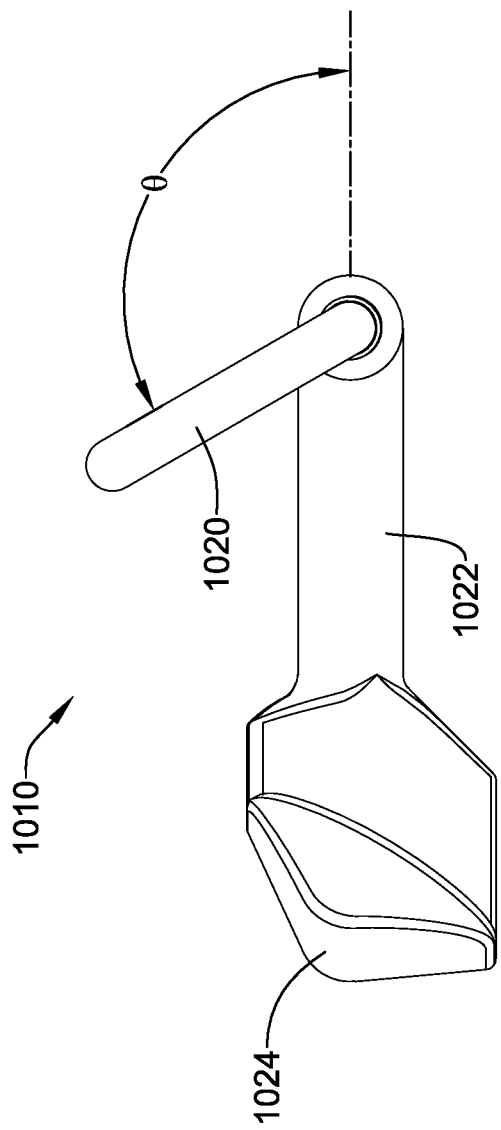

FIGS. 23A-23C are side views of the epicardial clip 1010 showing the anterior segment 1020 at three possible rotated positions relative to the posterior segment 1024 and/or the lateral segment 1022. In some embodiments, the anterior segment 1020 can be rotated to any desired angle θ relative to the posterior segment 1024 and/or the lateral segment 1022. FIG. 23A shows the anterior segment 1020 rotated to about 90° relative to the posterior segment 1024 and the lateral segment 1022. FIG. 23B shows the anterior segment 1020 rotated to about 60° relative to the posterior segment 1024 and the lateral segment 1022. FIG. 23C shows the anterior segment 1020 rotated to about 120° relative to the posterior segment 1024 and the lateral segment 1020. In can be appreciated that in some embodiments the anterior segment 1020 may be rotated from about 0° to about 180°, about 30° to about 150°, about 45° to about 135°, about 60° to about 120°, about 70° to about 110°, about 80° to about 100°, or between any other desired range of rotation.

Figure 24:
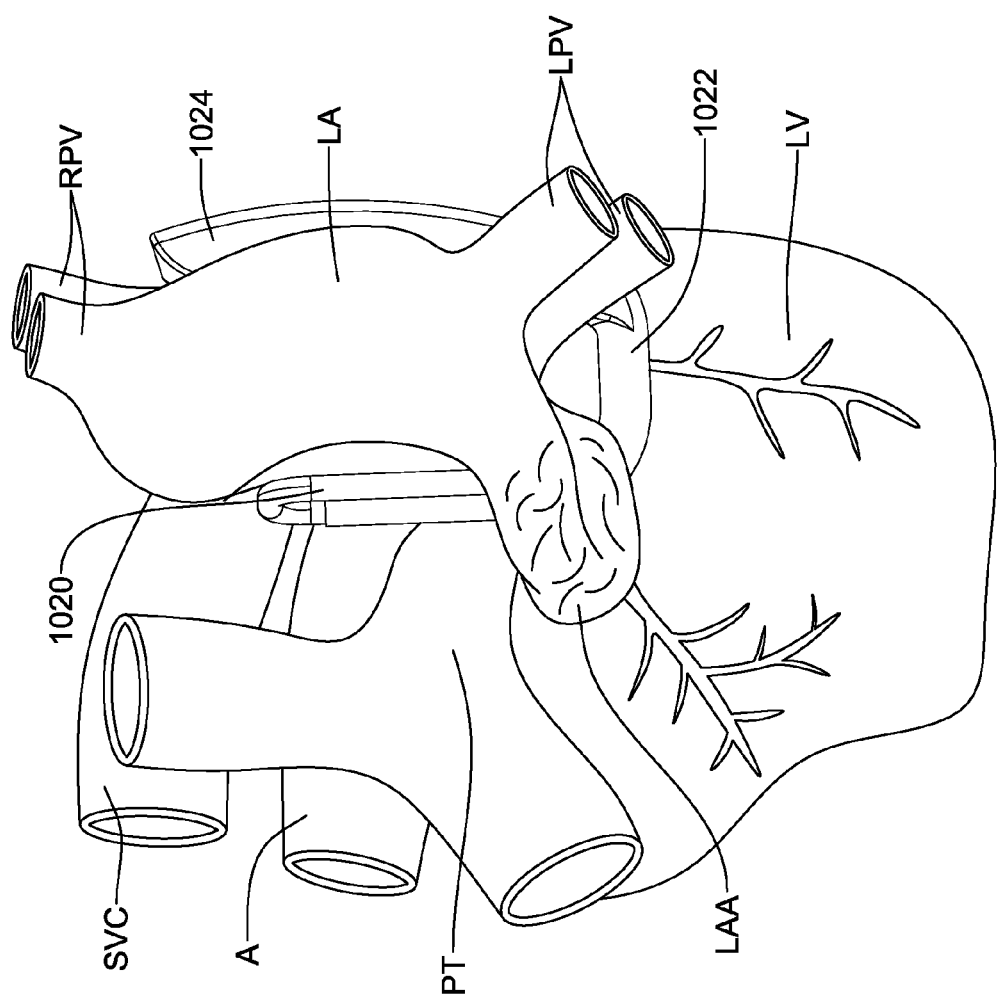

FIG. 24 is a top view looking down on the atriums of a heart onto which the epicardial clip 1010 has been positioned. As shown in FIG. 24, when positioned on the heart, the anterior segment 1020 of the epicardial clip 1010 may be positioned in the transverse sinus TS, posterior to the pulmonary trunk PT and the aorta A, and anterior to the superior vena cava SVC. When positioned in the transverse sinus TS, the double-member of the anterior segment 1020 may be substantially placed vertically in the transverse sinus TS. For example, the double-member of the anterior segment 1020, or another component of the anterior segment 1020 may substantially occupy or span the transverse sinus from the inferior aspect of the transverse sinus to the superior aspect of the transverse sinus. The position and shape of the anterior segment may be found to provide enhanced retention and/or stability in the transverse sinus TS.

As shown in FIG. 24, the posterior segment 1024 may be positioned on the epicardial surface of the posterior side of the heart, such as on or inferior to the atrioventricular groove or in the oblique sinus OS. Thus, the distance maintained between the anterior segment 1020 and the posterior segment 1024 may push an anterior wall of the heart toward a posterior wall of the heart, reshaping the geometry of the heart. For example, properly positioning the epicardial clip 1010 around a portion of the heart may change the anterior-posterior dimension and/or the septal-lateral dimension of the mitral valve annulus in order to reshape the mitral valve annulus to reduce mitral valve regurgitation.

Figure 25:
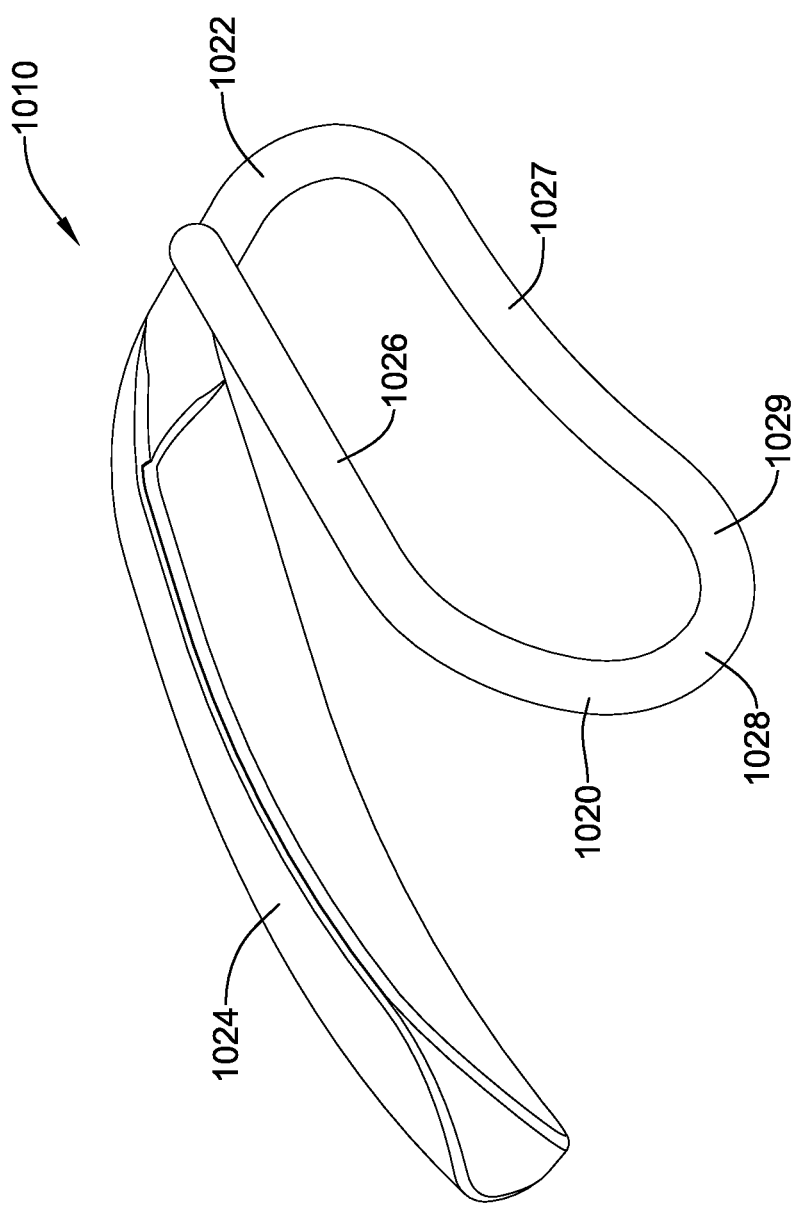
FIGS. 25-29 are alternative configurations of the epicardial clip shown in FIGS. 19 and 20.

FIGS. 25-29 illustrate alternative configurations of the epicardial clip 1010 shown in FIGS. 19 and 20. As shown in FIG. 25, the epicardial clip 1010 may include an anchored or non-rotating anterior segment 1020. In such an embodiment, the anterior segment 1020 may be formed or chosen to have a desired angle and/or curvature to complement the anatomical contours of a specific patient to ensure forces between the anterior segment 1020 and the cardiac structures of the heart are controlled. For instance, the anterior segment 1020 shown in FIG. 25 includes a superior arm portion 1026, an inferior arm portion 1027, and a lateral portion 1028 extending between the superior arm portion 1026 and the inferior arm portion 1027. The inferior arm portion 1027 may be configured to rest in the inferior aspect of the transverse sinus. The superior arm portion 1026 may be configured to reside in the superior aspect of the transverse sinus.

In some embodiments, the inferior arm portion 1027 may include an arc having a concave curvature, curving inferiorly, allowing the inferior arm portion 1027 of the anterior segment 1020 to better conform to the natural saddle shape of the anterior annulus or floor of the transverse sinus, and such that an end portion 1029 of the inferior arm portion 1027 may be disposed at and/or in contact with the floor of the septal wall between the right atrium and the left atrium.

Figure 26:
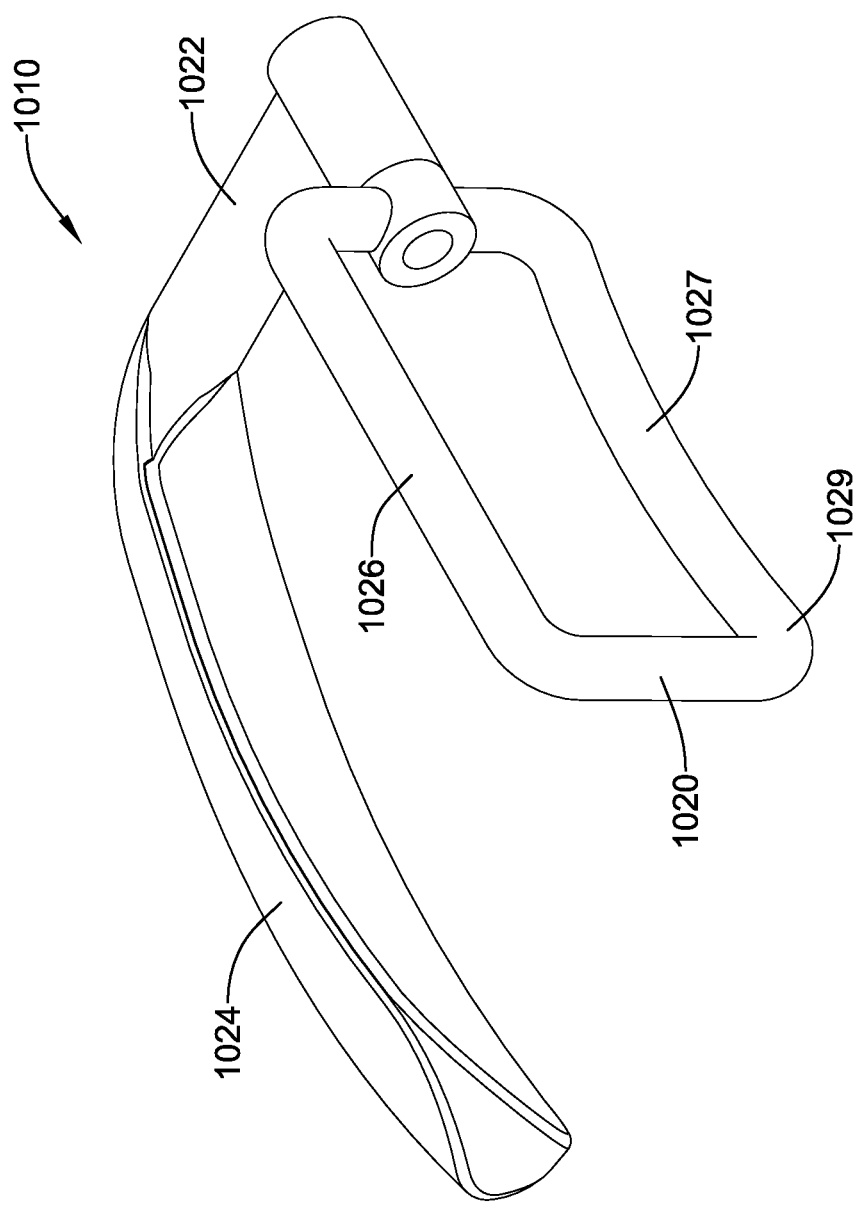

As shown in the alternative configuration of FIG. 26, the anterior segment 1020 may be a closed loop including a superior arm portion 1026 and an inferior arm portion 1027 configured to be located inferior to the superior portion 1026 when placed in the transverse sinus. The inferior arm portion 1027 may be located on the floor of the transverse sinus, while the superior arm portion 1026 may anchor itself against the reflection of the pericardium that separates the transverse and oblique sinuses at the top of the atrium. Additionally, the lateral segment 1022 is shown attached to a median portion of the closed loop of the anterior segment 1020 with an attachment point positioned between the superior arm portion 1026 and the inferior arm portion 1027. In the embodiment shown in FIG. 26, the anterior segment 1020 is free to rotate relative to the lateral segment 1022 and/or the posterior segment 1024 of the epicardial clip 1010. It has been found that in some instances attaching the lateral segment 1022 at a median location of the anterior segment 1020 while allowing free rotation of the anterior segment 1020 relative to the other portions of the clip 1010 may help evenly distribute forces on the cardiac structures of the heart between the superior arm portion 1026 and the inferior arm portion 1027 of the anterior segment 1020. More evenly distributing forces may reduce bulge of the cardiac structures by having two smaller bulges as opposed to a single larger bulge.

Similar to that of FIG. 25, the inferior arm portion 1027 shown in FIG. 26 may be configured to rest in the inferior aspect of the transverse sinus. In some embodiments, the inferior arm portion 1027 may include an arc having a concave curvature, curving inferiorly, allowing the inferior arm portion 1027 of the anterior segment 1020 to better conform to the natural saddle shape of the anterior annulus or floor of the transverse sinus, and such that an end portion 1029 of the inferior arm portion 1027 may be disposed at and/or in contact with the floor of the septal wall between the right atrium and the left atrium.

Figure 27:
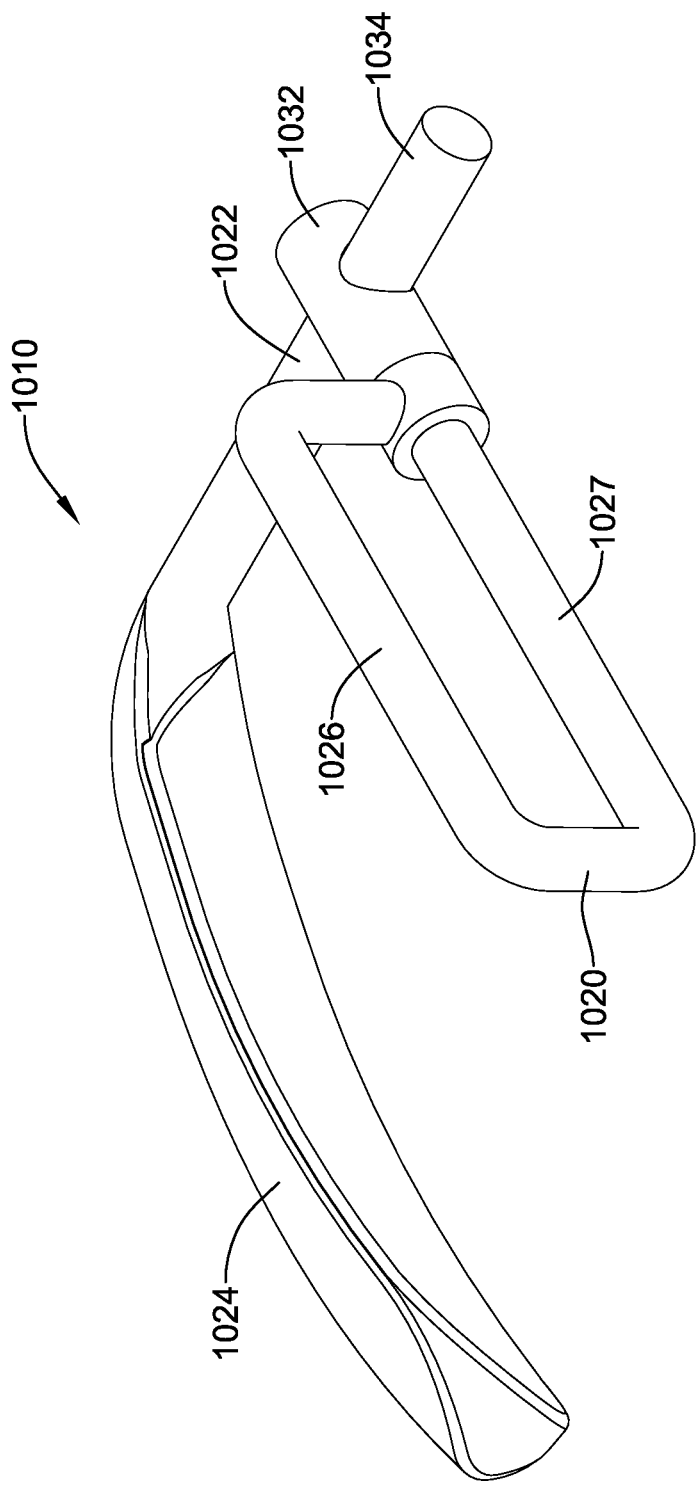

The alternative configuration shown in FIG. 27 illustrates the anterior segment 1020 having a closed loop connected to the lateral segment 1022 of the epicardial clip 1010. The anterior segment 1020 may be rotatably coupled to the lateral segment 1022 to allow rotation of the anterior segment 1020. As shown in FIG. 27, the connection between the anterior segment 1020 and the lateral segment 1022 may be proximate the inferior arm portion 1027 of the anterior segment 1020. In such an embodiment, a majority of the force transmitted to the cardiac structures of the heart is through the inferior arm portion 1027 of the anterior segment 1020.

Additionally, as shown in FIG. 27, the lateral segment 1022 may allow for repositioning the anterior segment 1020 relative to the posterior segment 1024 to adjust the distance between the anterior segment 1020 and the posterior segment 1024. For example, lateral segment 1022 may include a rod 1034 over which a coupling portion 1032 of the anterior segment 1020 and/or the posterior segment 1024 may be disposed. The coupling portion 1032 of the anterior segment 1020 and/or the posterior segment 1024 may be slid or moved along the rod 1034 to alter the distance. The anterior segment 1020 and/or the posterior segment 1024 may be secured to the lateral segment 1022, for example with a set screw in the coupling portion 1032, when the desired distance has been achieved.

Figure 28:
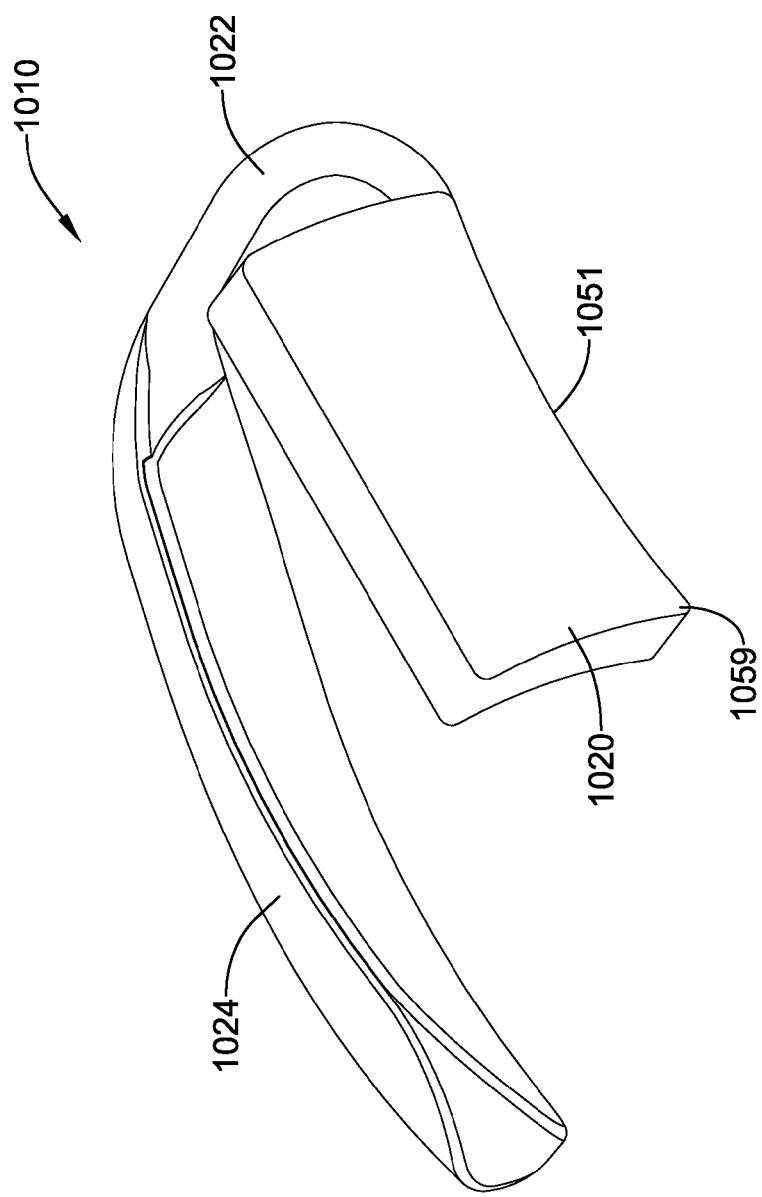

Instead of two arm portions separated by a gap or opening, the alternative configuration shown in FIG. 28 illustrates the anterior segment 1020 as being a paddle sized to substantially occupy the transverse sinus from an inferior aspect of the transverse sinus to a superior aspect of the transverse sinus. The paddle of the anterior segment 1020 may have an inferior edge 1051 and a superior edge 1052. In some embodiments the inferior edge 1051 of the anterior segment 1020 may have a concave curvature, curving inferiorly, allowing the inferior edge 1051 of the anterior segment 1020 to better conform to the natural saddle shape of the anterior annulus or floor of the transverse sinus, and such that an end portion 1059 of the inferior edge 1051 may be disposed at and/or in contact with the floor of the septal wall between the right atrium and the left atrium, while the curvature of a central portion of the inferior edge 1051 of the anterior segment 1020 may prevent the middle portion from adversely pushing into the atrium of the heart.

Figure 29:
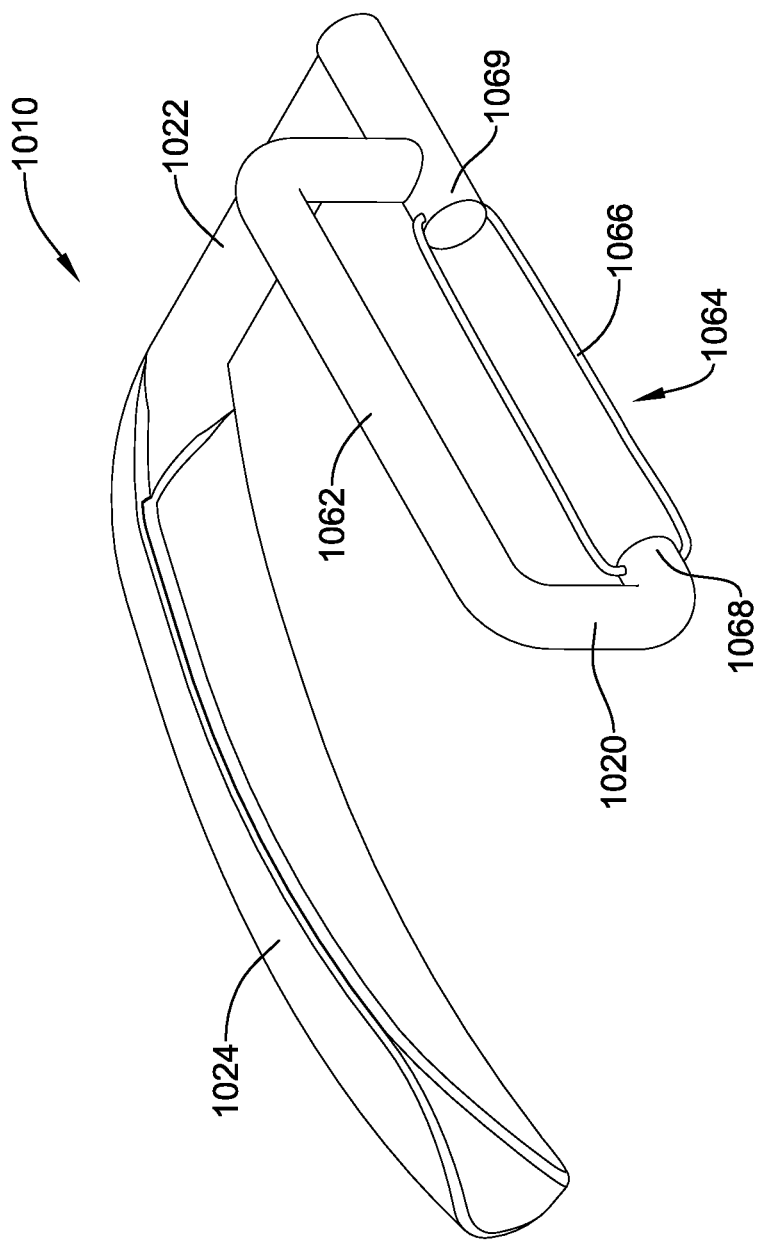

The configuration of the epicardial clip 1010 shown in FIG. 29 includes an anterior segment 1020 including a rigid or semi rigid superior arm portion 1062 and a flexible, or more flexible, inferior arm portion 1064. In some embodiments the inferior arm portion 1064, or another portion of the anterior segment 1020, may include an elastic band 1066, such as a rubber band. For example, the elastic band 1066 may be stretched between two anchor points 1068, 1069 of the anterior segment 1020. The elastic band 1066, used as an inferior arm portion 1064 of the anterior segment 1020 may help conform to the floor of the transverse sinus. The two anchor points 1068, 1069 may be configured to support most of the force exerted by the epicedial clip 1010, thus the elastic band 1066 may be able to conform to the shape of the floor of the transverse sinus without pushing excessively on the left atrium or against the aorta.

Figure 30:
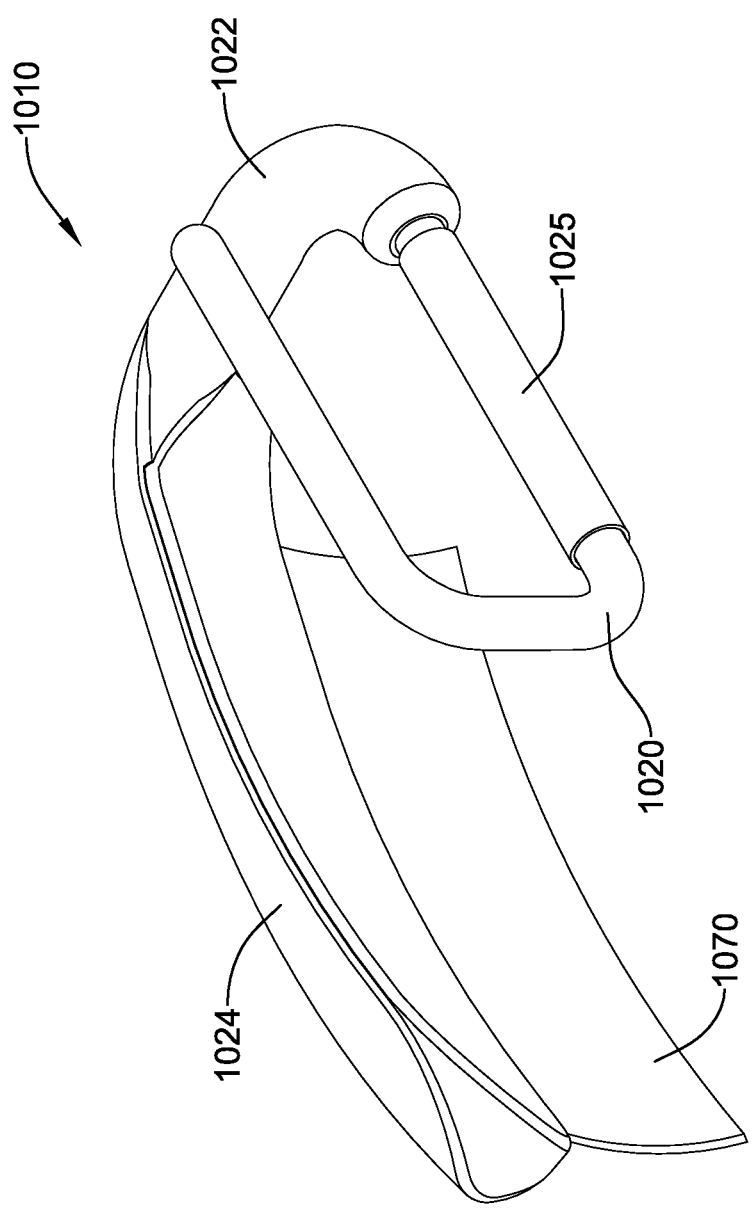
FIG. 30 shows the epicardial clip of FIGS. 19 and 20 with a flap of material disposed on the posterior segment.
Figure 31:
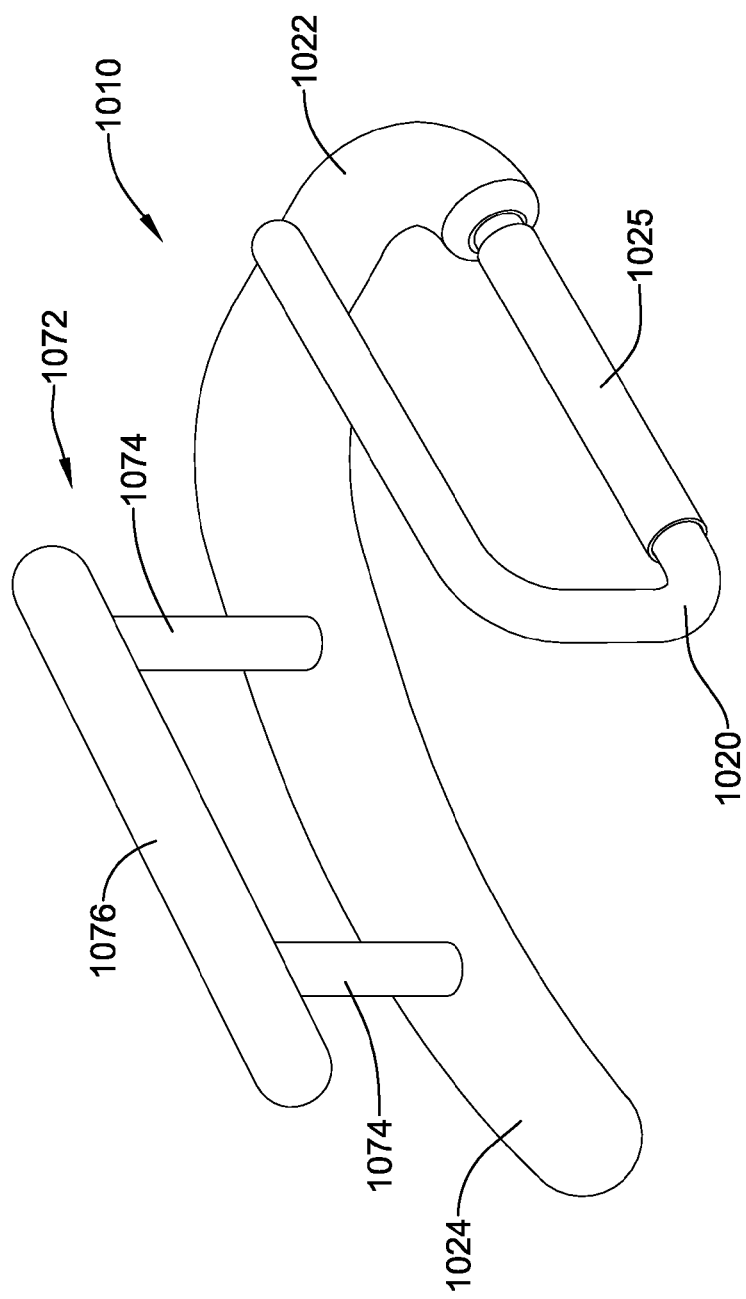
FIGS. 31-34 illustrate further modification of the epicardial clip of FIGS. 19 and 20.
Figure 32:
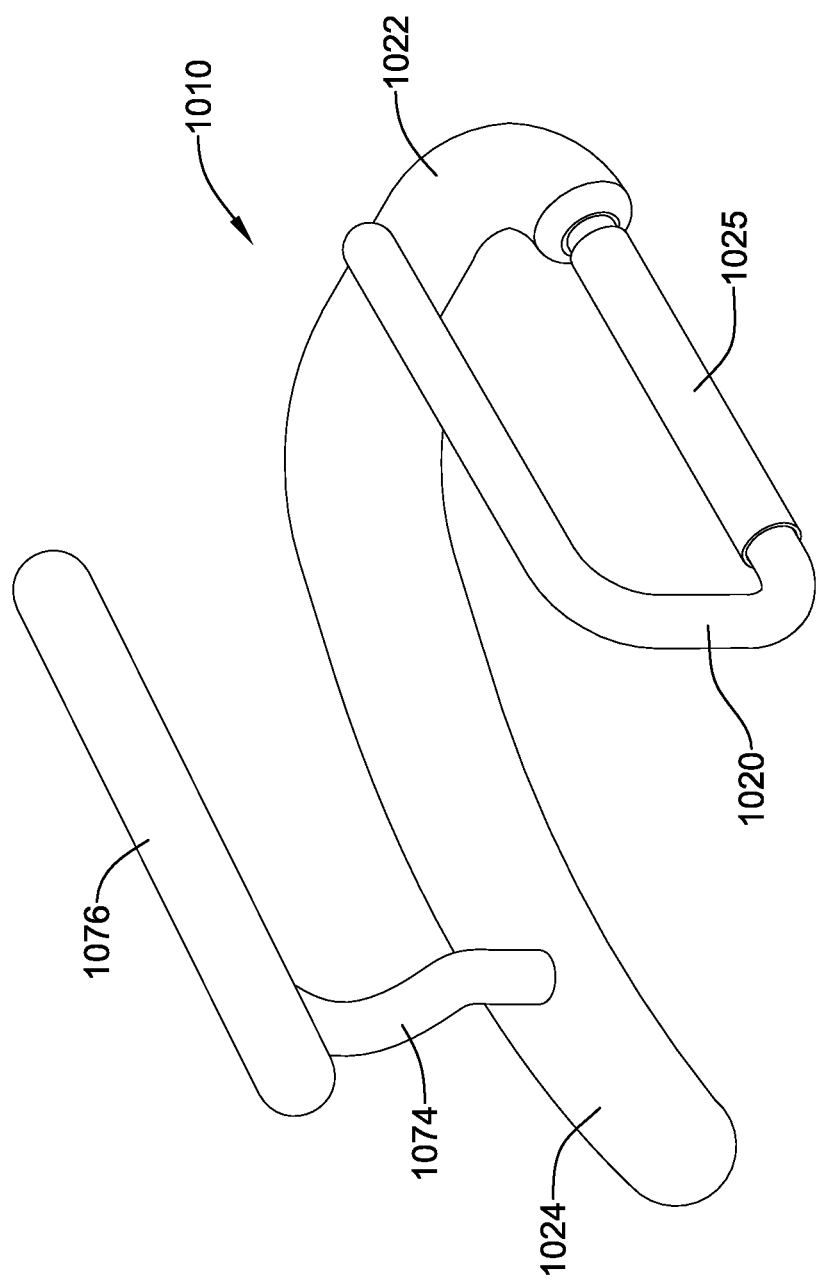

FIG. 30 shows the epicardial clip 1010 with a flap of material 1070 extending from the posterior segment 1024. The flap of material 1070 may be formed of graft material, hernia mesh, or other fabric material, or of a clear flexible material to facilitate visualization of vessels on the surface of the heart. The flap of material 1070 may be used to help anchor the clip 1010 to the surface of the heart. For example, the flap of material 1070 may be attached to the surface of the heart with tacks, sutures, or other fasteners.

In some embodiments the flap of material 1070 may be provided with the clip 1010 and attached to the heart after the posterior segment 1024 has been properly positioned. In other embodiments, the flap of material 1070 may be attached to the surface of the heart first, then the posterior segment 1024 may be connected to the flap of material when the posterior segment 1024 is being positioned. This arrangement may be helpful in order to maintain consistent positioning of the clip 1010 while adjusting, modifying, replacing or otherwise repositioning the clip 1010. In some embodiments, the flap of material 1070 may be connected to the posterior segment 1024 with sutures, clips, adhesive, tacks, barbs, or other fasteners and fastening means.

FIGS. 31-34 illustrate additional configurations of the epicardial clip 1010 including additional mechanical stability features or components. In some instances, the posterior arm 1024 may have a tendency to rotate into the atrioventricular groove and/or migrate superiorly consequent forces experienced between the clip 1010 and the heart. Thus, in some embodiments, the epicardial clip 1010 may include a mechanical feature extending from the posterior segment 1024 which pushes up on the reflection above the coronary sinus in order to provide a countering downward force to help maintain proper positioning of the clip 1010. For example, in FIG. 31 the clip 1010 may include an extension 1072 having two arms 1074 extending superiorly from the posterior segment 1024 and a cross arm 1076 extending between the two arms 1074. In the alternative embodiment shown in FIG. 32, the cross arm 1076 is connected to the posterior segment 1024 with a single arm 1074. The arm(s) 1074 may have a curvature to complement the anatomical curvature of cardiac structures of the heart. The cross arm 1076, which may be located superior to the posterior segment 1024 may contact the reflection above the coronary sinus to provide a downward force, as desired.

Figure 33:
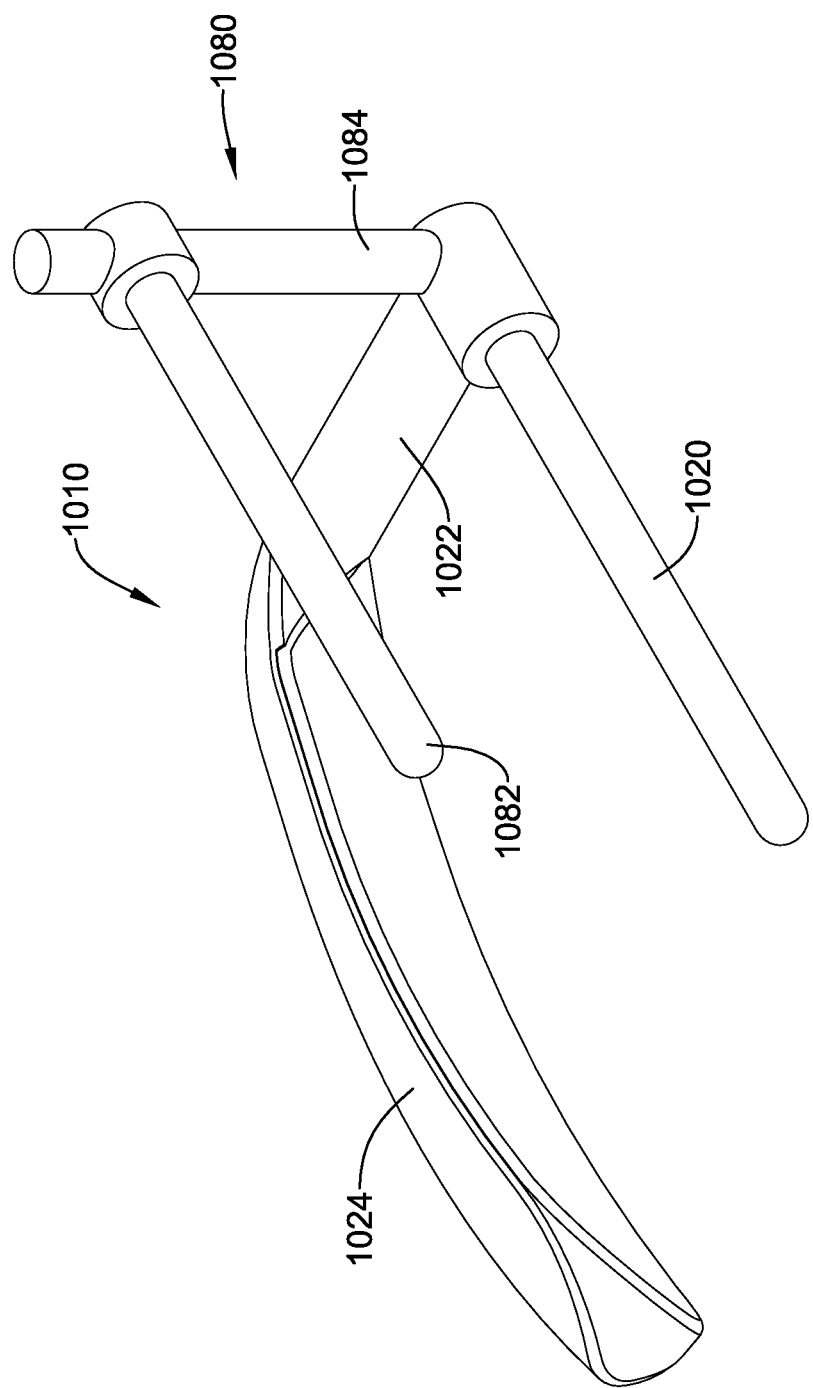

An additional embodiment, shown in FIG. 33, includes an extension 1080 of the anterior segment 1020 which may provide sufficient counterbalance to maintain the clip 1010 properly positioned on the heart. As shown in FIG. 33, the extension 1080 may include an arm 1082. The arm 1082 may be connected to a member 1084 extending from the anterior segment 1020. The connection between the arm 1082 and the member 1084 may allow the arm 1082 to selectively slide and/or rotate relative to the member 1084 and/or the anterior segment 1020 of the clip 1010. Once properly positioned, the arm 1082 may be locked in place (e.g., a set screw) to prevent further sliding and/or rotation of the arm 1082. The arm 1082, pushing against an anatomical region of the heart, may provide the desired counterbalancing force to maintain the posterior segment 1024 in a desired position.

Figure 34:
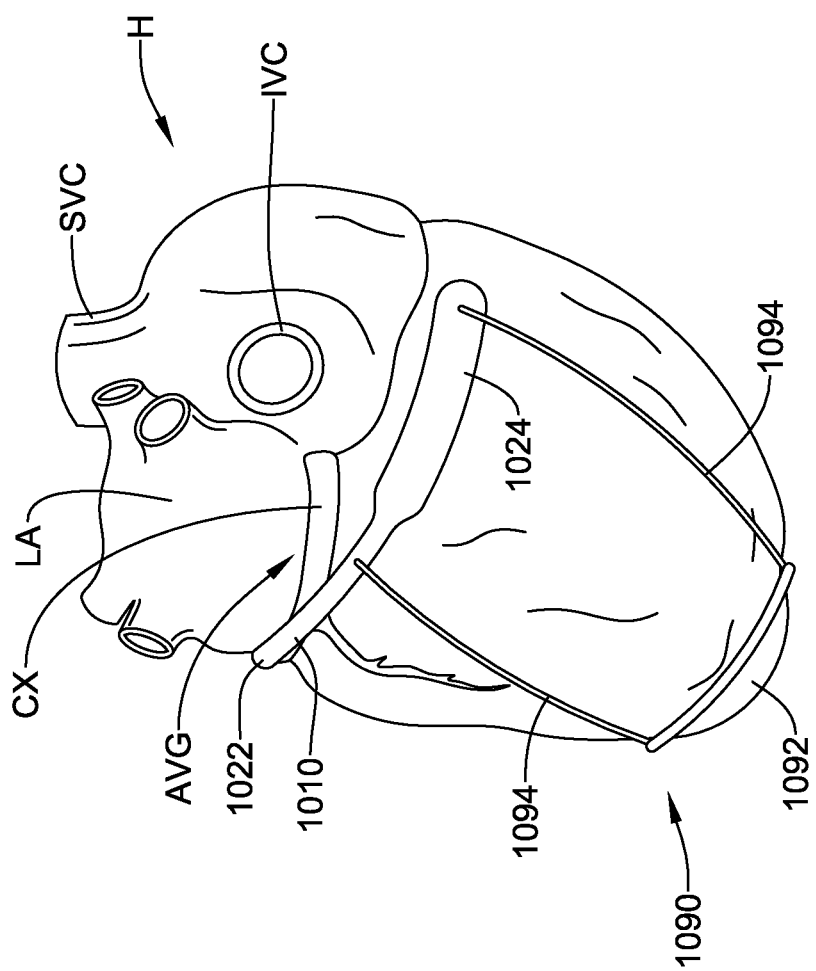

Downward force on the posterior segment 1024 may also be provided by a sling mechanism 1090 that anchors to the apex of the heart, as shown in FIG. 34. The sling mechanism 1090 may include a cap 1092 located at the apex of the heart which is connected to the posterior segment 1024 with one or more, or a plurality of tethers 1094. With the cap 1092 positioned inferior to the apex of the heart, the tethers 1094 may help draw the posterior segment 1024 downward to maintain the posterior segment 1024 in a desired position. In other embodiments, the tether(s) 1094 may be anchored to a wall of the heart with one or more anchors, tacks, sutures, or other fasteners.

FIGS. 35-38 illustrate several alternative embodiments of sizing devices which may be used to measure notable dimensions for the epicardial clip to provide proper placement on the heart and/or desired reshaping of the mitral valve. Some measurements/dimensions which may be determined using a sizing device include the cinching distance (i.e., the distance between the anterior segment and the posterior segment), the angle and/or curvature of the posterior segment, the length of the posterior segment, the angle and/or curvature of the anterior segment, the length of the anterior segment, and the height of the anterior segment. In some embodiments, the sizing device may be infinitely adjustable, while in other embodiments the sizing device may discretely adjustable between one of a plurality of discrete sizes. The discrete sizes of a discretely adjustable sizing device may correspond to one of several discrete sizes of an epicardial clip available.

Figure 35:
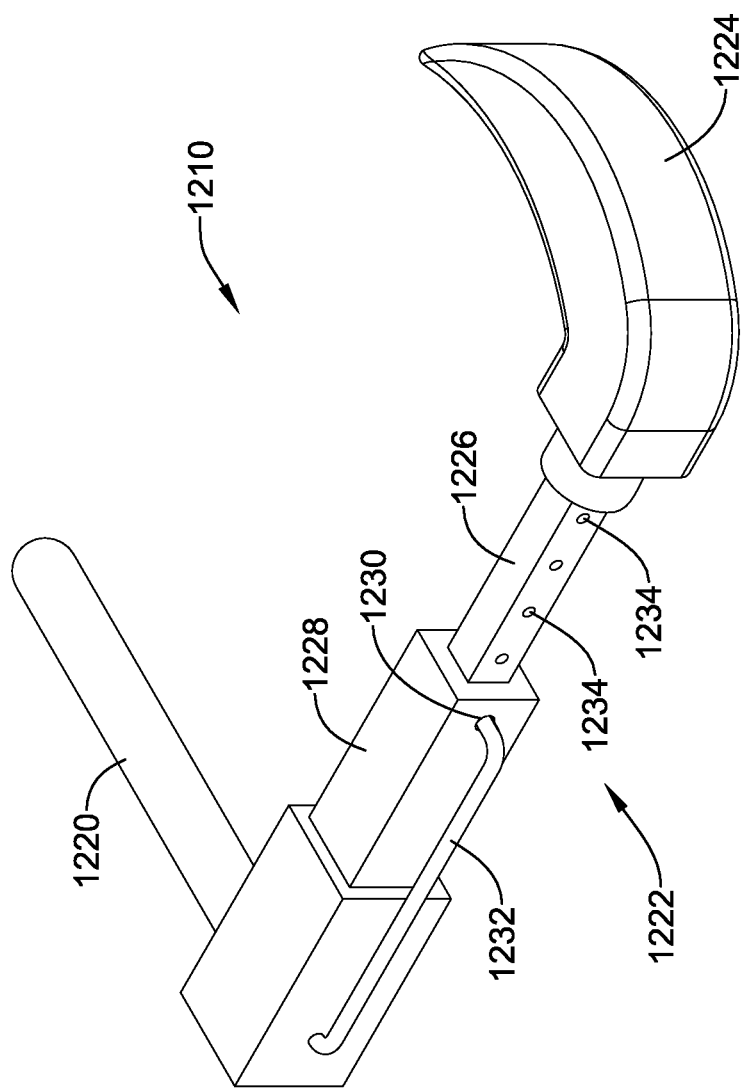
FIGS. 35-38 illustrate exemplary embodiments of a sizing device which may be used to determine the correct size, shape and/or orientation of an epicardial clip disclosed herein.

FIG. 35 illustrates one embodiment of a sizing device 1210 which may be discretely adjustable between one of a plurality of discrete sizes. The sizing device 1210 includes an anterior segment 1220 and a posterior segment 1224, which may resemble the anterior segment and posterior segment of an epicardial clip to be positioned on the heart. The length of the lateral segment 1222, extending between the anterior segment 1220 and the posterior segment 1224, may be adjusted to one of a plurality of lengths. For example, the lateral segment 1222 may include a first member 1226 telescoping into a second member 1228. The second member 1228 may include an opening 1230 through which a pin 1232, such as a spring loaded pin 1232 may extend into. The first member 1226 may include a plurality of recesses or openings 1234 into which the pin 1232 may be inserted. Thus, the first member 1226 may be actuated relative to the second member 1228 until the opening 1230 of the second member 1228 is aligned with a desired recess or opening 1234 of the first member 1226, at which point the pin 1232 may extend into the recess or opening 1234, locking the lateral segment 1222 at a fixed length. The distance between the anterior segment 1220 and the posterior segment 1224 may be changed stepwise until a desired distance is determined.

Figure 36:
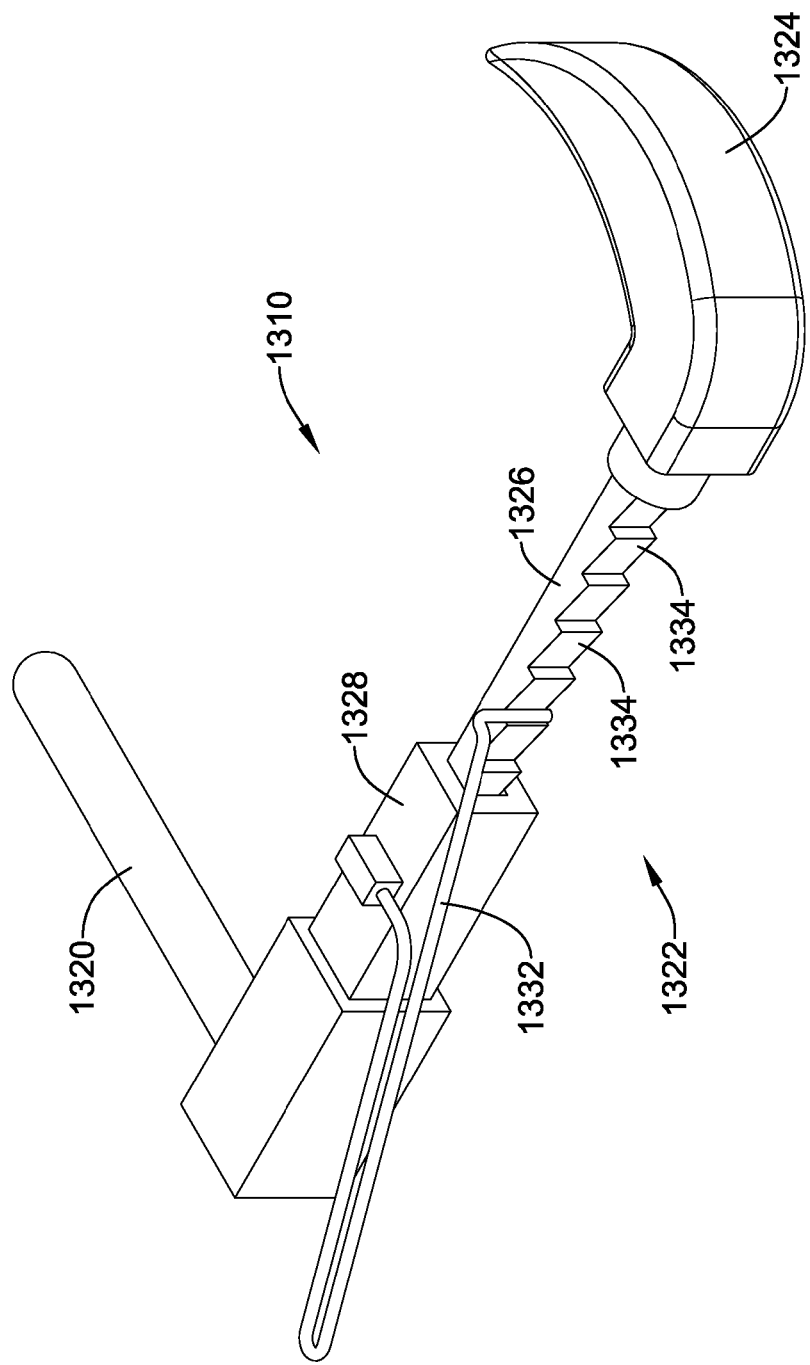

FIG. 36 illustrates another embodiment of a sizing device 1310 which may be discretely adjustable between one of a plurality of discrete sizes. The sizing device 1310 includes an anterior segment 1320 and a posterior segment 1324, which may resemble the anterior segment and posterior segment of an epicardial clip to be positioned on the heart. The length of the lateral segment 1322, extending between the anterior segment 1320 and the posterior segment 1324, may be adjusted to one of a plurality of lengths. For example, the lateral segment 1322 may include a first member 1326 telescoping into a second member 1328. The first member 1326 may include a plurality of dogs or teeth 1334 (such as a ratchet configuration) extending from one side of the first member 1326. An arm 1332 extending from the second member 1328 may engage one of the teeth 1334 to prevent further elongation of the posterior segment 1324 from the anterior segment 1320. The orientation of the teeth 1334 may allow the lateral segment 1322 to be initially elongated, thus allowing the posterior segment 1324 to be drawn toward the anterior segment 1320 in a stepwise fashion. As the posterior segment 1324 is moved toward the anterior segment 1320, the arm 1332 may be actuated out of engagement with one of the teeth 1334 and into engagement with an adjacent tooth 1334 until a desired distance between the posterior segment 1324 and the anterior segment 1320 is attained. Thus, the first member 1326 may be actuated relative to the second member 1328 until the arm 1332 is positioned at a desired tooth 1334 along the first member 1326. The distance between the anterior segment 1220 and the posterior segment 1224 may be changed stepwise until a desired distance is determined.

Figure 37:
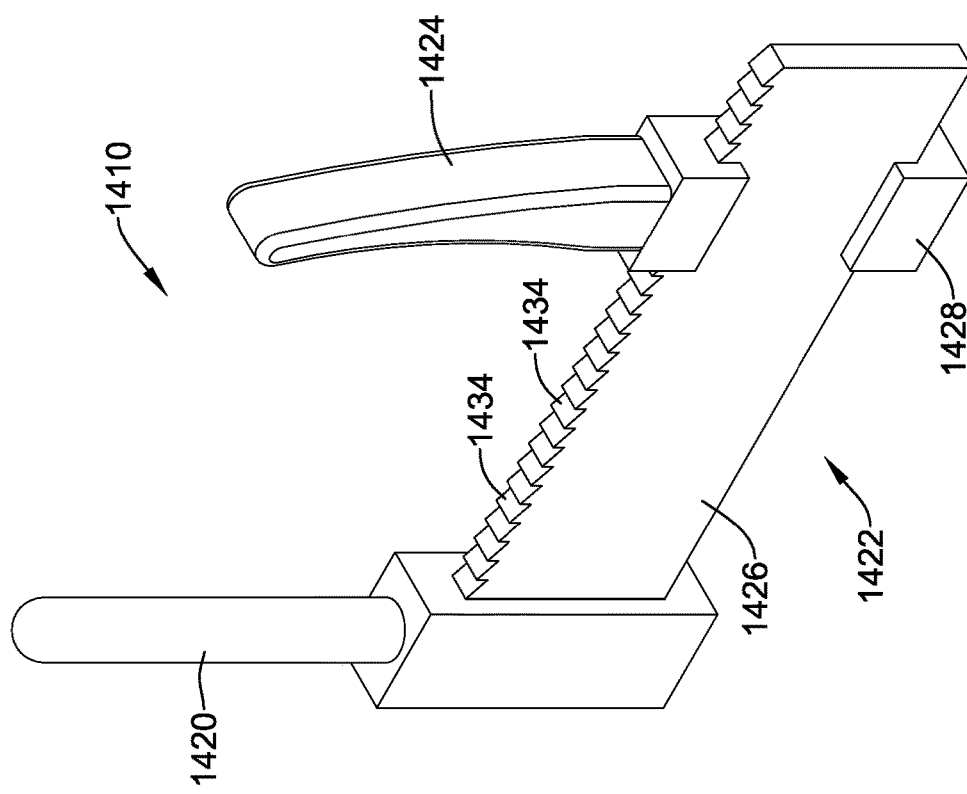

FIG. 37 illustrates yet another embodiment of a sizing device 1410 which may be adjustable. The sizing device 1410 includes an anterior segment 1420 and a posterior segment 1424, which may resemble the anterior segment and posterior segment of an epicardial clip to be positioned on the heart. The length of the lateral segment 1422, extending between the anterior segment 1420 and the posterior segment 1424, may be adjusted to one of a plurality of lengths. For example, the lateral segment 1422 may include a first member 1426 telescoping into a second member 1428. The first member 1426 may include a plurality of dogs or teeth 1434 (such as a ratchet configuration) extending from one side of the first member 1426. The orientation of the teeth 1434 may allow the lateral segment 1422 to be initially elongated, thus allowing the posterior segment 1424 to be drawn toward the anterior segment 1420 until a desired distance is attained. The first member 1426 may slideably engage the second member 1428 such as in a channel of the second member 1428. A surface of the second member 1428 may include a tab or projection (not shown) which engages the teeth 1434 of the first member 1426 as the first member 1426 is moved relative to the second member 1428. As the posterior segment 1424 is moved toward the anterior segment 1420, the tab or projection of the second member 1428 engages in the groove between two adjacent teeth 1434 to resist movement of the first member 1426 in the opposite direction. The first member 1426 may be actuated relative to the second member 1428 until the posterior segment 1424 is positioned at a desired distance from the anterior segment 1420, at which point the tab or projection of the second member 1428 may be engage one of the teeth 1434 to resist movement between the first member 1426 and the second member 1428 in the opposite direction, which may be described as a ratchet effect. The ratchet effect of the teeth 1434 may allow the distance between the anterior segment 1220 and the posterior segment 1224 may be changed until a desired distance is determined.

Figure 38:
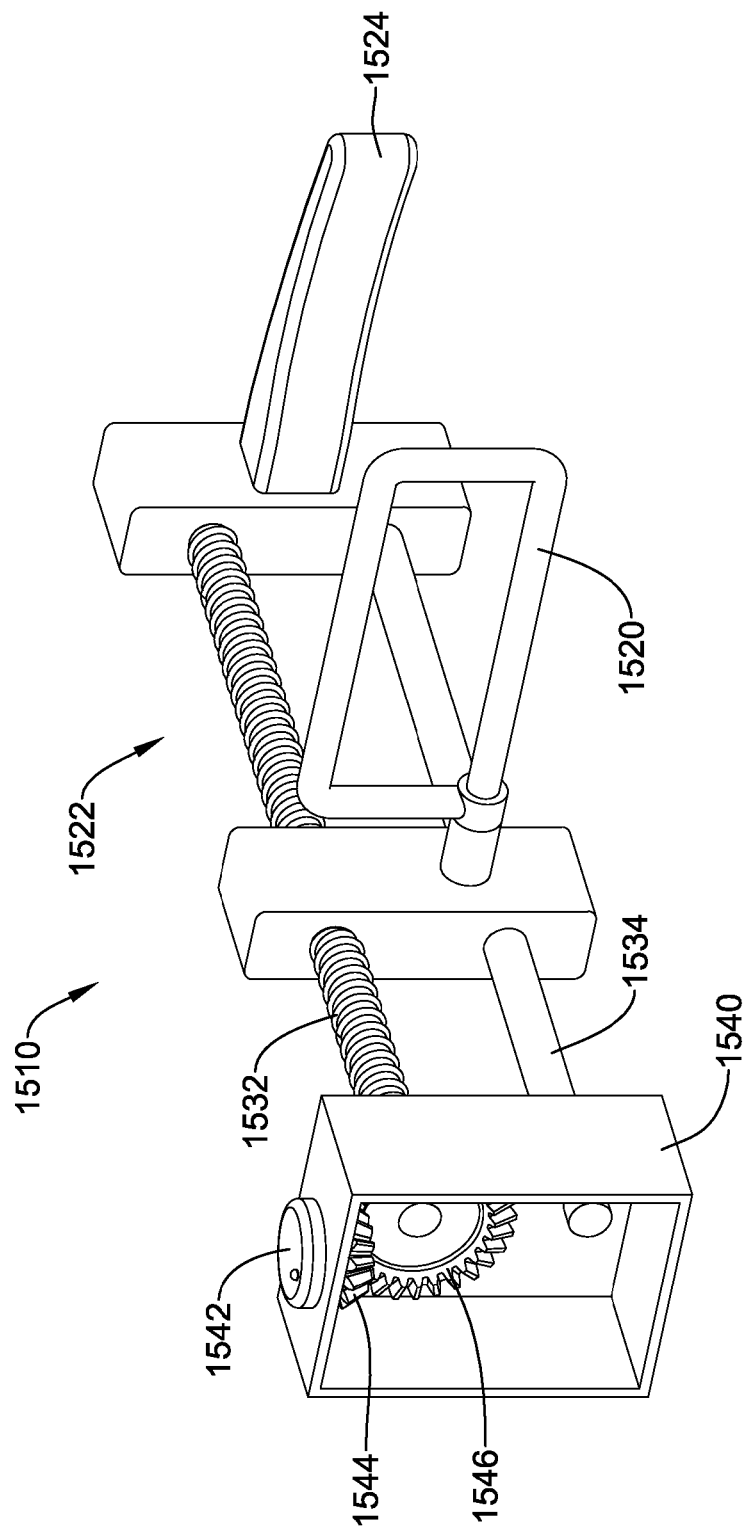

Another sizing device 1510 is illustrated in FIG. 38. The sizing device 1510 includes an anterior segment 1520 and a posterior segment 1524, which may resemble the anterior segment and posterior segment of an epicardial clip to be positioned on the heart. The length of the lateral segment 1522, extending between the anterior segment 1520 and the posterior segment 1524, may be adjusted to one of a plurality of lengths. For example, the lateral segment 1522 may include a threaded rod 1532 and a non-threaded rod 1534 extending between the anterior segment 1520 and the posterior segment 1524. The threaded rod 1532 and the non-threaded rod 1534 may extend from the anterior segment to a gear box 1540. A knob 1542 may extend from the gear box 1540. The knob 1542 may be secured to a shaft which is in turn secured to a gear 1544 in the gear box 1540. The gear 1544 may mesh with a gear 1546 secured to the threaded rod 1532. Thus, rotation of the knob 1542 may rotate the threaded rod 1532.

Rotation of the threaded rod 1532 may adjust the distance between the anterior segment 1520 and the posterior segment 1524. For example, in embodiments in which the anterior segment 1520 includes a threaded bore engaging the threads of the threaded rod 1532, rotation of the threaded rod 1532 may advance the anterior segment 1520 along the threaded rod 1532. In such an embodiment, the posterior segment 1524 may remain in a stationary location along the length of the threaded rod 1532. The inclusion of the non-threaded rod 1534 may prevent rotation of the anterior segment 1520 as the threaded rod 1532 is rotated, while still allowing translational movement of the anterior segment 1520 along the threaded rod 1532 and the non-threaded rod 1534.

In embodiments in which the posterior segment 1524 includes a threaded bore engaging the threads of the threaded rod 1532, rotation of the threaded rod 1532 may advance the posterior segment 1524 along the threaded rod 1532. In such an embodiment, the anterior segment 1524 may remain in a stationary location along the length of the threaded rod 1534. The inclusion of the non-threaded rod 1534 may prevent rotation of the posterior segment 1524 as the threaded rod 1532 is rotated, while still allowing translational movement of the posterior segment 1524 along the threaded rod 1532 and the non-threaded rod 1534.

The knob 1542 may be rotated until a desired distance between the anterior segment 1520 and the posterior segment 1524 is attained, allowing for an infinitely adjustable distance between the anterior segment 1520 and the posterior segment 1524.

Figure 39A:
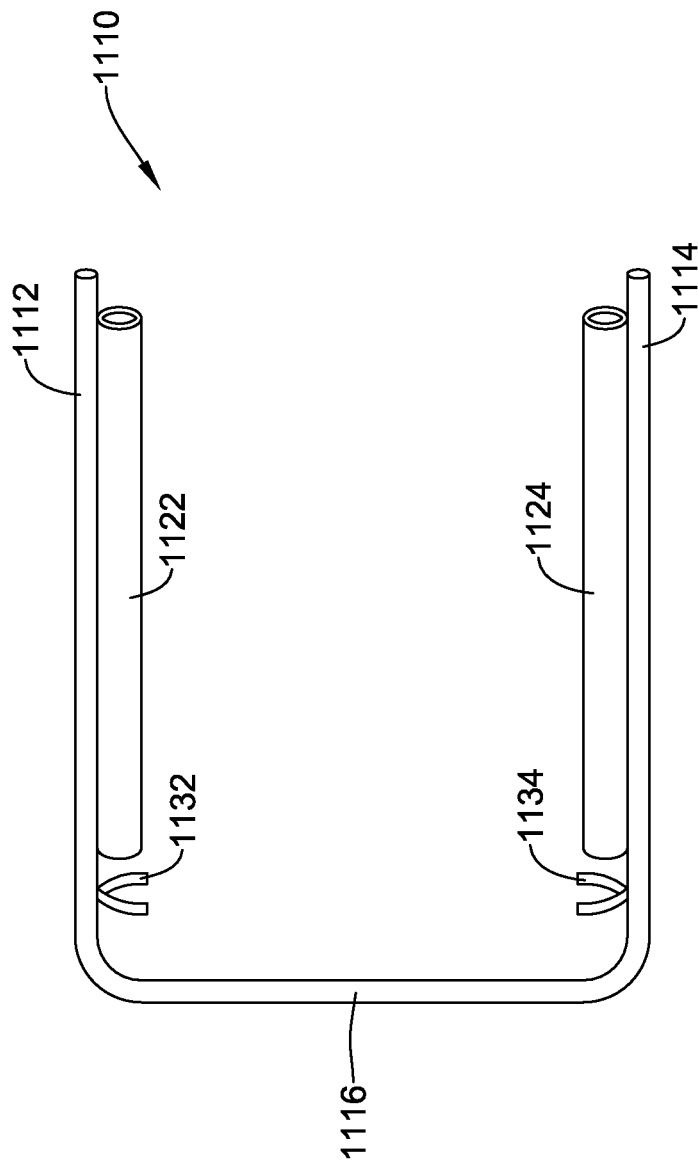
FIGS. 39A and 39B illustrate additional embodiments of an epicardial clip.

FIG. 39A illustrates a C-shaped or U-shaped epicardial clip 1110. The epicardial clip 1110 includes a first leg 1112, a second leg 1114, and a back portion 1116 connecting the first leg 1112 and the second leg 1114. In some embodiments, the first leg 1112 may be substantially parallel with the second leg 1114. The first leg 1112 may be approximately perpendicular to the back portion 1116, and the second leg 1114 may be approximately perpendicular to the back portion 1116. A first tubular cuff 1122, having a lumen, may extend along the first leg 1112, and a second tubular cuff 1124, having a lumen, may extend along the second leg 1114. A first malleable element 1132 may be located on the first leg 1112, for example proximate the end of the first tubular cuff 1122. A second malleable element 1134 may be located on the second leg 1114, for example proximate the end of the second tubular cuff 1124.

The clip 1110 may be formed of a spring material such that the clip 1110 may be collapsed into a low profile, yet allows the clip 1110 to recover its original shape when released after being distorted by an applied force.

Figure 39B:
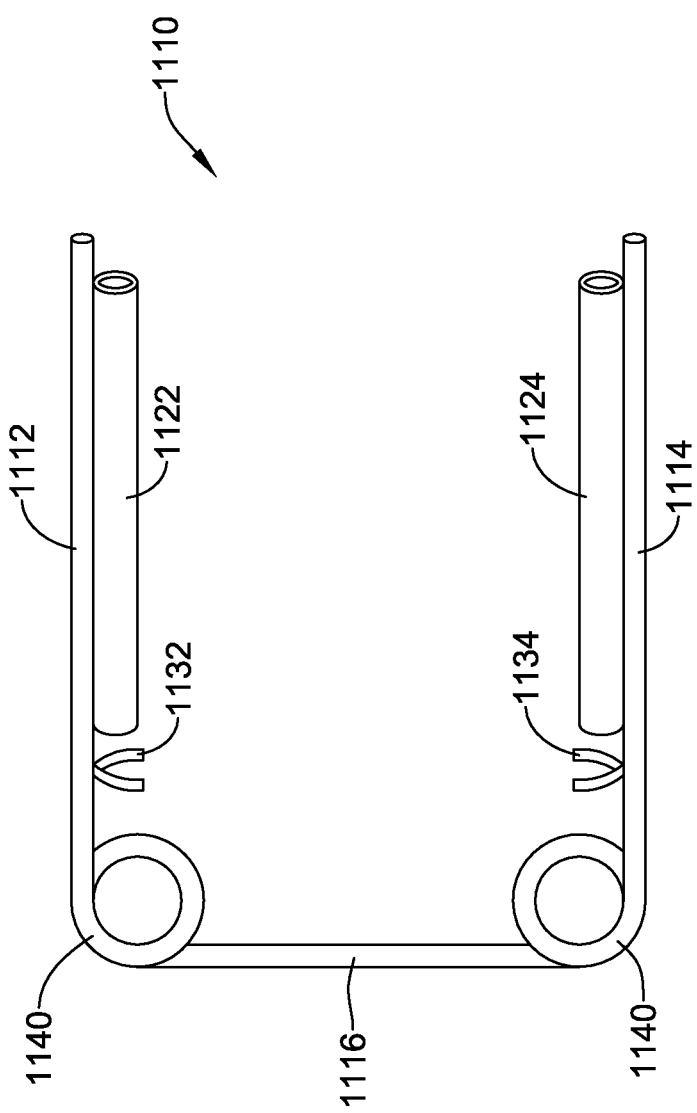

FIG. 39B illustrates an alternative arrangement of the clip 1110 including torsion spring loops 1140 at the corners between the first leg 1112 and the intermediate portion 1116, and the second leg 1114 and the intermediate portion 1116. The torsion spring loops 1140 may facilitate the ability of the clip 1110 to be collapsed into a low profile configuration, yet the torsion spring loops 1140 may allow the clip 1110 to recover its original shape when released after being distorted by an applied force.

Figure 40:
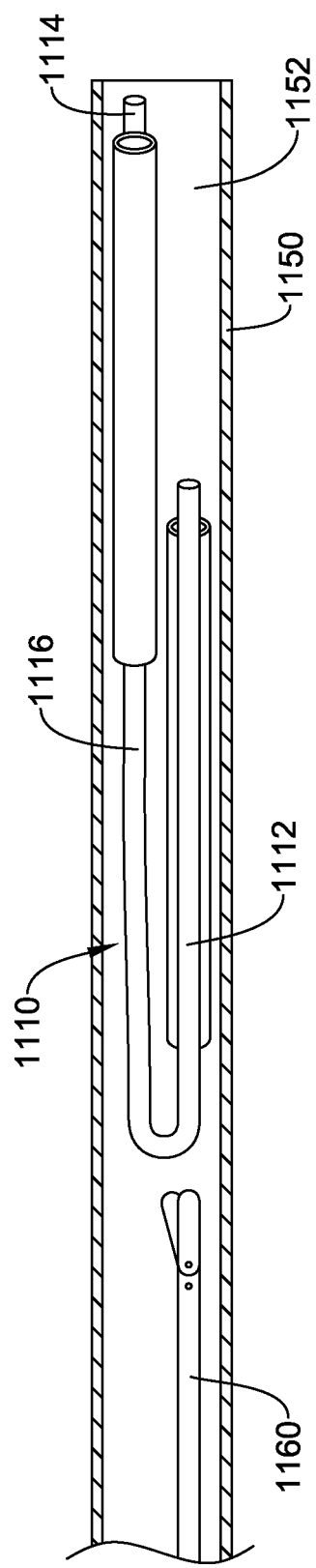
FIGS. 40-44 illustrate an exemplary method of positioning an epicardial clip on a heart.

The clip 1110 may be collapsed and loaded into the lumen 1152 of a delivery tube 1150 as shown in FIG. 40. For example, the clip 1110 may be collapsed such that the second leg 1114 and the back portion 1116 are folded against the first leg 1112, thus the clip 1110 lies substantially flat. A medical device, such as a grasper 1160 may be introduced into the delivery tube 1150 to deploy and/or maneuver the clip 1110 within the thoracic cavity of a patient. In other embodiments a rigid rod or other actuatable member may be used to deploy and/or maneuver the clip 1110 from the delivery tube 1150.

The clip 1110 may be positioned on the heart of a patient during a closed-chest, endoscopic procedure in order to adjust the anterior-posterior dimension of the annulus of the mitral valve to enhance coaptation of the leaflets of the mitral valve. This endoscopic approach positions the first leg 1112 of the clip 1110 in the transverse sinus and the second leg 1114 of the clip 1110 on the posterior side of the heart, such as on or inferior to the atrioventricular groove or in the oblique sinus of the heart.

An exemplary medical procedure for positioning the clip 1110 on the heart includes forming a first thoracoscopic port and a second thoracoscopic port in the right chest of the patient. For example, the first thoracoscopic port may be a 12 millimeter port in the third, fourth or fifth intercostal space. The second throracosopic port may be a 5 millimeter port in the third, fourth or fifth intercostal space. The elongate shaft of an endoscope may be inserted through the first thoracoscopic port into the thoracic cavity. A medical grasping device may be advanced through the working channel of the endoscope into the thoracic cavity of the patient, while endoscopic shears or other cutting device is inserted through the second thoracoscopic port into the thoracic cavity. It is noted that in some embodiments, the cutting device may be inserted through the working channel of the endoscope and the grasping device may be advanced through the second port. In other embodiments in which the endoscope has two working channels, each of the devices may be advanced through one of the working channels of the endoscope. The grasping device may be used to grasp a portion of the pericardium, while the cutting device may be used to incise the right pericardium to gain access to pericardial cavities. For example, the right pericardium may be incised about 1 to 2 centimeters anterior to the right phrenic nerve. The endoscope, grasping device and cutting device may then be withdrawn from the ports.

Figure 41:
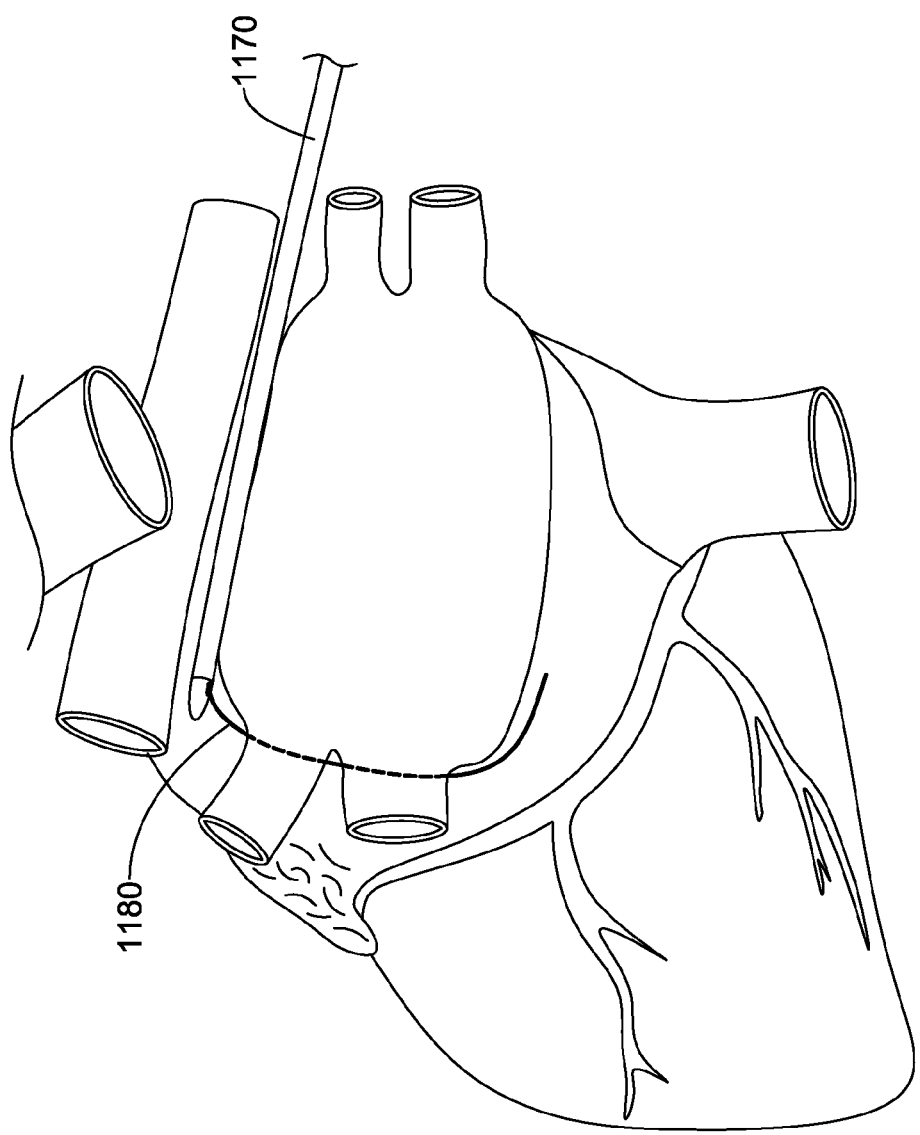

A visualization cannula 1170, such as a blunt tipped visualization cannula, may then be introduced through the first port. As shown in FIG. 41, the visualization cannula 1170 may be inserted through the incision made in the pericardium and positioned into the transverse pericardial sinus via a path anterior to the superior vena cava and posterior to the ascending aorta. A snare catheter 1180 may be advanced through the visualization cannula 1170 into the transverse sinus. The snare catheter 1180 may be tracked around the left lateral side of the heart from the transverse sinus to the posterior side of the heart, such as on or inferior to the atrioventricular groove or into the oblique sinus. The snare catheter 1180 may be positioned inferior to the left pulmonary veins. In some embodiments the snare catheter 1180 may be positioned inferior to the left atrial appendage, while in other embodiments the snare catheter 1180 may be positioned superior to the left atrial appendage.

Figure 42:
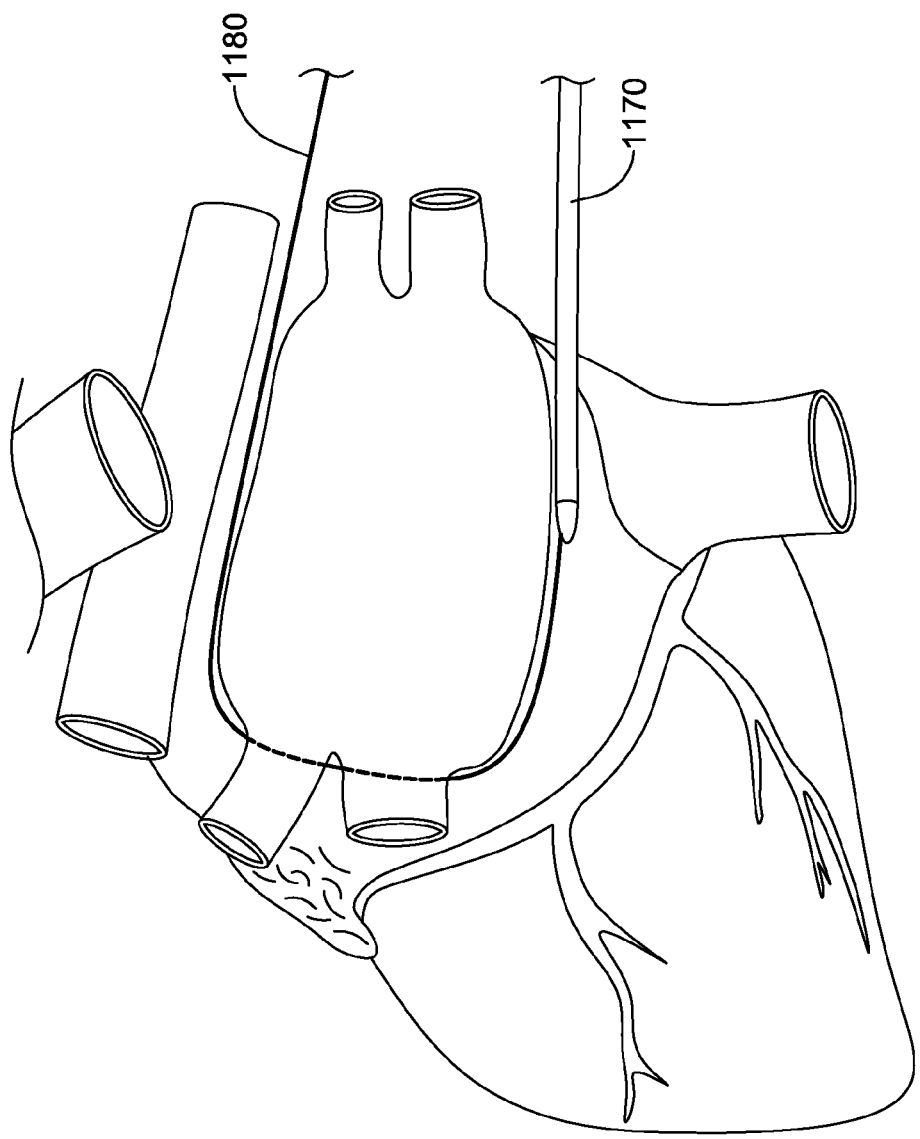

As shown in FIG. 42, with the distal end of the snare catheter 1180 on the posterior side of the heart, the visualization cannula 1170 may be repositioned on the posterior side of the heart. The distal end of the snare catheter 1180 may then be retrieved and withdrawn into the visualization cannula 1170 and out the thoracoscopic port exterior of the chest of the patient. With both the proximal end and the distal end of the snare catheter 1180 located exterior of the patient, the visualization cannula 1170 may be withdrawn from the thoracoscopic port, leaving the snare catheter 1180 in place.

Figure 43:
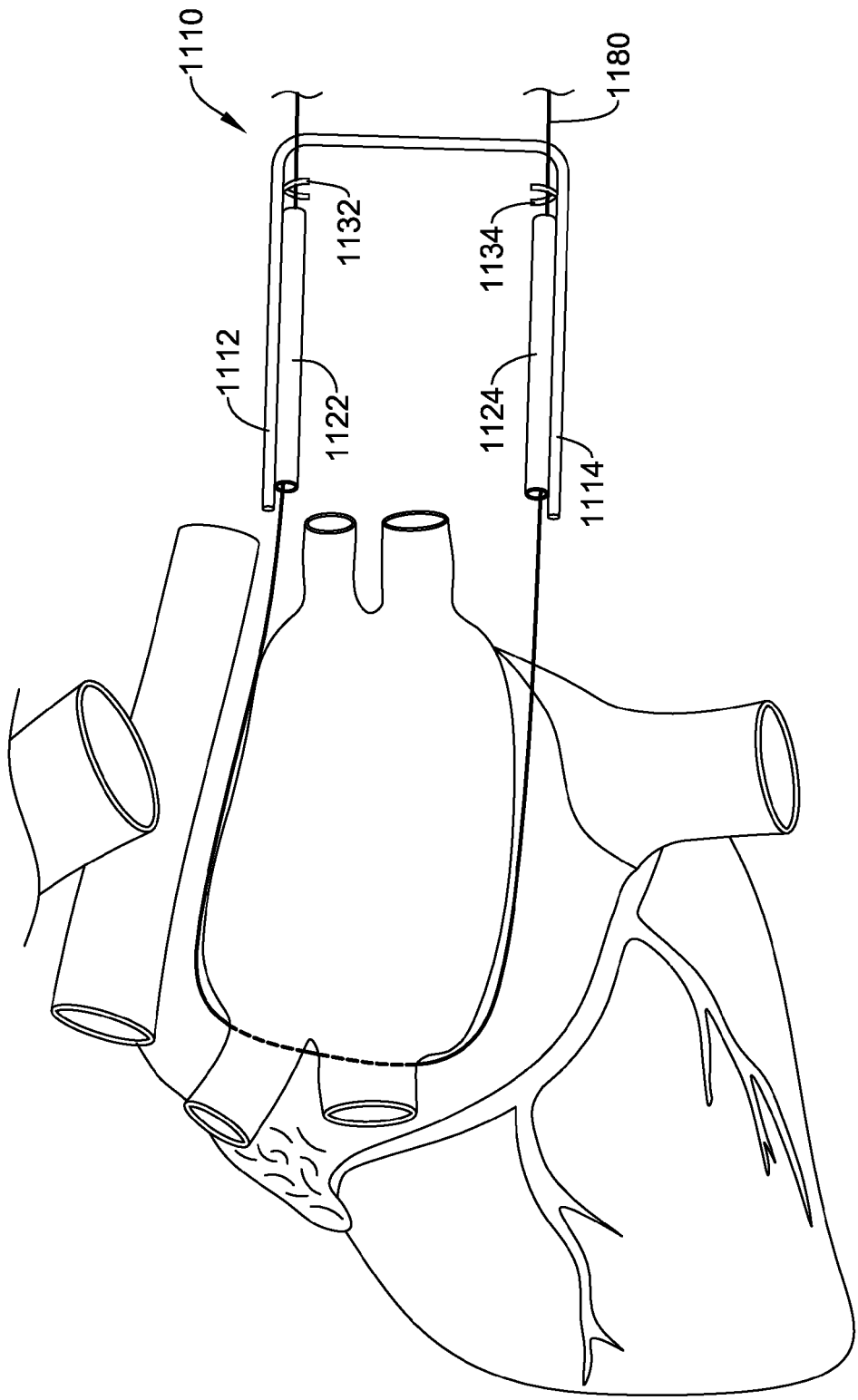

As shown in FIG. 43, the first and second cuffs 1122/1124 of the clip 1110 may then be loaded onto the snare catheter 1180. The proximal end of the snare catheter 1180 may be loaded through the lumen of the first cuff 1122 and the distal end of the snare catheter 1180 may be loaded through the lumen of the second cuff 1124. The clip 1110 may then be collapsed and loaded into the delivery tube 1150.

The delivery tube 1150 may be advanced into the thoracic cavity through a thoracoscopic port to a location proximate the heart. When the delivery tube 1150 and clip 1110 are positioned in proximity to the heart, the clip 1110 may be deployed from the delivery tube 1150. For example, the grasper 1160, or a rigid rod, may be used to expel the clip 1110 out of the delivery tube 1150. Once deployed from the delivery tube 1150, the clip may revert back to its expanded configuration of a C-shape or U-shape.

The grasper 1160 may then be used to advance the clip 1110 along the snare catheter 1180 until the first leg 1112 is positioned in the transverse sinus and the second leg 1114 is positioned on the posterior side of the heart, such as on or inferior to the atrioventricular groove or in the oblique sinus. The placement of the snare catheter 1180 may guide the clip 1110 into proper placement. Echocardiographic images may be taken to determine the optimal or desired position of the clip 1110. The clip 1110 may be slid over the snare catheter 1180, cinching down on the heart, until a desired functionality of the mitral valve is attained. Once properly positioned, the malleable elements 1132/1134 may be crimped to the snare catheter 1180 to secure the clip 1110 to the snare catheter 1180 and prevent further relative movement between the two. Excess lengths of the snare catheter 1180 extending out of the patient's body from the first leg 1112 and the second leg 1114 may then be trimmed and removed from the patient.

Figure 44:
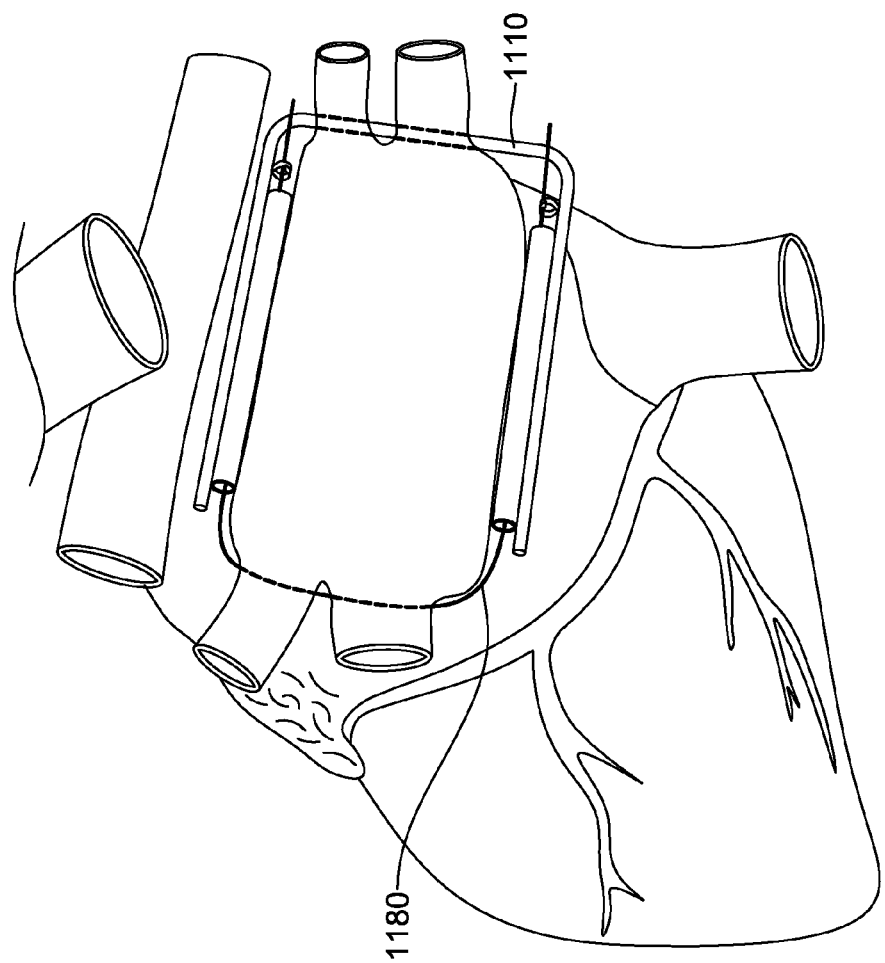

A completed clip implantation is shown in FIG. 44. The position of the clip 1110 and the remaining portion of the snare catheter 1180 extending around the heart provides an inward force on the walls of the heart, altering the anterior-posterior dimension across the annulus of the mitral valve. Reshaping the annulus of the mitral valve may improve coaptation of the leaflets of the mitral valve, and thus improve the efficiency of the heart.

The devices and methods described herein are discussed while referring to a human heart, but may be equally adaptable to other animal hearts, as desired. Furthermore, the devices and methods described herein are discussed while referring to the mitral valve of a heart, but one of skill in the art may also find some features useful with treating the tricuspid valve or other heart valve.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of epicardial treatment of mitral regurgitation associated with the mitral valve of a heart, the anatomy of the heart including an aorta, a pulmonary trunk, a superior vena cava, a transverse sinus, a left atrial appendage, and an oblique sinus, the method comprising:
   providing a clip having an anterior segment, an anterior end, a posterior segment, a posterior end and a lateral segment extending between the anterior segment and the posterior segment;
   positioning the anterior segment in the transverse sinus of the heart; and
   positioning the posterior segment on or inferior to the atrioventricular groove of the heart;
   wherein the clip reshapes the annulus of the mitral valve; and
   wherein said anterior and posterior ends are spaced apart from one another and remain separated by a gap or opening after said positionings and remain spaced apart, separated by said gap or opening while said clip reshapes the annulus.

2. The method of claim 1, wherein the posterior segment applies pressure on the posterior wall of the left ventricle, improving coaptation of the mitral valve.

3. The method of claim 1, wherein the lateral segment extends around a lateral side of the heart below the left atrial appendage of the heart.

4. The method of claim 1, wherein the lateral segment extends around a lateral side of the heart above the left atrial appendage of the heart.

5. The method of claim 1, wherein the mitral valve lies in a plane, and wherein the anterior segment extends above the plane of the mitral valve.

6. The method of claim 1, wherein the mitral valve lies in a plane, and wherein the posterior segment extends below the plane of the mitral valve.

7. The method of claim 1, further comprising a pad extending from the clip, wherein the pad applies pressure on the posterior wall of the left ventricle, improving coaptation of the mitral valve.

* * * * *